US012617836B2

(12) United States Patent
Gazit et al.

(10) Patent No.: US 12,617,836 B2
(45) Date of Patent: May 5, 2026

(54) TUMOR ENVIRONMENT SPECIFIC EXPRESSION OF EFFECTOR GENES

(71) Applicant: THE NATIONAL INSTITUTE FOR BIOTECHNOLOGY IN THE NEGEV LTD., Beer Sheva (IL)

(72) Inventors: Roi Gazit, Kidron (IL); Angel Porgador, Lehavim (IL)

(73) Assignee: THE NATIONAL INSTITUTE FOR BIOTECHNOLOGY IN THE NEGEV LTD., Beer Sheva (IL)

( * ) Notice: Subject to any disclaimer, the term of this patent is extended or adjusted under 35 U.S.C. 154(b) by 1048 days.

(21) Appl. No.: 17/699,428

(22) Filed: Mar. 21, 2022

(65) Prior Publication Data

US 2022/0315640 A1 Oct. 6, 2022

Related U.S. Application Data

(63) Continuation of application No. PCT/IL2020/051026, filed on Sep. 21, 2020.

(60) Provisional application No. 62/949,540, filed on Dec. 18, 2019, provisional application No. 62/903,871, filed on Sep. 22, 2019.

(51) Int. Cl.
| | |
|---|---|
| *C07K 14/725* | (2006.01) |
| *A61K 40/11* | (2025.01) |
| *A61K 40/15* | (2025.01) |
| *A61K 40/31* | (2025.01) |
| *A61K 40/42* | (2025.01) |
| *A61P 35/00* | (2006.01) |
| *C12N 15/86* | (2006.01) |

(52) U.S. Cl.
CPC .......... *C07K 14/7051* (2013.01); *A61K 40/11* (2025.01); *A61K 40/15* (2025.01); *A61K 40/31* (2025.01); *A61K 40/4205* (2025.01); *A61P 35/00* (2018.01); *C12N 15/86* (2013.01); *C07K 2317/622* (2013.01); *C07K 2319/03* (2013.01); *C07K 2319/70* (2013.01)

(58) Field of Classification Search
CPC ................................................. C07K 14/7051
See application file for complete search history.

(56) References Cited

U.S. PATENT DOCUMENTS

| | | | | |
|---|---|---|---|---|
| 10,548,911 B2 * | 2/2020 | Phipps | ................... | A61K 45/06 |
| 2016/0130359 A1 * | 5/2016 | Dimitrov | ........... | A61K 47/6889 |
| | | | | 536/23.53 |
| 2019/0233516 A1 | 8/2019 | Monsonego et al. | | |
| 2022/0315640 A1 | 10/2022 | Gazit et al. | | |

FOREIGN PATENT DOCUMENTS

WO WO-2019159173 A1 * 8/2019 ........... C12N 15/867

OTHER PUBLICATIONS

Holman (2004) Protein Similarity Score: A Simplified Version of the Blast Score as a Superior Alternative to Percent Identity forClaiming Genuses of Related Protein Sequences. Santa Clara High Technol. Law J. 21 [1]:55-99.
Sentman (2013) Challenges of creating effective chimeric antigen receptors for cancer therapy. Immunotherapy 5 [8]:783-785.
Dow et al (2014) Conditional Reverse Tet-Transactivator Mouse Strains for the Efficient Induction of TRE-Regulated Transgenes in Mice. PLoS One 9[4]:e95236.
Wang et al (2009) The Transcriptional Specificity of NF-kBDimers Is Coded within the kB DNA Response Elements. Cell Report. 2:824-839.
Mojic et al (2017) The Dark Side of IFN-y: Its Role in Promoting Cancer Immunoevasion. Int. J. Mol. Sci. 19:89.
Decker et al (1997) GAS Elements: A Few Nucleotides with a Major Impact on Cytokine-Induced Gene Expression. J. InterferonCytokine Res. 17:121-134.
U.S. Appl. No. 18/244,259, filed Sep. 2023.
Haen et al. (2020). Towards new horizons: characterization, classification and implications of the tumour antigenic repertoire. Nature Reviews Clinical Oncology, 17(10), 595-610. doi: 10.1038/s41571-020-0387-x. Epub Jun. 22, 2020. PMID: 32572208; PMCID: PMC7306938.
Mizuguchi et al (1995). Characterization of the 5'-Flanking Region of the Gene for the yChain of Human Fibrinogen. Journal of Biological Chemistry, 270(47), 28350-28356.—pp. 7.
Kloss et al (2013). Combinatorial antigen recognition with balanced signaling promotes selective tumor eradication by engineered T cells. Nature biotechnology, 31(1), 71-75.—pp. 6.
Fisher et al (Feb. 2014). The two faces of IL-6 in the tumor microenvironment. In Seminars in immunology (vol. 26, No. 1, pp. 38-47). Academic Press.—pp. 10.
Ede et al (2016) Quantitative Analyses of Core Promoters Enable Precise Engineering of Regulated Gene Expression in Mammalian Cells, ACS Synthetic Biology, 5:395-404. https://doi.org/10.1021/acssynbio.5b00266.
PCT International Search Report for International Application No. PCT/IL2020051026, mailed Dec. 14, 2020, App.
Javan et al (2017) Hypoxia-inducible tumour-specific promoters as a dual-targeting transcriptional regulation system for cancer gene therapy, ECancer, vol. 11, 751, DOI: 10.3332/ecancer.2017.751.
Dotti et al (2013) Design and development of therapies using chimeric antigen receptor-expressing t Cells, Immunol. Rev., vol. 257, No. 1, pp. 107-126, doi:10.1111/imr.12131.
Sakemura et al (2016) A Tet-On Inducible System for Controlling CD19-Chimeric Antigen Receptor Expression Upon Drug Administration, Cancer Immunolog Res 4(8): 658-668, DOI: 10.1158/2326-6066.CIR-16-0043.

(Continued)

*Primary Examiner* — Christopher M Babic
*Assistant Examiner* — Hanan Isam Abuzeineh
(74) *Attorney, Agent, or Firm* — The Roy Gross Law Firm, LLC; Roy D. Gross

(57) ABSTRACT

A Tumor Micro-Environment (TME) responsive expression vector including a nucleic acid sequence of a synthetic promoter, comprising two or more promoter-response-elements inducing expression of an immune-effector gene.

18 Claims, 14 Drawing Sheets
(8 of 14 Drawing Sheet(s) Filed in Color)

Specification includes a Sequence Listing.

(56) References Cited

OTHER PUBLICATIONS

Viale (2013) Therapeutic Improvement of a Stroma-Targeted CRAd by Incorporating Motives Responsive to the Melanoma Microenvironment, J. Invest. Derm 133 (11):2576-2584, doi: 10.1038/jid.2013. 191.

PCT International Search Report For International Application No. PCT/IL2019/050182, mailed Aug. 2, 2019, 6pp.

PCT Written Opinion for International Application No. PCT/IL2019/ 050182 Completed May 21, 2019; Mailed Aug. 2, 2019, 8 Pages.

PCT International Search Report for International Application No. PCT/IL2020051026, mailed Dec. 14, 2020, 4pp.

PCT Written Opinion for International Application No. PCT/ IL2020051026, mailed Dec. 14, 2020, 5pp.

* cited by examiner

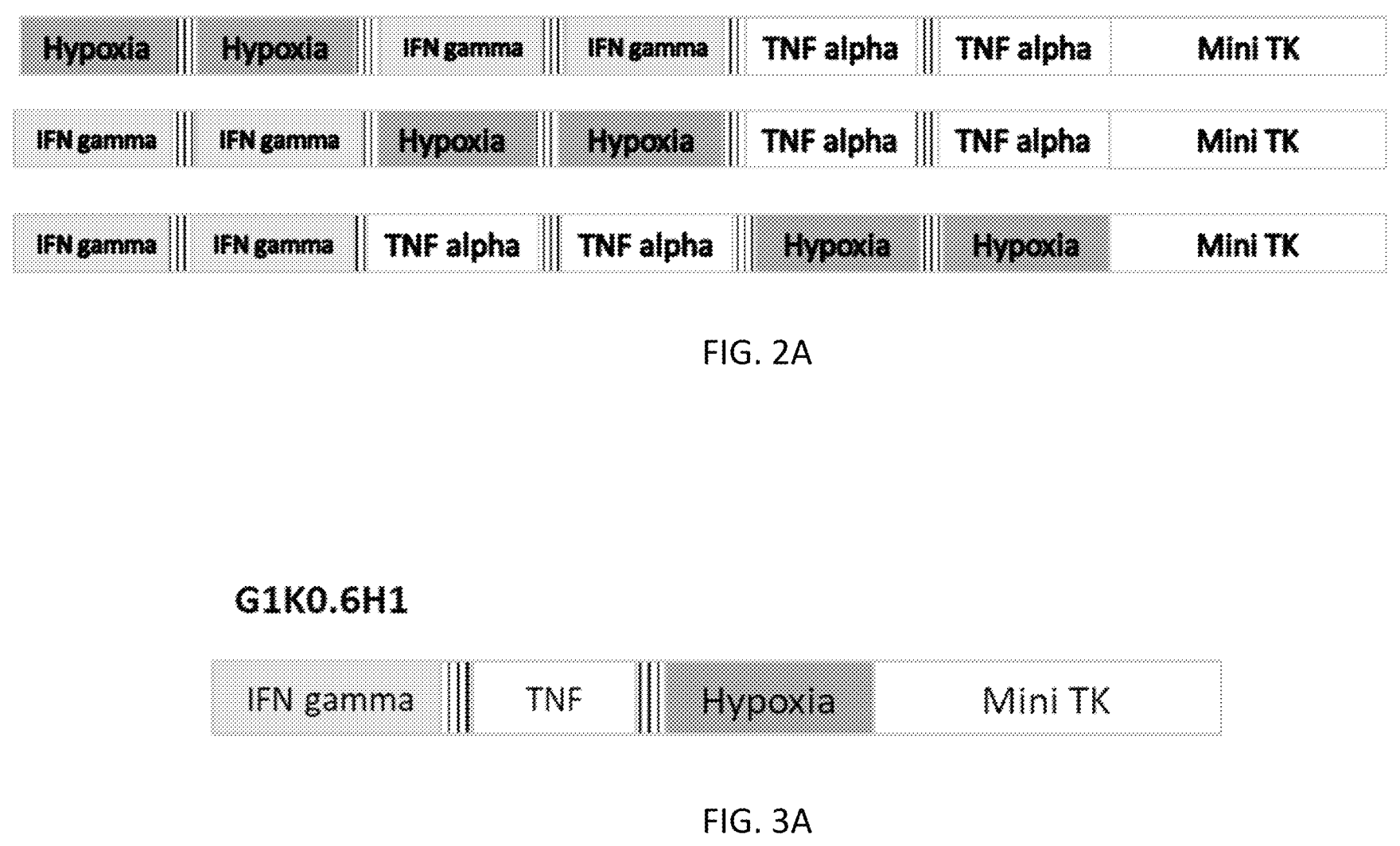

| Hypoxia | Hypoxia | IFN gamma | IFN gamma | TNF alpha | TNF alpha | Mini TK |
|---|---|---|---|---|---|---|

| IFN gamma | IFN gamma | Hypoxia | Hypoxia | TNF alpha | TNF alpha | Mini TK |
|---|---|---|---|---|---|---|

| IFN gamma | TNF alpha | TNF alpha | Hypoxia | Hypoxia | Mini TK |
|---|---|---|---|---|---|

| IFN gamma | TNF | Hypoxia | Mini TK |
|---|---|---|---|

FIG. 3A

JIMT1

HEK293T

| Marker X-GMean | |
|---|---|
| All | 4,976.71 |
| All | 1,436.66 |

FIG. 8A

TUMOR ENVIRONMENT SPECIFIC EXPRESSION OF EFFECTOR GENES

FIELD OF INVENTION

The present disclosure generally relates to the field of focusing immune cells activity within tumor-microenvironment. For example, the expression of a chimeric antigen receptor (CAR) specifically to tumor tissue that will focus anti-cancer immune cells and spare normal healthy tissues.

BACKGROUND

Harnessing the immune system to eradicate cancer has proved highly efficient in recent years.

The main success is the engineered immune cells, such as Chimeric-Antigen-Receptor T-cells (CAR-T), which are already approved by the FDA for the treatment of few types of cancers that have no other cure.

However, although CAR-T can reach tumors and metastasis throughout a patient's body, the specificity of the engineered receptor does not fully distinguish between tumor cells and normal cells, since tumors often are not having an absolutely unique antigen that is not expressed by any other normal cells in the body. As a result, several CAR treatments caused toxic immune response, similar to Graft-vs-Host-Disease (GVHD), and even death that resulted from the CAR treatment during clinical trials. Importantly, unlike antibodies or other treatments, CAR-T are having an extreme potency to identify antigens, even at minute levels, and efficiently attack the cells that express them—both cancerous and normal healthy cells. Therefore, focusing the CAR expression into the tumor-microenvironment may improve specificity and reduce ON-antigen OFF-tumor activities.

Attempts to achieve non-constitutive expression of CAR within engineered immune cells have been made. An example includes applying an "ON-OFF switch" within the CAR expression vector, by utilizing a promoter activated only in the presence of an exogenously provided molecule (such as tetracycline/doxycycline). This may allow for turning off CAR expression in case of pronounced adverse symptoms but will turn off also the positive activity of the CAR T-cells against the tumor cells and thus terminates a potent CAR treatment.

There remains an unmet need for controlled CAR expression that reduces the risks of its life-threatening "ON-target OFF-tumor", while allowing effective elimination of tumors.

SUMMARY

The following embodiments and aspects thereof are described and illustrated in conjunction with compositions and methods which are meant to be exemplary and illustrative, not limiting in scope. In various embodiments, one or more of the above-described problems have been reduced or eliminated, while other embodiments are directed to other advantages or improvements.

The platform includes the tumor environment (TME) responsive expression vectors, including nucleic acid sequences encoding for a synthetic promoter (also referred to herein as "CARTIV" promoters) comprising multiple TME-dependent promoter response elements that is conjugated to effector-genes such as, but not limited to, nucleic acid sequence encoding for Chimeric Antigen Receptor.

According to some embodiments, the ligand binding domain of the CAR is capable of specifically binding to Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), Galactin, Ral-B, Integrin Alpha-V-Beta3 (CD51/CD61), an abnormal p53 protein, or an abnormal RAS protein such as K-Ras (V-Ki-ras2 Kirsten rat sarcoma viral oncogene). Each possibility is a separate embodiment. According to some embodiments, the ligand-binding domain of the CAR is capable of specifically binding to Her2.

Advantageously, the TME responsive vector is designed such that binding of two or more factors that are present in the TME to the promoter response element induces the expression of the effector-gene. In the absence of such TME factors, the promoter expression is basal. This advantageously ensures minimal- and possibly even down to no expression of effector-mechanisms, such as CAR, in tissue environments different from that of the tumor. Accordingly, these promoters endogenously upregulate the expression of effector mechanisms, such as CARs, in immune-cells within a tumor microenvironment, thus directing activities against the tumor while sparing normal tissues.

According to some embodiments, the expression vector may include more than two TME dependent promoter response elements. This may serve to ensure that the highest expression level is solely obtained where the specific combination of TME factors is found. As a further advantage, the TME responsive vector is designed such that levels of the two or more factors physiological to the TME ensure an optimal expression from the promoter. According to some embodiments, an optimal expression is the highest expression. According to some embodiments, an optimal expression ensures highest expression only when the combination of the two or more factors are found. According to some embodiments, an optimal expression only in the presence of three or more factors, thereby further improve the focus on tumor and spare of normal tissues.

Advantageously, the synthetic custom-made promoter can be designed to fit the actual TME-signature (i.e.—the factors found within the TME and not in normal tissues) of a specific patient or patients group, thus ensuring an uttermost specific and efficient response.

According to some embodiments, there is provided a tumor microenvironment (TME) responsive expression vector comprising a nucleic acid sequence encoding a synthetic promoter, said promoter comprising two or more TME dependent promoter response elements (PRE); and a nucleic acid sequence encoding a CAR; wherein said TME responsive expression vector is designed, such that in the presence of one or more TME factors present in the TME to the promoter response element induces expression of the CAR, and wherein, in the absence of binding of the one or more TME factor to the promoter response element, low or essentially no effector gene is expressed.

According to some embodiments, the CAR is a chimeric antigen T-cell receptor (CAR-T), a chimeric antigen Natural Killer (NK) cell receptor (CAR-NK), a chimeric innate receptor, or other immune-effectors including, but not limited to: cytokines, chemokines, chemokine-receptors, proteases, micro-RNAs, or combinations thereof.

According to some embodiments, the promoter response element comprises multiple response elements selected from the list consisting of, but not limited to: an interferon-gamma (IFN-γ) element response, a Nuclear Factor kappa-B (NF-κB) response element, a hypoxia response element, an IL-6 response elements, a Heat shock protein 70 (HSP-70) response element, an IL-1 response element, an IL-4 response elements, an IL-6 response elements, an IL-8 response element, an IL-10 response element, an IL-11 response element, an IL-12 response element, an IL-15 response element, an IL-18 response element, an IL-17 response element, an IL-21 response element, an IL-35 response element, a TGF-β response element, a GM-CSF response element, a Hepatic Growth Factor (HGF) response element, an Aryl Hydrogen Receptor (AhR) response element, a PGE2 response element or any other suitable TME factor response element or combinations thereof.

According to some embodiments, the promoter response element comprises one or more response elements selected from the list consisting of, but not limited to: an interferon-gamma (IFN-γ) response element, a Nuclear Factor kappa-B (NF-κB) response element, and a hypoxia response element. According to some embodiments, the TME responsive vector is designed such that the hypoxia response element is located proximally to the promoter, downstream of the IFN-γ response element and the NF-κB response element.

According to some embodiments, the promoter response element comprises one or more response elements selected from the list consisting of, but not limited to: TGF-β response element, an IL-6 response element, an IFN-γ response element or any combination or derivatives thereof.

According to some embodiments, the promoter response element comprises a TGF-β response element or TGF-β derived response element and at least one additional response element selected from the list consisting of, but not limited to: an IL-6 response element, an IFN-γ response element or any combination or derivatives thereof.

According to some embodiments, the promoter response element comprises at least two TGF-β response element or TGF-β derived response element and at least one additional response element selected from the list consisting of, but not limited to: an IL-6 response element, an IFN-γ response element or any combination or derivatives thereof.

According to some embodiments, the promoter response element comprises a TGF-β derived response element and at least one additional response element selected from the list consisting of, but not limited to: an IL-6 response element, an IL-6 derived response element, an IFN-γ derived response element or any combination thereof.

As used herein, the terms "derived", "derivatives" and "modified" with regards to response elements may refer to response elements including at least one or at least two nucleotide substitution vis-à-vis the response element from which they are derived, as further elaborated herein.

According to some embodiments, the promoter response element may be inserted into the synthetic promoter in a sense (5' to 3') or anti-sense (3' to 5') direction.

According to some embodiments, the promoter response element comprises a nucleic acid selected from the group consisting of: TTCCGGGAA set forth in SEQ ID NO: 1, GGGAATTTCC set forth in SEQ ID NO: 2, GACCTT-GAGTACGTGCGTCTCTGCACGTATG set forth in SEQ ID NO: 3, GCGCTTCCTGACAGTGACGCGAGCCG set forth in SEQ ID NO: 4, or any combination thereof.

According to some embodiments, the promoter response element comprises a nucleic acid selected from the group consisting of:

```
                          >set forth in SEQ ID NO: 22
TACAGGGACAGCAGAGATCCAGTTTGGACTAGCCCGGTCGCACTAGTTCT

AGAACTTCCCGGAAATAGGGTGGGCAAGTATTTCCGGGAAATTCTAGAGG

GAGTTCCCGGGGACTTTCCGGGGATTTTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 23
TACAGGGACAGCAGAGATCCAGTTTGGACTAGCCCGGTCGCACTAGTTCT

AGAACTTCCCGGAAGTAGGGTGGGCAAGTACTTCCCGGAAGTTCTAGAGG

AAATTTTCGGGGACTTTCCGGGGGTTCTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 24
TACAGGGACAGCAGAGATCCAGTTTGGACTAGCCCGGTCGCACTAGTTCT

AGAACTTCCCGGAAGTAGGGTGGGCAAGTACTTCCGGGAAATTCTAGAGG

GAGTTCTCGGGGACTTTCCGGGAATTTTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 25
TACAGGGACAGCAGAGATCCAGTTTGGACTAGCCCGGTCGCACTAGTTCT

AGAACTTCCCGGAAGTAGGGTGGGCAAGTATTTCCCGGAAGTTCTAGAGG

AAGTTCTCGGGGACTTTCCGGGAGATTCTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 26
TACAGGGACAGCAGAGATCCAGTTTGGACTAGCCCGGTCGCACTAGTTCT

AGAACTTCCGGGAAATAGGGTGGGCAAGTACTTCCGGGAAATTCTAGAGG

GGATTTCCGGGGACTTTCCGGGAGGTTCTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 27
TACAGGGACAGCAGAGATCCAGTTTGGACTAGCCCGGTCGCACTAGTTCT

AGAACTTCCGGGAAATAGGGTGGGCAAGTACTTCCGGGAAGTTCTAGAGG

AGGTTTTCGGGGACTTTCCGGGAGGTTTCCTCTAGATATTAAGGTGACGCGT
```

-continued

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 28
TACAGGGACAGCAGAGATCCAGTTTGGACTAGCCCGGTCGCACTAGTTCT

AGAACTTCCGGGAAGTAGGGTGGGCAAGTATTTCCCGGAAGTTCTAGAGG

GGGTTTTCGGGGACTTTCCGGAGGTTTCCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 29
TACAGGGACAGCAGAGATCCAGTTTGGACTAGCCCGGTCGCACTAGTTCT

AGAACTTCCGGGAAGTAGGGTGGGCAAGTATTTCCGGGAAATTCTAGAGG

GAGTTCTCGGGGACTTTCCGGGGATTTTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 30
TACAGGGACAGCAGAGATCCAGTTTGGACTAGCCCGGTCGCACTAGTTCT

AGAATTTCCCGGGAAATAGGGTGGGCAAGTACTTCCGGGAAATTCTAGAGG

GGGTTTCCGGGGACTTTCCGGGGGGTTTTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 31
TACAGGGACAGCAGAGATCCAGTTTGGACTAGCCCGGTCGCACTAGTTCT

AGAATTTCCCGGGAAATAGGGTGGGCAAGTACTTCCGGGAAATTCTAGAGG

GGGTTTCCGGGGACTTTCCGGGGGGTTTTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 32
TACAGGGACAGCAGAGATCCAGTTTGGACTAGCCCGGTCGCACTAGTTCT

AGAATTTCCCGGGAAATAGGGTGGGCAAGTATTTCCGGGAAATTCTAGAGG

AGGTTCTCGGGGACTTTCCGGGAGTTTTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 33
TACAGGGACAGCAGAGATCCAGTTTGGACTAGCCCGGTCGCACTAGTTCT

AGAATTTCCCGGGAAATAGGGTGGGCAAGTATTTCCGGGAAATTCTAGAGG

AGGTTTTCGGGGACTTTCCGGGAGTTTCCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 34
TACAGGGACAGCAGAGATCCAGTTTGGACTAGCCCGGTCGCACTAGTTCT

AGAATTTCCCGGGAAATAGGGTGGGCAAGTATTTCCGGGAAGTTCTAGAGG

AAGTTTTCGGGGACTTTCCGGGAATTTTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

-continued

>set forth in SEQ ID NO: 35
TACAGGGACAGCAGAGATCCAGTTTGGACTAGCCCGGTCGCACTAGTTCT

AGAATTTCCGGGAAATAGGGTGGGCAAGTATTTCCCGGAAGTTCTAGAGG

AGATTCTCGGGGACTTTCCGGGGGTTCTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 36
TACAGGGACAGCAGAGATCCAGTTTGGACTAGCCCGGTCGCACTAGTTCT

AGAATTTCCGGGAAGTAGGGTGGGCAAGTACTTCCGGGAAATTCTAGAGG

GGGTTTCCGGGGACTTTCCGGAGATTCTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 37
TACAGGGACAGCAGAGATCCAGTTTGGACTAGCCCGGTCGCACTAGTTCT

AGAATTTCCGGGAAGTAGGGTGGGCAAGTACTTCCGGGAAATTCTAGAGG

GGGTTTCCGGGGACTTTCCGGAGATTCTCTCTAGATATTAAGGTGACGCGT

GTGGCCTCGAACACCGAGCGACCCTGCAGCGACCCGCTTAAAAGCGGCCG

CCATGGGCCGCCATGGCCTCCTCCGAGGACGTCATCAAGGAGTTCATGC,

>set forth in SEQ ID NO: 38
TACAGGGACAGCAGAGATCCAGTTTGGACTAGCCCGGTCGCACTAGTTCT

AGAACTTCCCGGGAAATAGGGTGGGCAAGTATTTCCCGGAAGTTCTAGAGG

AGGTTTTCGGGGACTTTCCGGGATTCCCTCTAGATATTAAGGTGACGCGTG

TGGCCTCGAACACCGAGCGACCCTGCAGCGACCCGCTTAAAAGCGGCCGC

CATGGGCCGCCATGGCCTCCTCCGAGGACGTCATCAAGGAGTTCATGC,

>set forth in SEQ ID NO: 39
TACAGGGACAGCAGAGATCCAGTTTGGACTAGCCCGGTCGCACTAGTTCT

AGTTCCGGGAAGTGGGTGGGCAATATTTCCCGGAAGTTTAGAGGAAGTTT

TCGGGGACTTCCGGAAATTCCCTCTAGATATTAAGGTGACGCGTGTGGCC

TCGAACACCGAGCGACCCTGCAGCGACCCGCTTAAAAGCGGCCGCCATGG

GCCGCCATGGCCTCCTCCGAGGACGTCATCAAGGAGTTCATGC,

>set forth in SEQ ID NO: 40
TACAGGGACAGCAGAGATCCAGTTTGGACTAGCCCGGTCGCACTAGTTCT

AGAACTTCTCGGAAATAGGGTGGGCAAGTACTGTGGCCTCGAACACCGAG

CGACCCTGCAGCGACCCGCTTAAAAGCGGCCGCCATGGGCCGCCATGGCC

TCCTCCGAGGACGTCATCAAGGAGTTCATGCAGACCAAGTCTCTGCTACC or combinations thereof.

Each possibility is a separate embodiment.

According to some embodiments, the promoter response element comprises a nucleic acid selected from the nucleic acid sequences set forth in SEQ IDs NOs: 1-4 or any combination thereof. Each possibility is a separate embodiment.

According to some embodiments, the promoter response element comprises a nucleic acid selected from the nucleic acid sequences set forth in SEQ ID NOs: 22-40 or any combination thereof. Each possibility is a separate embodiment.

According to some embodiments, the promoter response element comprises the nucleic acid sequence:

>set forth in SEQ ID NO: 41

TACAGGGACAGCAGAGATCCAGTTTGGACTAGCCCGGTCGCACTAGTTCT

AGAAYTTCCSGGAARTAGGGTGGGCAAGTAYTTCCSGGAARTTCTAGAGG

RRRTTYYCGGGGACTTTCCGGRRRTTYYCTCTAGATATTAAGGTGACGCG

TGTGGCCTCGAACACCGAGCGACCCTGCAGCGACCCGCTTAAAAGCGGCC

GCCATGGGCCGCCATGGCCTCCTCCGAGGACGTCATCAAGGAGTTCATGC,
wherein Y = C or T, S = C or G and R = A or G.

According to some embodiments, the synthetic promoter comprises additional nucleotides flanking the promoter response element and or spacing between promoter response elements.

According to some embodiments, the two or more promoter response elements are modified on one or more positions. According to some embodiments, the modification generates a sequence with increased TME factor binding vis-à-vis the native sequence.

As a non-limiting example, the synthetic promoter may include response elements of Hypoxia (or other TME factor response element) as derived from various hypoxia dependent target genes (LDHA/EPO/VEGF), such as the shared part of the HBS sequence of the LDHA/EPO/VEGF and/or the HAS sequence of EPO gene, as well as a linker of about 6-9 nucleotides which is not found in the target genes. This sequence is referred to as a "basic hypoxia promoter response element (PRE)", as set forth in SEQ ID NO: 42 outlined below.

>SEQ ID NO:42

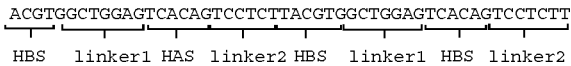

HBS   linker1 HAS  linker2 HBS  linker1 HBS  linker2

A non-limiting example, of a modified basic hypoxia PRE is set forth in SEQ ID 43:

>RCGTGSCTGGAGTMACAGTCCTCTTRCGTGSCTGGAGTMACAGTCC

TCTT,
wherein R = A/G, S = C/G and M = A/C.

According to some embodiments, the modified TME factor PRE is the synthetic PRE that induce the least leakiness and the highest response to hypoxia stimulation.

A non-limiting example for a modified IFN-γ PRE is set forth in SEQ ID NO: 44:

>ACTTCCSGGAARTAGGGTGGGCAAGTACTTCCSGGAART,
wherein R = A/G and Y = C/T.

A non-limiting example for a modified NF-κB PRE is set forth in SEQ ID NO: 45:

>GGGGGTTTYCGGGGACTTTCCGGRRRTTTT
wherein R = A/G and Y = C/T.

According to some embodiments, the synthetic promoter may include at least one TGF-β derived response element. According to some embodiments, the at least one TGF-β derived response element has the sequence GKCKMGMCnn set forth in SEQ ID NO: 46, wherein K=G/T and M=A/C and wherein n=any nucleotide.

According to some embodiments, the synthetic promoter may include more than one TGF-β derived response elements. According to some embodiments, the more than one TGF-β derived response elements may be spaced apart by a spacer sequence as set forth in GKCKMGMCggcgcGKCKMGM SEQ ID NO: 47.

It is understood by one of ordinary skill in the art that herein disclosed spacers may have other nucleic acid sequences than those presented below (in lower case) and such spacer variants are within the scope of the present disclosure.

According to some embodiments, the synthetic promoter may include 4 or more TGF-β derived response elements. According to some embodiments, the more than four TGF-β derived response elements may be spaced apart by same or different spacers.

According to some embodiments, the synthetic promoter may comprise the nucleic acid sequence set forth in SEQ ID NO: 48, namely: GKCKMGMCggcgcGKCKMGMCat-tctagaGKCKMGMCggcgcGKCKMGMC, as.

According to some embodiments, the synthetic promoter may include 4 or more TGF-β derived response elements and at least one, optionally modified, additional response element. According to some embodiments, the additional response element may by an IL-6 derived response element. According to some embodiments, the IL-6 derived response element may have the sequence TTCYSGGAAn set forth in SEQ ID NO: 49, wherein Y=C/T and S=C/G and wherein n=any nucleotide.

According to some embodiments, the synthetic promoter may include 4 or more TGF-β derived response elements and at least two IL-6 derived response elements. According to some embodiments, the at least two IL-6 derived response elements may be spaced apart by a spacer sequence as set forth in TTCYSGGAAatagggtgggcaagtatTTCYSGGAA, SEQ ID NO: 50 According to some embodiments, the more than four TGF-β derived response elements and the at least two IFN-γ derived response element may be spaced apart by same or different spacers.

According to some embodiments, the synthetic promoter may include the nucleic acid sequence set forth in SEQ ID NO: 51, namely:

GKCKMGMCggcgcGKCKMGMCATTCTAGAGKCKMGMCggcgcGKCKM

GMCtctagaatTTCYSGGAAatagggtgggcaagtatTTCYSGGAA.

According to some embodiments, the synthetic promoter may include 4 or more TGF-β derived response elements and at least two IFN-γ response elements. According to some embodiments, the at least two IFN-γ response elements may be spaced apart by a spacer.

According to some embodiments, the synthetic promoter may include 4 or more TGF-β derived response elements, at least two IFN-γ response elements, and at least one IL-6 derived response elements.

According to some embodiments, the synthetic promoter may include 4 or more modified TGF-β response elements and at least one modified IL-6 response element. According to some embodiments, the modified IL-6 response element may have the sequence GCGCTTCCTGACAGTGACGYBWGCCG set forth in SEQ ID NO: 52, wherein Y=C/T, B=C/G/T and W=A/T. According to some embodiments, the synthetic promoter may further include one or more IFN-γ response elements.

According to some embodiments, synthetic promoter may have the sequence set forth in SEQ ID NO: 53 (also referred to as a "consensus sequence" or "library sequence"), namely:

GKCKMGMCggcgcGKCKMGMCATTCTAGAGKCKMGMCggcgcGKC
KMGMCTCTAGAATGCGCTTCCTGACAGTGACGYBWGCCGATTCTAGAGG
GGGTTTTCGGGGACTTTCCGGGAATTTTCTCTAGA According to some embodiments, synthetic promoter may have the sequence set forth in SEQ ID NO: 54 (also referred to as a "consensus sequence" or "library sequence"), namely:

TTCYSGGAAATAGGGTGGGCAAGTATTTCYSGGAAattctagaGGGG
GTTTTCGGGGACTTTCCGGGAATTTTCtctagaatGKCKMGMCggcgcG
KCKMGMCattctagaGKCKMGMCggcgcGKCKMGMCTCTAGA According to some embodiments, synthetic promoter may have the sequence set forth in SEQ ID NO: 55 (also referred to as a "consensus sequence" or "library sequence"), namely:

GKCKMGMCggcgcGKCKMGMCATTCTAGAGKCKMGMCggcgcGKC
KMGMCtctagaatGCGCTTCCTGACAGTGACGYBWGCCGattctagaGG
GGGTTTTCGGGGACTTTCCGGGAATTTTCtctaga According to some embodiments, the synthetic promoter may have the sequence set forth in SEQ ID NO: 56, namely:

GACTAGACTAGTTCTAGAGTCGAGACGGCGCGTCTAGACATTCTAGAGTC

TAGCCGGCGCGCCTCTAGAATTTCTGGGAAATAGGGTGGGCAAGTATTTC

TCGGAAATTCTAGAGGGGGTTTTCGGGGACTTTCCGGGAA

According to some embodiments, the synthetic promoter may have the sequence set forth in SEQ ID NO: 57, namely:

GACTAGACTAGTTCTAGAGTCGAGCCGGCGCGTCTCGACATTCTAGAGTC

TAGACGGCGCGTCTAGACTCTAGAATGCGCTTCCTGACAGTGACGCGTGC

CGATTCTAGAGGGGGTTTTCGGGGACTTTCCGGGAA

According to some embodiments, the synthetic promoter may have the sequence set forth in SEQ ID NO: 58, namely:

GACTAGACTAGTTCTAGAGTCTAGACGGCGCGTCGAGCCATTCTAGAGTC

TAGACGGCGCGGCTCGACTCTAGAATGCGCTTCCTGACAGTGACGCTTGC

CGATTCTAGAGGGGGTTTTCGGGGACTTTCCGGGAA

According to some embodiments, the synthetic promoter may have the sequence set forth in SEQ ID NO: 59, namely:

GACTAGACTAGTTCTAGAGTCGAGACGGCGCGTCGAGACATTCTAGAGTC

GAGACGGCGCGTCTAGACTCTAGAATGCGCTTCCTGACAGTGACGTTAGC

CGATTCTAGAGGGGGTTTTCGGGGACTTTCCGGGAA

According to some embodiments, the synthetic promoter may have the sequence set forth in SEQ ID NO: 60, namely:

GACTAGACTAGTTCTAGAGTCTAGACGGCGCGTCGCGACATTCTAGAGTC

TAGCCGGCGCGTCGCGCCTCTAGAATGCGCTTCCTGACAGTGACGCTAGC

CGATTCTAGAGGGGGTTTTCGGGGACTTTCCGGGAA

According to some embodiments, the synthetic promoter may have the sequence set forth in SEQ ID NO: 61, namely:

GACTAGACTAGTTCTAGAGGCTAGCCGGCGCGGCTAGACATTCTAGAGGC

TAGCCGGCGCGTCGCGACTCTAGAATGCGCTTCCTGACAGTGACGTTAGC

CGATTCTAGAGGGGGTTTTCGGGGACTTTCCGGGAA

According to some embodiments, the synthetic promoter may have the sequence set forth in SEQ ID NO: 62, namely:

AGTCTAGACGGCGCGGTCTGGGAAATAGGGTGGGCAAGTATTTCTGGGAA

ATTCTAGAGGGGGTTTTCGGGGACTTTCCGGGAA

According to some embodiments, the synthetic promoter may have the sequence set forth in SEQ ID NO: 63, namely:

GACTAGACTAGTTCTAGAGGCTAGCCGGCGCGTCTAGCCATTCTAGAGT

CTAGACGGCGCGTCTCGCCTCTAGAATGCGCTTCCTGACAGTGACGTCA

GCCGATTCTAGAGGGGGTTTTCGG

According to some embodiments, the synthetic promoter may have the sequence set forth in SEQ ID NO: 64, namely:

GACTAGACTAGTTCTAGAGTCGCGCCGGCGCGTCGCGACATTCTAGAGTC

TAGACGGCGCGTCTAGACTCTAGAATGCGCTTCCTGACAGTGACGCGTGC

CGATTCTAGAGGGGGTTTTCGGGGACTTTCCGGGAA

According to some embodiments, the synthetic promoter may have the sequence set forth in SEQ ID NO: 65, namely:

GACTAGACTAGTTCTAGAGTCTAGACGGCGCGGCTAGCCATTCTAGAGTC

GCGCCGGCGCGTCTAGCCTCTAGAATGCGCTTCCTGACAGTGACGCTTGC

CGATTCTAGAGGGGGTTTTCGGGGACTTTCCGGGAA

According to some embodiments, the synthetic promoter may have the sequence set forth in SEQ ID NO: 66, namely:

GACTAGACTAGTTCTAGAGGCTCGACGGCGCGTCGCGACATTCTAGAGTC

GCGACGGCGCGGCTAGACTCTAGAATGCGCTTCCTGACAGTGACGTCAGC

CGATTCTAGAGGGGGTTTTCGGGGACTTTCCGGGAA

According to some embodiments, the synthetic promoter may have the sequence set forth in SEQ ID NO: 67, namely:

GACTAGACTAGTTCTAGAGTCTAGACGGCGCGGCTAGCCATTCTAGAGTC

TAGCCGGCGCGGCGAGCCTCTAGAATTTCCCGGAAATAGGGTGGGCAAGT

ATTTCCAGGAAATTCTAGAGGGGGTTTTCGGGGACTTTCCGGGAA

According to some embodiments, the synthetic promoter may have the sequence set forth in SEQ ID NO: 68, namely:

GACTAGACTAGTTCTAGAGGCTAGCCGGCGCGTCTAGACTCTAGAATGCG

CTTCCTGACAGTGACGTTAGCCGATTCTAGAGGGGGTTTTCGGGGACTTT

CCGGGAA

According to some embodiments, the synthetic promoter may have the sequence set forth in SEQ ID NO: 69, namely:

GACTAGACTAGTTCTAGAGGCTAGACGGCGCGGCTAGCCATTCTAGAGTC

GCGACGGCGCGTCTAGACTCTAGAATTTCTCGGAAATAGGGTGGGCAAGT

ATTTCTCGGAAATTCTAGAGGGGGTTTTCGGGGACTTTCCGGGAA

According to some embodiments, the synthetic promoter may have the sequence set forth in SEQ ID NO: 70, namely:

GACTAGACTAGTTCTAGAGTCTCGACGGCGCGGCTAGCCATTCTAGAGGC

TAGACGGCGCGGCTAGCCTCTAGAATTTCTCGGAAATAGGGTGGGCAAGT

ATTTCCCGGAAATTCTAGAGGGGGTTTTCGGGGACTTTCCGGGAA

According to some embodiments, the synthetic promoter may have the sequence set forth in SEQ ID NO: 71, namely:

GACTAGACTAGTTCTAGAGGCGAGACGGCGCGTCTAGACATTCTGGCAAG

TATTTCTGGGAAATTCTAGAGGGGGTTTTCGGGGACTTTCCGGGAA

According to some embodiments, the synthetic promoter may have the sequence set forth in SEQ ID NO: 72, namely:

GACTAGACTAGTTCTAGAGTCTCGACGGCGCGTCGAGCCATTCTAGAGTC

TAGCCGGCGCGTCTAGCCTCTAGAATTTCTCGGAAATAGGGTGGGCAAGT

ATTTCTCGGAAATTCTAGAGGGGGTTTTCGGGGACTTTCCGGGAA

According to some embodiments, the synthetic promoter may have the sequence set forth in SEQ ID NO: 73, namely:

GACTAGACTAGTTCTAGAGTCTAGACGGCGCGGCGCGCCTCTAGAATGCG

CTTCCTGACAGTGACGCGAGCCGATTCTAGAGGGGGTTTTCGGGGACTTT

CCGGGAA

According to some embodiments, the synthetic promoter may have the sequence set forth in SEQ ID NO: 74, namely:

GACTAGACTAGTTCTAGAGGCGAGCCGGCGCGGCGAGCCATTCTAGAGTC

GCGACGGCGCGTCTAGCCTCTAGAATTTCCCGGAAATAGGGTGGGCAAGT

ATTTCCGGGAAATTCTAGAGGGGGTTTTCGGGGACTTTCCGGGAA

According to some embodiments, the synthetic promoter may have the sequence set forth in SEQ ID NO: 75, namely:

GACTAGACTAGTTCTAGAGTCTAGACGGCGCGTCTAGACATTCTAGAGTC

TCGACGGCGCGTCTAGACTCTAGAATTTCCCGGAAATAGGGTGGGCAAGT

ATTTCCCGGAAATTCTAGAGGGGGTTTTCGGGGACTTTCCGGGAA

According to some embodiments, the synthetic promoter may have the sequence set forth in SEQ ID NO: 76, namely:

GACTAGACTAGTTCTAGAGTCTAGACGGCGCGTCTCGACATTCTAGAGGC

GAGCCGGCGCGTCGAGACTCTAGAATTTCTCGGAAATAGGGTGGGCAAGT

ATTTCTGGGAAATTCTAGAGGGGGTTTTCGGGGACTTTCCGGGAA

According to some embodiments, the synthetic promoter may have the sequence set forth in SEQ ID NO: 77, namely:

GACTAGACTAGTTCTAGAGTCTAGCCGGCGCGTCGAGACTCTAGAATTTC

CCGGAAATAGGGTGGGCAAGTATTTCTGGGAAATTCTAGAGGGGGTTTTC

GGGGACTTTCCGGGAA

According to some embodiments, the synthetic promoter may have the sequence set forth in SEQ ID NO: 78, namely:

GACTAGACTAGTTCTAGAGTCTAGACGGCGCGGCGAGACATTCTAGAGTC

GCGCCGGCGCGTCTAGACTCTAGAATTTCTGGGAAATAGGGTGGGCAAGT

ATTTCTGGGAAATTCTAGAGGGGGTTTTCGGGGACTTTCCGGGAA

According to some embodiments, the synthetic promoter may have the sequence set forth in SEQ ID NO: 79, namely:

GACTAGACTAGTTCTAGAGTCTCGACGGCGCGTCTAGACATTCTAGAGTC

TCGCCGGCGCGTCGCGACTCTAGAATTTCCCGGAAATAGGGTGGGCAAGT

ATTTCTGGGAAATTCTAGAGGGGGTTTTCGGGGACTTTCCGGGAA

According to some embodiments, the synthetic promoter may have the sequence set forth in SEQ ID NO: 80, namely:

GACTAGACTAGTTCTAGAGTCTCGACGGCGCGTCTAGCCATTCTAGAGGC

TAGCCGGCGCGTCTCGCCTCTAGAATTTCCCGGAAATAGGGTGGGCAAGT

ATTTCTCGGAAATTCTAGAGGGGGTTTTCGGGGACTTTCCGGGAA

According to some embodiments, the synthetic promoter may have the sequence set forth in SEQ ID NO: 81, namely:

GACTAGACTAGTTCTAGAGTCGAGCCGGCGCGGCGAGACATTCTAGAGGC

GAGACGGCGCGGCTAGACTCTAGAATTTCCGGGAAATAGGGTGGGCAAGT

ATTTCTCGGAAATTCTAGAGGGGGTTTTCGGGGACTTTCCGGGAA

According to some embodiments, the synthetic promoter may have the sequence set forth in SEQ ID NO: 82, namely:

GACTAGACTAGTTCTAGAGGCTAGACGGCGCGTCGAGACTCTAGAATTTC

TGGGAAATAGGGTGGGCAAGTATTTCCCGGAAATTCTAGAGGGGGTTTTC

GGGGACTTTCCGGGAA

According to some embodiments, the synthetic promoter may have the sequence set forth in SEQ ID NO: 83, namely:

GACTAGACTAGTTCTAGAGTCTCGCCGGCGCGTCGCGCCATTCTAGAGTC

TAGACGGCGCGTCTCGCCTCTAGAATTTCTGGGAAATAGGGTGGGCAAGT

ATTTCTCGGAAATTCTAGAGGGGGTTTTCGGGGACTTTCCGGGAA

According to some embodiments, the synthetic promoter may have the sequence set forth in SEQ ID NO: 84, namely:

```
GACTAGACTAGTTCTAGAGTCGCGACGGCGCGTCTAGCCATTCTAGAGTC

TAGACGGCGCGGCTCGACTCTAGAATTTCCGGGAAATAGGGTGGGCAAGT

ATTTCCGGGAAATTCTAGAGGGGGTTTTCGGGGACTTTCCGGGAA
```

According to some embodiments, the synthetic promoter may have the sequence set forth in SEQ ID NO: 85, namely:

```
TACAGGGACAGCAGAGATCCAGTTTGGACTAGTGTTTCCGGGAAAGGGTG

GGCAAGTTTCCGGGAAAGCAGTAGGTACAGCCTTCCGGGAAAGGGTGGGC

AAGTATTTCCGGGAAATTCTAGAGGGGGTTTTCGGGGACTTTCCGGGAA
```

According to some embodiments, the synthetic promoter may have the sequence set forth in SEQ ID NO: 86, namely:

```
GACTAGACTAGTTCTAGAGTCGAGACGGCGCGTCGAGCCATTCTAG

AGGCGCGCCGGCGCGTCTAGACTCTAGAATTTCCGGGAAATAGGGT

GGGCAAGTATTTCTGGGAAATTCTAGAGGGGGTTTTCGGGGACTTT

CCGGGAA
```

According to some embodiments, the synthetic promoter may have the sequence set forth in SEQ ID NO: 87, namely:

```
GACTAGACTAGTTCTAGAGTCGAGACGGCGCGTCTAGACATTCTAG

AGGCTAGACGGCGCGTCTAGCCTCTAGAATTTCTGGGAAATAGGGT

GGGCAAGTATTTCTCGGAAATTCTAGAGGGGGTTTTCGGGGACTTT

CCGGGAA
```

According to some embodiments, the synthetic promoter may have the sequence set forth in SEQ ID NO: 88, namely:

```
TACAGGGACAGCAGAGATCCAGTTTGGACTAGTGTTTCCGGGAAAG

GGTGGGCAAGTATTTCCGGGAAATTCTAGAGGGGGTTTTCGGGGAC

TTTCCGGGAA
```

According to some embodiments, the synthetic promoter may have the sequence set forth in SEQ ID NO: 89, namely:

```
GACTAGACTAGTTCTAGAGTCGCGACGGCGCGTCGAGCCATTCTAG

AGGCTCGACGGCGCGGCGAGACTCTAGAATTTCTCGGAAATAGGGT

GGGCAAGTATTTCCGGGAAATTCTAGAGGGGGTTTTCGGGGACTTT

CCGGGAA
```

According to some embodiments, the synthetic promoter may have the sequence set forth in SEQ ID NO: 90, namely:

```
GACTAGACTAGTTCTAGAGTCTCGACGGCGCGTCTAGACATTCTAG

AGTCGAGACGGCGCGGCTAGCCTCTAGAATTTCTGGGAAATAGGGT

GGGCAAGTATTTCTCGGAAATTCTAGAGGGGGTTTTCGGGGACTTT

CCGGGAA
```

According to some embodiments, the synthetic promoter may include a hypoxia derived response element.

According to some embodiments, synthetic promoter may have the sequence set forth in SEQ ID NO: 91 (also referred to as a "consensus sequence" or "library sequence"), namely:

```
gtcgcactagttctagaGACCTTGAGTRCGTSSGTCTCTSSACGYA

TGtctaga,
wherein R = A/G, S = C/G and Y = C/T
```

According to some embodiments, synthetic promoter may have the sequence set forth in SEQ ID NO: 92 (also referred to as a "consensus sequence" or "library sequence"), namely:

```
gtcgcactagttctagaRCGTGSCTGGAGTMACAGTCCTCTTRCGT

GSCTGGAGTMACAGTCCTCTTtctaga,
wherein R = A/G, S = C/G and M = A/C.
```

According to some embodiments, the promoter response element comprises three or more promoter response elements; and wherein binding of TME factors to the three or more TME dependent promoter response elements induces a higher expression level of effector-genes than binding to two TME dependent promoter response elements.

According to some embodiments, the vector contains an indirect activation for the effector CAR/reporter by having the TME-induced promoter driving a transactivation that can enhance the expression of the CAR/reporter gene that is following a suitable promoter. For example, but not limited to, the TME-promoter may drive the expression of an rtTA-protein, and the CAR/reporter are under a TRE-promoter, thus allowing for enhancement only when an external small molecule, such as doxycycline, is provided.

According to some embodiments, the effector-gene may be, but is not limited to a CAR that comprises an antigen binding domain, a transmembrane domain, and an intracellular domain comprising a costimulatory domain and/or a primary signaling domain, wherein said antigen binding domain binds to a tumor antigen.

According to some embodiments, the vector is selected from a DNA vector, a plasmid, a lentivirus vector, an adenoviral vector, a retrovirus vector, or other vectors for introduction of the synthetic construct into immune cells.

According to some embodiments, the immune effector cell is suitable for use as a cellular immune-therapy. According to some embodiments, the engineered immune cells are suitable for anti-tumor treatments.

According to some embodiments, the ligand binding domain of the CAR is capable of specifically binding to Her2.

According to some embodiments, there is provided a method for treating cancer in a patient in need thereof, the method comprising administering immune cells comprising the expression vector as essentially described herein.

Certain embodiments of the present disclosure may include some, all, or none of the above advantages. One or more technical advantages may be readily apparent to those skilled in the art from the figures, descriptions, and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by the study of the following detailed descriptions.

BRIEF DESCRIPTION OF THE FIGURES

The patent or application file contains at least one drawing executed in color. Copies of this patent or patent application publication with color drawing(s) will be provided by the Office upon request and payment of the necessary fee.

The invention will now be described in relation to certain examples and embodiments with reference to the following illustrative figures.

FIG. 2A is a schematic drawing showing the different hypoxia element locations relative to the mini TK minimal promotor;

FIG. 3A is a schematic drawing showing of the herein disclosed G1K0.6H1 promoter;

FIG. 8A library sequences of synthetic promoters including TGF, IL-6 and TGF-β binding sites. shows representative FACS plots obtained for library screen of synthetic promoters. Variant bases were introduced within binding-sites to generate libraries with the specified sequences. Response sites for TGF-β response element are originally highlighted in green, IL-6 in yellow or pink, and TGF-β in light blue.

DETAILED DESCRIPTION

Figures 1A, 1B:
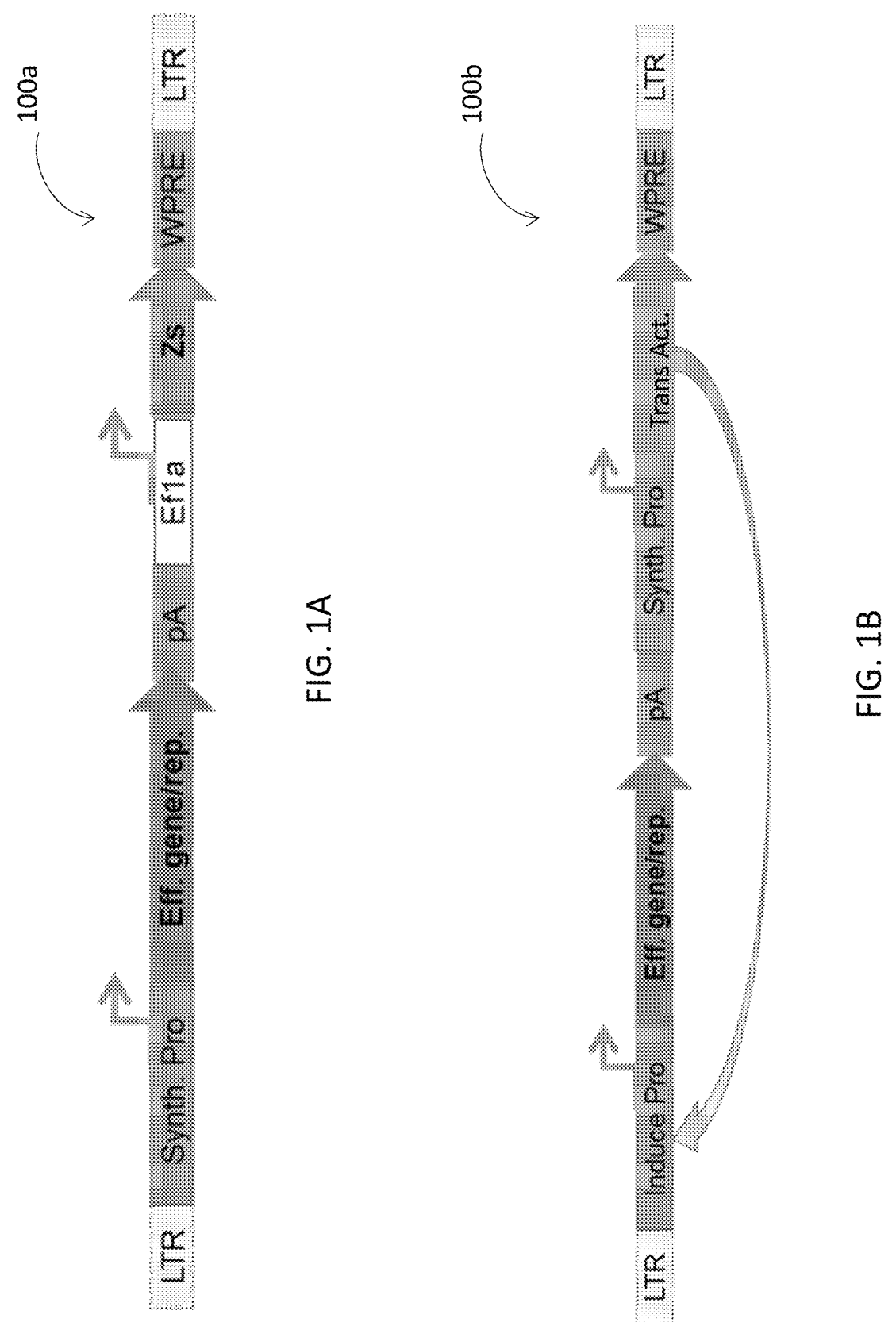
FIG. 1A schematically illustrates an expression construct comprising a synthetic promoter comprising a constitutive reporter, according to some embodiments.
FIG. 1B schematically illustrates an expression construct comprising a dual-action synthetic promoter indirectly controlling reporter or CAR gene expression.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains. According to some embodiments, the CAR may broadly refer to any moiety that is expressed by the immune cell and has a cytotoxic effect on the target cancer cell, i.e. a ligand that activates a death receptor on the target.

The terms, "tumor environment", "tumor microenvironment" and "TME" may be used interchangeably and refer to the cellular environment in which the tumor exists, including surrounding blood vessels, immune cells, fibroblasts, bone marrow-derived inflammatory cells, lymphocytes, signaling molecules and the extracellular matrix (ECM).

The term "antigen" refers to a molecule that provokes an immune response. This immune response may involve antibody production, or the activation of specific immunologically-competent cells, or both. The skilled artisan will understand that any macromolecule, including virtually all proteins or peptides, can serve as an antigen. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. It is readily apparent that an antigen can be generated synthesized or can be derived from a biological sample, or might be a macromolecule besides a polypeptide. Such a biological sample can include, but is not limited to, a tissue sample, a tumor sample, a cell or a fluid with other biological components.

The term "anti-tumor effect", refers to a biological effect which can be manifested by various means, including, but not limited to, e.g., a decrease in tumor volume, a decrease in the number of tumor cells, a decrease in the number of metastases, an increase in life expectancy, a decrease in tumor cell proliferation, a decrease in tumor cell survival, or amelioration of various physiological symptoms associated with the cancerous condition.

The term "autologous" refers to any material derived from the same individual to whom it is later to be re-introduced into the individual. The term "allogeneic" refers to any material derived from a different individual than to whom the material is introduced.

The term "conservative sequence modifications" refers to amino acid modifications that do not significantly affect or alter the binding characteristics of a factor thereto. Such conservative modifications include amino acid substitutions, additions and deletions.

As used herein, the term "Immune effector cell" refers to a cell that is involved in an immune response. Examples include various types, and sub-types of T cells, B cells, natural killer (NK) cells, Innate Lymphocyte Cells (ILCs), natural killer T (NKT) cells, Mast cells, Macrophage, Monocytes, Dendritic cells, Basophil, Neutrophils and Eosinophil.

The term "expression" refers to the transcription and/or translation of a particular nucleotide sequence driven by a promoter.

The term "expression vector" refers to a vector comprising a recombinant polynucleotide comprising expression control sequences operatively linked to a nucleotide sequence to be expressed. Expression vectors include all those known in the art, including cosmids, plasmids, episomes, transposons and viruses (e.g., lentiviruses, retroviruses, adenoviruses, and adeno-associated viruses) that incorporate the recombinant nucleotide sequences.

As used herein, the term "TME responsive expression vector" refers to an expression vector configured to express a gene product in the presence of factors constituting, defining or otherwise associated with a tumor environment.

As used herein, the term "promoter" refers to a DNA sequence recognized by the synthetic machinery of the cell, or introduced synthetic machinery, required to initiate the specific transcription of a polynucleotide sequence.

As used herein, the term "promoter/regulatory sequence" and "promoter response element (PRE)" may be used interchangeably and refer to nucleic acid sequences required for expression of a gene product operably linked to the promoter/regulatory sequence. As used herein, the term "TME factor" refers to a factor present and active in a TME such as but not limited to cytokines, transcription factors etc. As used herein, the term "PRE linked to a TME-associated factor refers to PRE that is activated following the excreted effect of the TME-associated factor. E.g "hypoxia PRE" refers to PRE that is activated following hypoxia in the TME. "IFN-γ PRE" refers to PRE that is activated following the presence of IFN-γ in the TME. In some instances, this sequence may be the core promoter sequence, and, in other instances, this sequence may also include an enhancer sequence and other regulatory elements, which are required for expression of the gene product. The promoter/regulatory sequence may, for example, be one which expresses the gene product in a tissue specific manner.

As used herein, the term "constitutive" promoter refers to a nucleotide sequence which, when operably linked with a polynucleotide encoding a gene product, causes the gene product to be produced in a cell under most or all physiological conditions of the cell.

As used herein, the term "inducible" promoter refers to a nucleotide sequence which, when operably linked with a polynucleotide encoding a gene product, causes the gene product to be substantially enhanced only when an inducer is present. "Induction" may include both the initiation of expression from an OFF state into an ON state, as well as the enhancement of expression from relative-LOW to relative-HIGH.

As used herein, the terms "TME specific promoter", "TME inducible promoter" and "TME responsive promoter" may be used interchangeably and refer to a nucleotide sequence which causes the gene product to be induced within TME.

As used herein, the terms "derived", "derivatives" and "modified" with regards to response elements may refer to response elements including at least one or at least two nucleotide substitution vis-à-vis the response element from which they are derived, as further elaborated herein.

As used herein, the term "synthetic promoter" refers to DNA sequences artificially synthesized as opposed to cloning of naturally occurring promoters.

The terms "cancer associated antigen" and "tumor antigen" may be used interchangeably and refer to a molecule (typically a protein, carbohydrate or lipid) that is expressed on the surface of a cancer cell, either entirely or as a fragment and which is useful for the preferential targeting of a pharmacological agent to the cancer cell. In some embodiments, a tumor antigen is a marker expressed by both normal cells and cancer cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell.

As used herein, the term "treating" refers to the reduction or amelioration of the progression, severity and/or duration of a proliferative disorder, or the amelioration of one or more symptoms (preferably, one or more discernible symptoms) of a proliferative disorder resulting from the treatment. In other embodiments the term refers to the inhibition of the progression of a proliferative disorder. In other embodiments, the term refers to the reduction or stabilization of tumor size or cancerous cell count. The term "transfected" refers to a process by which an exogenous nucleic acid is transferred or introduced into a host cell. The cell includes the primary subject cell and its progeny.

The terms "specifically binds" and "binding" refer to a factor such as a transcription-factor, which recognizes and binds a cognate nucleic acid sequence.

As used herein, the terms "substantially" and "essentially" with regards to the absence of gene expression in a non-tumor environment, i.e. in healthy tissue, may include no or residual expression levels only. According to some embodiments, substantially no expression (such as in healthy tissue) may refer to expression levels at levels that are biologically/functionally ineffective against normal healthy tissues, while inducing effective levels within TME.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes sub-ranges such as 96-99%, 96-98%, 96-97%, 97-99%, 97-98% and 98-99% identity. This applies regardless of the breadth of the range.

Description

According to some embodiments, there is provided a tumor environment (TME) responsive expression vector comprising a nucleic acid sequence encoding a synthetic promoter comprising two or more different TME dependent promoter response element; and a nucleic acid sequence encoding a chimeric antigen receptor. The TME responsive vector is designed such that binding of two or more different factors present in the TME to the promoter response element, directly or indirectly, induces expression of effector-genes. According to some embodiments, the two or more different factors may be unique to the TME. According to some embodiments, the two or more different factors may have an elevated expression in the TME as compared to normal tissue, According to some embodiments, the effector gene may be a CAR. According to some embodiments, the ligand binding domain of the CAR is capable of specifically binding to Her2. According to some embodiments, the vector may include the nucleotide sequence set forth in SEQ ID NO: 93.

It is understood that a trade-off may be made between including fewer response elements, so that a broad spectrum of cancers can be targeted utilizing a same TME responsive expression construct and including a more comprehensive combination of response elements increasing the specificity of the expression construct to tumor tissue as opposed to normal tissue.

According to some embodiments, the CAR is a chimeric antigen T-cell receptor (CAR-T) or a chimeric antigen Natural Killer (NK) cell receptor (CAR-NK).

According to some embodiments, the promoter response element includes/encompasses one or more interferon-gamma (IFN-γ, G)-response elements/binding sites, one or more Nuclear Factor kappa-B (NF-κB, K)-response elements/binding sites, one or more heat shock protein 70 (HSP-70) response elements/binding sites, one or more hypoxia response (H) elements/binding sites, one or more Interleukin 6 (IL-6, J) response elements/binding sites or any combination thereof. Each possibility is a separate embodiment.

According to some embodiments, the one or more TME factor may include tumor necrosis factor alpha (TNF-α), IFN-γ, IL-6, HSP-70, and/or equivalents capable of inducing similar activation pathways, or any combination thereof.

According to some embodiments, binding of TME factors to the two or more TME dependent promoter response elements induces a higher expression level of CAR than binding to a single TME dependent promoter response element. As a non-limiting example, binding of NF-κB to the NF-κ3-response elements/binding site and TNF-α to the IFN-γ-response elements/binding site of the promoter may, according to some embodiments, induce a higher expression of the CAR than binding of NF-κB or TNF-α alone.

According to some embodiments, the promoter response element comprises a nucleic acid selected from the group consisting of TTCCGGGAA set forth in SEQ ID NO. 1 (abbreviated herein as G), GGGAATTTCC set forth in SEQ ID NO. 2 (abbreviated herein as K), GACCTT-GAGTACGTGCGTCTCTGCACGTATG set forth in SEQ ID NO. 3 (abbreviated herein as H), GCGCTTCCTGACAGTGACGCGAGCCG set forth in SEQ ID NO. 4 (abbreviated herein as J), or any combination thereof. Each possibility is a separate embodiment. As a non-limiting example, the promoter response element comprises twice the nucleic acid sequence TTCCGGGAA set forth in SEQ ID NO. 1 (abbreviated G2). As another non-limiting example, the promoter response element comprises both the nucleic acid sequence TTCCGGGAA set forth in SEQ ID NO. 1 and the nucleic acid sequence GGGAATTTCC set forth in SEQ ID NO. 2 (abbreviated G1K1). According to some embodiments, the nucleic acids may be coextensive. As a non-limiting example, the nucleic acid sequence GACCTT-GAGTACGTGCGTCTCTGCACGTATG set forth in SEQ ID NO. 3 may be immediately followed by the nucleic acid sequence GCGCTTCCTGACAGTGACGCGAGCCG set forth in SEQ ID NO. 4 (abbreviated H1J1. According to some embodiments, the nucleic acids may be separated by a spacer sequence. As a non-limiting example, the nucleic acid sequence TTCCGGGAA set forth in SEQ ID NO. 1 and the nucleic acid sequence GGGAATTTCC set forth in SEQ ID NO. 2 may be spaced apart by a spacer element within the same synthetic promoter.

According to some embodiments, the TME responsive expression vector further includes a nucleic acid sequence encoding an externally inducible promoter and a nucleic acid sequence encoding a trans-activator, e.g. rtTA3. According to some embodiments, the synthetic promoter drives expression of the trans-activator and the inducible promoter drives expression of the CAR. According to some embodiments, only the combined presence of the external inducer and the TME factor results in CAR expression. According to some embodiments, the presence of the external inducer in the absence of TME factor, causes substantially no induction of CAR expression. According to some embodiments, the presence of the external inducer in the absence of TME factor, causes minimal induction of CAR expression. According to some embodiments, when the TME factor binds the promoter response element in the absence of the external inducer, essentially no CAR expression is induced. According to some embodiments, a minor level of CAR expression is also found in the un-induced state. Such minimal expression may serve to ensure that CAR-T memory is maintained.

According to some embodiments, the inducible promoter may be a Tet-Response-Element promoter, and the external inducer may be doxycycline and/or tetracycline. According to some embodiments, the Tet-Response-Element may be activated by the combined presence of the trans-activator and doxycycline and/or tetracycline. The tetracycline (Tet)-On system is an inducible gene expression system for mammalian cells, in which the reverse Tet transactivator (rtTA) fusion protein, which is composed of the doxycycline-binding Tet-repressor mutant protein and the C-terminal activator domain from the herpes simplex virus VP16 protein, is engineered to control gene expression by providing doxycycline (Dox). In the presence of Dox, rtTA activates a minimal promoter that is fused downstream of an array (e.g. seven) repeated Tet-operator sequences. Until recently, all Tet-On systems had required two separate vectors, one to introduce rtTA and another with the inducible promoter to control the gene of interest. However, a one-vector system has recently been developed, which has enabled transduction of a gene of interest into primary immune cells. By utilizing this one-vector system, it is possible to control target expression and functions using the Tet-On inducible system.

According to some embodiments, the CAR molecule encoded by the CAR sequence comprises an antigen binding domain, a transmembrane domain, and an intracellular domain, optionally comprising a costimulatory domain and/or a primary signaling domain. According to some embodiments, the antigen binding domain binds to a tumor antigen. Non-limiting examples of tumor antigens include: thyroid stimulating hormone receptor (TSHR); CD171; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(]-4)bDGlcp(l-l)Cer); Tn antigen (Tn Ag); Fms-Like Tyrosine Kinase 3 (FLT3); CD38; CD44v6; B7H3 (CD276); KIT (CD117); Interleukin-13 receptor subunit alpha-2 (IL-13Ra2); Interleukin 11 receptor alpha (IL-1 1Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); epidermal growth factor receptor (EGFR); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Fucosyl GM1; sialyl Lewis adhesion molecule (sLe); ganglioside GM3 (aNeu5Ac(2-3)bDGalp (1-4)bDGlcp(1-1)Cer; TGS5; high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1), Her2 and any combination thereof. Each possibility is a separate embodiment.

According to some embodiments, the TME responsive expression vector further comprises effector-genes encoding a protein (or functional RNA) that enhance penetration of the immune effector cell into the tumor, such as, but not limited to, proteases of the MMP8/9.

According to some embodiments, the TME responsive expression vector further comprises one or more effector-genes encoding miRNAs that suppress immune-inhibitors, such as, but not limited to, PD1 and/or CTLA4, within the tumor.

According to some embodiments, the TME responsive expression vector further comprises one or more effector-genes encoding cytokines bringing about immune-cell retention within the tumor, such as, but not limited to, CXCL9/10 and/or CRCR3 ligands, thereby generating an autocrine loop.

According to some embodiments, the vector may be any suitable vector allowing expression in mammalian cells, such as human cells. According to some embodiments, the vector may be selected from a DNA vector, an RNA vector, a plasmid, a lentivirus vector, an adenoviral vector, or a retrovirus vector. Each possibility is a separate embodiment.

According to some embodiments, a TME vector library may be created, which library includes TME vectors, each having a unique TME responsive expression element profile.

According to some embodiments, there is provided an immune effector cell or cell population comprising the herein disclosed tumor environment (TME) responsive expression vector. According to some embodiments, the immune effector cell or cell population is an NK cell or a T-cell.

According to some embodiments, there is provided a method for treating cancer in a patient in need thereof, the method comprising administering an effective amount of an immune effector cell comprising the herein disclosed tumor environment (TME) responsive expression vector.

According to some embodiments, the method further comprises administrating to the patient an external inducer, such as, but not limited to, tetracycline and/or doxycycline. According to some embodiments, the external inducer may be provided before, concurrently with, or after the administration of the immune effector cell having the herein disclosed tumor environment (TME) responsive expression vector.

According to some embodiments, the method may include a step of evaluating CAR expression levels and/or checking the patient for adverse effects.

According to some embodiments, the CAR expression levels may be evaluated before administering the external inducer. According to some embodiments, the CAR expression levels may be evaluated, during and/or after administrating the external inducer. As a non-limiting example, a first bolus of external inducer may be initially given, followed by an evaluation of CAR expression. A second bolus may then be administered based on the CAR expression level detected and the patient's response to the treatment. According to some embodiments, the external inducer may be provided repeatedly, for example every 10 hours, every day, every two days or any other suitable time interval. According to some embodiments, the administering of the external inducer may be terminated if adverse effects are detected. According to some embodiments, the amount of external inducer administered may be increased/decreased based on the evaluated CAR expression levels and/or based on the patient's response to the treatment.

According to some embodiments, there is provided a method for screening a patient for determination of an optimal synthetic promoter for CAR expression. The method includes obtaining a biopsy of a patient's tumor, determining the expression profile of one or more TME factors in the biopsy; and selecting and/or engineering a TME responsive expression vector having a TME dependent promoter response element matching the expression profile of the one or more TME factors in the biopsy. According to some embodiments, the TME may be expressed by the tumor cells and/or by non-tumor TME cells. According to some embodiments, the non-tumor TME cells may be the immune effector cells.

According to some embodiments, a tissue sample obtained from the patient's tumor and optionally also from healthy tissue may be grown in-vitro and a library of TME-responsive vectors and may be used to screen for the vector proving most effective and selective for treatment, namely a vector having a TME response profile matching that of the tumor. This to obtain maximum expression in tumor tissue, while also being unique to the tumor, so that no or minimal expression is obtained in healthy tissue.

According to some embodiments, the method further includes introducing the selected TME responsive expression vector into an immune effector cell or cell population. According to some embodiments, the immune effector cell or cell population is an NK cell or a T-cell. According to some embodiments, the immune effector cell or cell population is autologous to the patient. According to some embodiments, the immune effector cell or cell population are isolated from the patient prior to the treatment.

According to some embodiments, the method further includes administering the immune effector cell or cell population to the patient.

Reference is now made to FIG. 1A which schematically illustrates an expression construct 100a comprising a synthetic promoter comprising a constitutive reporter, according to some embodiments.

The vector includes:
3rd generation SIN-LTR (Self-Inactivating Long Terminal Repeats—LTR),
a synthetic promoter (Synth. Pro.) as disclosed herein;
an effector gene e.g. a CAR or a reporter (Eff. gene/rep.);
poly-Adenylation (pA).
an independent constitutive promoter (Ef1a) driving a infection reporter (Zs),
woodchuck posttranscriptional regulatory element (WPRE) that stabilizes the RNA.

Reference is now made to FIG. 1B which schematically illustrates an expression construct 100b comprising a dual action synthetic promoter indirectly activating an effector gene, according to some embodiments. This design provides both an enhancement for the effector gene expression as well as an additional layer of control, as the Trans-Activator may require an exogenous co-factor (e.g. Doxycycline not shown).

The vector includes:
3rd generation SIN-LTR (Self-Inactivating Long Terminal Repeats—LTR), followed by promoter (Synth. Pro.);

an inducible promoter (e.g. such as tet-responsive-pro-
moter—Induce Pro) at drives the effector gene (Eff.
gene/rep);
poly-Adenylation (pA);
a synthetic promoter (CARTIV) as disclosed herein that is 5
driving expression of a Trans-Activator (such as
rtTA—Trans. Act.);
woodchuck posttranscriptional regulatory element
(WPRE) that stabilizes the RNA.

The following examples are presented in order to more 10
fully illustrate some embodiments of the invention. They
should in no way be construed, however, as limiting the
broad scope of the invention. One skilled in the art can readily devise many variations and modifications of the
principles disclosed herein without departing from the scope
of the invention.

EXAMPLES

Example 1: Defining Response Elements

Promoters, including the following response elements
sequences, are listed in Table 1 below. The response ele-
ments were constructed just before a minimal transcription
promoter with a TATAA box that can initiate expression with
adequate proximal elements.

TABLE 1

| Promoter response element sequences | | | |
|---|---|---|---|
| Abbre-viation | Response elements | Sequence | SEQ ID NO. |
| K1 | 1xNF-κB | GGGAATTTCCGGGGACTTTCCGGGAATT TCCGGGGACTTTCCGGGAATTTCCAGAG CATATTAAGGTGACGCGTGTGGCCTCGA ACACCGAGCGACCCTGCAGCGACCCGC TTAAAAGCGGCCGCC | SEQ ID NO. 5 |
| G2 | 2xIFN-γ | TTCCGGGAAAGGGTGGGCAAGTTTCCG GGAAAGCAGTAGGTACAGCCTTCCGGG AAAGGGTGGGCAAGTTTCCGGGAAAGC AGTAGGTTTTTCGCATATTAAGGTGACG CGTGTGGCCTCGAACACCGAGCGACCCT GCAGCGACCCGCTTAAAAGGCGCGCC | SEQ ID NO. 6 |
| G4 | 4xIFN-γ | TTCCGGGAAAGGGTGGGCAAGTTTCCG GGAAAGCAGTAGGTACAGCCTTCCGGG AAAGGGTGGGCAAGTTTCCGGGAAAGC AGTAGGTACAGCCTTCCGGGAAAGGGT GGGCAAGTTTCCGGGAAAGCAGTAGGT ACAGCCTTCCGGGAAAGGGTGGGCAAG TTTCCGGGAAAGCAGTAGGTTTTTCGCA TATTAAGGTGACGCGTGTGGCCTCGAAC ACCGAGCGACCCTGCAGCGACCCGCTT AAAAGGCGCGCC | SEQ ID NO. 7 |
| G6 | 6xIFN-γ | TTCCGGGAAAGGGTGGGCAAGTTTCCG GGAAAGCAGTAGGTACAGCCTTCCGGG AAAGGGTGGGCAAGTTTCCGGGAAAGC AGTAGGTACAGCCTTCCGGGAAAGGGT GGGCAAGTTTCCGGGAAAGCAGTAGGT ACAGCCTTCCGGGAAAGGGTGGGCAAG TTTCCGGGAAAGCAGTAGGTACAGCCTT CCGGGAAAGGGTGGGCAAGTTTCCGGG AAAGCAGTAGGTACAGCCTTCCGGGAA AGGGTGGGCAAGTTTCCGGGAAAGCAG TAGGTTTTTCGCATATTAAGGTGACGCG TGTGGCCTCGAACACCGAGCGACCCTGC AGCGACCCGCTTAAAAGGCGCGCC | SEQ ID NO. 8 |
| G1K1 | 1xIFN-γ + 1xNF-κB | TTCCGGGAAAGGGTGGGCAAGTTTCCG GGAACCCGGGAATTTCCGGGGACTTTCC GGGAATTTCCGGGGACTTTCCGGGAATT TCCAGAGCATATTAAGGTGACGCGTGTG GCCTCGAACACCGAGCGACCCTGCAGC GACCCGCTTAAAAGCGGCCGCC | SEQ ID NO. 9 |
| G1K0.6 | 1xIFN-γ + 60% NF-κB | TTCCGGGAAAGGGTGGGCAAGTTTCCG GGAACCCGGGAATTTCCGGGGACTTTCC GGGAATTTCCAGAGCATATTAAGGTGA CGCGTGTGGCCTCGAACACCGAGCGAC CCTGCAGCGACCCGCTTAAAAGCGGCC GCC | SEQ ID NO. 10 |
| G2K2 | 2xIFN-γ + 2xNF-κB | TTCCGGGAAAGGGTGGGCAAGTTTCCG GGAAAGCAGTAGGTACAGCCTTCCGGG AAAGGGTGGGCAAGTTTCCGGGAAAGA GCAGGGAATTTCCGGGGACTTTCCGGG AATTTCCGGGGACTTTCCGGGAATTTCC AGAGCAGGGAATTTCCGGGGACTTTCC | SEQ ID NO. 11 |

TABLE 1-continued

| Promoter response element sequences | | | |
| --- | --- | --- | --- |
| Abbre-viation | Response elements | Sequence | SEQ ID NO. |
| | | GGGAATTTCCGGGGACTTTCCGGGAATT TCCAGAGCATATTAAGGTGACGCGTGTG GCCTCGAACACCGAGCGACCCTGCAGC GACCCGCTTAAAAGGCGCGCC | |
| G3K3 | 3xIFN-γ + 3xNF-κB | TTCCGGGAAAGGGTGGGCAAGTTTCCG GGAAAGCAGTAGGTACAGCCTTCCGGG AAAGGGTGGGCAAGTTTCCGGGAAAGC AGTAGGTACAGCCTTCCGGGAAAGGGT GGGCAAGTTTCCGGGAAAGAGCAGGGA ATTTCCGGGGACTTTCCGGGAATTTCCG GGGACTTTCCGGGAATTTCCAGAGCAG GGAATTTCCGGGGACTTTCCGGGAATTT CCGGGGACTTTCCGGGAATTTCCAGAGC AGGGAATTTCCGGGGACTTTCCGGGAAT TTCCGGGGACTTTCCGGGAATTTCCAGA GCATATTAAGGTGACGCGTGTGGCCTCG AACACCGAGCGACCCTGCAGCGACCCG CTTAAAAGGCGCGCC | SEQ ID NO. 12 |
| G3H2K3 | 3xIFN-γ + 2xhypoxia + 2xNF-κB | TTCCGGGAAAGGGTGGGCAAGTTTCCG GGAAAGCAGTAGGTACAGCCTTCCGGG AAAGGGTGGGCAAGTTTCCGGGAAAGC AGTAGGTACAGCCTTCCGGGAAAGGGT GGGCAAGTTTCCGGGAAAGCAGTAGGT ACAGCCGACCTTGAGTACGTGCGTCTCT GCACGTATGAGAGCAGACCTTGAGTAC GTGCGTCTCTGCACGTATGAGAGCAGG GAATTTCCGGGGACTTTCCGGGAATTTC CGGGGACTTTCCGGGAATTTCCAGAGCA GGGAATTTCCGGGGACTTTCCGGGAATT TCCGGGGACTTTCCGGGAATTTCCAGAG CAGGGAATTTCCGGGGACTTTCCGGGA ATTTCCGGGGACTTTCCGGGAATTTCCA GAGCATATTAAGGTGACGCGTGTGGCCT CGAACACCGAGCGACCCTGCAGCGACC CGCTTAAAAGGCGCGCC | SEQ ID NO. 13 |
| G3K3H2 | 3xIFN-γ + 3xNF-κB + 2xhypoxia | TTCCGGGAAAGGGTGGGCAAGTTTCCG GGAAAGCAGTAGGTACAGCCTTCCGGG AAAGGGTGGGCAAGTTTCCGGGAAAGC AGTAGGTACAGCCTTCCGGGAAAGGGT GGGCAAGTTTCCGGGAAAGAGCAGGGA ATTTCCGGGGACTTTCCGGGAATTTCCG GGGACTTTCCGGGAATTTCCAGAGCAG GGAATTTCCGGGGACTTTCCGGGAATTT CCGGGGACTTTCCGGGAATTTCCAGAGC AGGGAATTTCCGGGGACTTTCCGGGAAT TTCCGGGGACTTTCCGGGAATTTCCAGA GCAGACCTTGAGTACGTGCGTCTCTGCA CGTATGAGAGCAGACCTTGAGTACGTG CGTCTCTGCACGTATGAGAGCATATTAA GGTGACGCGTGTGGCCTCGAACACCGA GCGACCCTGCAGCGACCCGCTTAAAAG GCGCGCC | SEQ ID NO. 14 |
| G2H2K2 | 2xIFN-γ + 2xhypoxia + 2xNF-κB | TTCCGGGAAAGGGTGGGCAAGTTTCCG GGAAAGCAGTAGGTACAGCCTTCCGGG AAAGGGTGGGCAAGTTTCCGGGAAAGC AGTAGGTACAGCCGACCTTGAGTACGT GCGTCTCTGCACGTATGAGAGCAGACCT TGAGTACGTGCGTCTCTGCACGTATGAG AGCAGGGAATTTCCGGGGACTTTCCGG GAATTTCCGGGGACTTTCCGGGAATTTC CAGAGCAGGGAATTTCCGGGGACTTTCC GGGAATTTCCGGGGACTTTCCGGGAATT TCCAGAGCATATTAAGGTGACGCGTGTG GCCTCGAACACCGAGCGACCCTGCAGC GACCCGCTTAAAAGGCGCGCC | SEQ ID NO. 15 |
| G2K2H2 | 2xIFN-γ + 2xNF-κB + 2xhypoxia | TTCCGGGAAAGGGTGGGCAAGTTTCCG GGAAAGCAGTAGGTACAGCCTTCCGGG AAAGGGTGGGCAAGTTTCCGGGAAAGA GCAGGGAATTTCCGGGGACTTTCCGGG AATTTCCGGGGACTTTCCGGGAATTTCC | SEQ ID NO. 16 |

TABLE 1-continued

| | | Promoter response element sequences | |
|---|---|---|---|
| Abbre-viation | Response elements | Sequence | SEQ ID NO. |
| | | AGAGCAGGGAATTTCCGGGGACTTTCC GGGAATTTCCGGGGACTTTCCGGGAATT TCCAGAGCAGACCTTGAGTACGTGCGTC TCTGCACGTATGAGAGCAGACCTTGAGT ACGTGCGTCTCTGCACGTATGAGAGCAT ATTAAGGTGACGCGTGTGGCCTCGAAC ACCGAGCGACCCTGCAGCGACCCGCTT AAAAGGCGCGCC | |
| H2G2K2 | 2xhypoxia + 2xIFN-γ + 2xNF-κB | GACCTTGAGTACGTGCGTCTCTGCACGT ATGAGAGCAGACCTTGAGTACGTGCGT CTCTGCACGTATGAGAGCATTCCGGGAA AGGGTGGGCAAGTTTCCGGGAAAGCAG TAGGTACAGCCTTCCGGGAAAGGGTGG GCAAGTTTCCGGGAAAGAGCAGGGAAT TTCCGGGGACTTTCCGGGAATTTCCGGG GACTTTCCGGGAATTTCCAGAGCAGGG AATTTCCGGGGACTTTCCGGGAATTTCC GGGGACTTTCCGGGAATTTCCAGAGCAT ATTAAGGTGACGCGTGTGGCCTCGAAC ACCGAGCGACCCTGCAGCGACCCGCTT AAAAGGCGCGCC | SEQ ID NO. 17 |
| G1H2K1 | 1xIFN-γ + 2xhypoxia + 1xNF-κB | TTCCGGGAAAGGGTGGGCAAGTTTCCG GGAAAGCAGTAGGTACAGCCGACCTTG AGTACGTGCGTCTCTGCACGTATGAGAG CAGACCTTGAGTACGTGCGTCTCTGCAC GTATGAGAGCAGGGAATTTCCGGGGAC TTTCCGGGAATTTCCGGGGACTTTCCGG GAATTTCCAGAGCATATTAAGGTGACGC GTGTGGCCTCGAACACCGAGCGACCCT GCAGCGACCCGCTTAAAAGGCGCGCC | SEQ ID NO. 18 |
| G1J1H1 | 1xIFN-γ + 1xIL-6 + 1xhypoxia | TTCCGGGAAAGGGTGGGCAAGTTTCCG GGAACCCGACCTTGAGTACGTGCGTCTC TGCACGTATGTACAGCGCTTCCTGACAG TGACGCGAGCCGAGAGCATATTAAGGT GACGCGTGTGGCCTCGAACACCGAGCG ACCCTGCAGCGACCCGCTTAAAAGCGG CCGCC | SEQ ID NO. 19 |
| G1K0.6J1 | 1xIFN-γ + 60% NF-κB + 1xIL-6 | TTCCGGGAAAGGGTGGGCAAGTTTCCG GGAACCCGGGAATTTCCGGGGACTTTCC GGGAATTTCCTACAGCGCTTCCTGACAG TGACGCGAGCCGAGAGCATATTAAGGT GACGCGTGTGGCCTCGAACACCGAGCG ACCCTGCAGCGACCCGCTTAAAAGCGG CCGCC | SEQ ID NO. 20 |
| G1K0.6H1 | 1xIFN-γ + 60% NF-κB + 1xhypoxia | TTCCGGGAAAGGGTGGGCAAGTTTCCG GGAACCCGGGAATTTCCGGGGACTTTCC GGGAATTTCCTACAGACCTTGAGTACGT GCGTCTCTGCACGTATGAGAGCATATTA AGGTGACGCGTGTGGCCTCGAACACCG AGCGACCCTGCAGCGACCCGCTTAAAA GCGGCCGCC | SEQ ID NO. 21 |

Table 2 below provides the sequences of promoters providing optimal CAR expression profile.

TABLE 2

| | promoter sequences |
|---|---|
| SEQ ID NO. | Sequence |
| 22 | TACAGGGACAGCAGAGATCCAGTTTGGACTAGCCCGGTCGCAC TAGTTCTAGAACTTCCCGGAAATAGGGTGGGCAAGTATTTCCG GGAAATTCTAGAGGGAGTTCCCGGGGACTTTCCGGGGGATTTTC TCTAGATATTAAGGTGACGCGTGTGGCCTCGAACACCGAGCGA |

TABLE 2-continued

| | promoter sequences |
|---|---|
| SEQ ID NO. | Sequence |
| | CCCTGCAGCGACCCGCTTAAAAGCGGCCGCCATGGGCCGCCAT GGCCTCCTCCGAGGACGTCATCAAGGAGTTCATGC |
| 23 | TACAGGGACAGCAGAGATCCAGTTTGGACTAGCCCGGTCGCAC TAGTTCTAGAACTTCCCGGAAGTAGGGTGGGCAAGTACTTCCC GGAAGTTCTAGAGGAAATTTTCGGGGACTTTCCGGGGGTTCTC TCTAGATATTAAGGTGACGCGTGTGGCCTCGAACACCGAGCGA |

TABLE 2-continued promoter sequences

| SEQ ID NO. | Sequence |
|---|---|
| | CCCTGCAGCGACCCGCTTAAAAGCGGCCGCCATGGGCCGCCAT<br>GGCCTCCTCCGAGGACGTCATCAAGGAGTTCATGC |
| 24 | TACAGGGACAGCAGAGATCCAGTTTGGACTAGCCCGGTCGCAC<br>TAGTTCTAGAACTTCCCGGAAGTAGGGTGGGCAAGTACTTCCG<br>GGAAATTCTAGAGGGAGTTCTCGGGGACTTTCCGGGAATTTTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 25 | TACAGGGACAGCAGAGATCCAGTTTGGACTAGCCCGGTCGCAC<br>TAGTTCTAGAACTTCCCGGAAGTAGGGTGGGCAAGTATTTCCC<br>GGAAGTTCTAGAGGAAGTTCTCGGGGACTTTCCGGAGATTCTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 26 | TACAGGGACAGCAGAGATCCAGTTTGGACTAGCCCGGTCGCAC<br>TAGTTCTAGAACTTCCGGGAAATAGGGTGGGCAAGTACTTCCG<br>GGAAATTCTAGAGGGGATTTCCGGGGACTTTCCGGAGGTTCTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 27 | TACAGGGACAGCAGAGATCCAGTTTGGACTAGCCCGGTCGCAC<br>TAGTTCTAGAACTTCCGGGAAATAGGGTGGGCAAGTACTTCCG<br>GGAAGTTCTAGAGGAGGTTTTCGGGGACTTTCCGGAGGTTTCC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 28 | TACAGGGACAGCAGAGATCCAGTTTGGACTAGCCCGGTCGCAC<br>TAGTTCTAGAACTTCCGGGAAGTAGGGTGGGCAAGTATTTCCC<br>GGAAGTTCTAGAGGGGGTTTTCGGGGACTTTCCGGAGGTTTCC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 29 | TACAGGGACAGCAGAGATCCAGTTTGGACTAGCCCGGTCGCAC<br>TAGTTCTAGAACTTCCGGGAAGTAGGGTGGGCAAGTATTTCCG<br>GGAAATTCTAGAGGGAGTTCTCGGGGACTTTCCGGGGATTTTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 30 | TACAGGGACAGCAGAGATCCAGTTTGGACTAGCCCGGTCGCAC<br>TAGTTCTAGAATTTCCCGGAAATAGGGTGGGCAAGTACTTCCG<br>GGAAATTCTAGAGGGGGTTTCCGGGGACTTTCCGGGGGTTTTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 31 | TACAGGGACAGCAGAGATCCAGTTTGGACTAGCCCGGTCGCAC<br>TAGTTCTAGAATTTCCCGGAAATAGGGTGGGCAAGTATTTCCC<br>GGAAATTCTAGAGGGGGTTTTCGGGGACTTTCCGGGAATTTTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 32 | TACAGGGACAGCAGAGATCCAGTTTGGACTAGCCCGGTCGCAC<br>TAGTTCTAGAATTTCCCGGAAATAGGGTGGGCAAGTATTTCCG<br>GGAAATTCTAGAGGAGGTTCTCGGGGACTTTCCGGGAGTTTTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 33 | TACAGGGACAGCAGAGATCCAGTTTGGACTAGCCCGGTCGCAC<br>TAGTTCTAGAATTTCCCGGAAATAGGGTGGGCAAGTATTTCCG<br>GGAAATTCTAGAGGAGGTTTTCGGGGACTTTCCGGGAGTTTCC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 34 | TACAGGGACAGCAGAGATCCAGTTTGGACTAGCCCGGTCGCAC<br>TAGTTCTAGAATTTCCCGGAAATAGGGTGGGCAAGTATTTCCG |

| SEQ ID NO. | Sequence |
|---|---|
| | GGAAGTTCTAGAGGAAGTTTTCGGGGACTTTCCGGGAATTTTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 35 | TACAGGGACAGCAGAGATCCAGTTTGGACTAGCCCGGTCGCAC<br>TAGTTCTAGAATTTCCGGGAAATAGGGTGGGCAAGTATTTCCC<br>GGAAGTTCTAGAGGAGATTCTCGGGGACTTTCCGGGGGTTCTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 36 | TACAGGGACAGCAGAGATCCAGTTTGGACTAGCCCGGTCGCAC<br>TAGTTCTAGAATTTCCGGGAAGTAGGGTGGGCAAGTACTTCCG<br>GGAAATTCTAGAGGGGGTTTCCGGGGACTTTCCGGAGATTCTC<br>TCTAGATATTAAGGTGACGCGTGTGGCCTCGAACACCGAGCGA<br>CCCTGCAGCGACCCGCTTAAAAGCGGCCGCCATGGGCCGCCAT<br>GGCCTCCTCCGAGGACGTCATCAAGGAGTTCATGC |
| 37 | TACAGGGACAGCAGAGATCCAGTTTGGACTAGCCCGGTCGCAC<br>TAGTTCTAGAATTTCCGGGAAATAGGGTGGGCAAGTATTTCCC<br>GGAAGTTCTAGAGGGGGTTTTCGGGGACTTTCCGGAAATTTTC<br>TCTAGATATTAAGGTGACGCGTGTGGCCTCGAACACCGAGCGA<br>CCCTGCAGCGACCCGCTTAAAAGCGGCCGCCATGGGCCCCATG<br>GCCTCCTCCGAGGACGTCATCAAGGAGTTCATGC |
| 38 | TACAGGGACAGCAGAGATCCAGTTTGGACTAGCCCGGTCGCAC<br>TAGTTCTAGAACTTCCCGGAAATAGGGTGGGCAAGTATTTCCC<br>GGAAGTTCTAGAGGAGGTTTTCGGGGACTTTCCGGGATTCCCT<br>CTAGATATTAAGGTGACGCGTGTGGCCTCGAACACCGAGCGAC<br>CCTGCAGCGACCCGCTTAAAAGCGGCCGCCATGGGCCGCCATG<br>GCCTCCTCCGAGGACGTCATCAAGGAGTTCATGC |
| 39 | TACAGGGACAGCAGAGATCCAGTTTGGACTAGCCCGGTCGCAC<br>TAGTTCTAGTTCCGGGAAGTGGGTGGGCAATATTTCCCGGAAG<br>TTTAGAGGAAGTTTTCGGGGACTTCCGGAAATTCCCTCTAGAT<br>ATTAAGGTGACGCGTGTGGCCTCGAACACCGAGCGACCCTGCA<br>GCGACCCGCTTAAAAGCGGCCGCCATGGGCCGCCATGGCCTCC<br>TCCGAGGACGTCATCAAGGAGTTCATGC |
| 40 | TACAGGGACAGCAGAGATCCAGTTTGGACTAGCCCGGTCGCAC<br>TAGTTCTAGAACTTCTCGGAAATAGGGTGGGCAAGTACTGTGG<br>CCTCGAACACCGAGCGACCCTGCAGCGACCCGCTTAAAAGCGG<br>CCGCCATGGGCCGCCATGGCCTCCTCCGAGGACGTCATCAAGG<br>AGTTCATGCAGACCAAGTCTCTGCTACC |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

Example 2: The Hypoxia PRE is Most Potent when Upstream to the Minimal Promotor

Figures 2B, 2C:
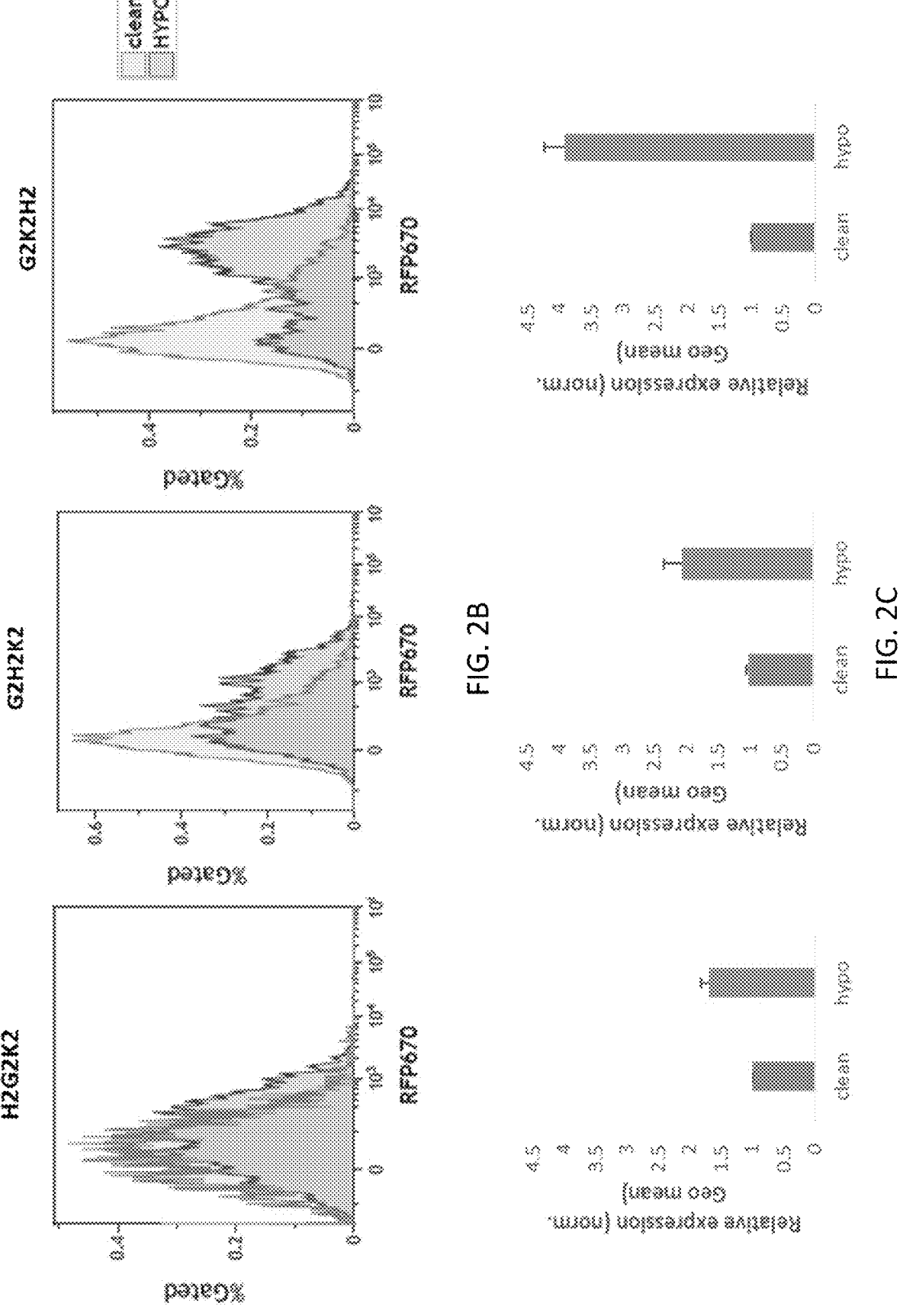
FIG. 2B shows representative plots of HEK293T cells that were infected using lentiviral vectors with RFP670 under the expression of the indicated promotor. 72 hours following infection, cells were placed for 18 hours under hypoxic conditions, harvested and analyzed by flow cytometry.
FIG. 2C shows histogram plots of FIG. 2B.

3-PRE synthetic promoters based on the G-PRE, K-PRE and Hypoxia (H)-PRE were designed as outlined in FIG. 2A corresponding to SEQ ID NOs. 17, 15 and 16, respectively. The reason for testing these promoters was assessing the effect of distance from the promoter and relative positioning to the GK elements. The hypoxia PRE in natural promoters is known to be located at enhancer regions, that can be thousands of bases upstream or downstream from the Transcription Start Site (TSS), have the same response potency—independently of its distance to the. The inclusion of Hypoxia-Response-Elements within the proximal promoter, together with other PREs was therefore not expected to be sensitive to any specific order. Unexpectedly, the best response to the hypoxia stimulus was obtained when the H-PRE was located downstream to the GK PREs and near the minimal promoter (mini TK); this is shown in FACS histograms (FIG. 2B) and in Bar graphs showing the normalized intensity of fluorescence geometric mean (FIG. 2C).

Figures 3B, 3C:
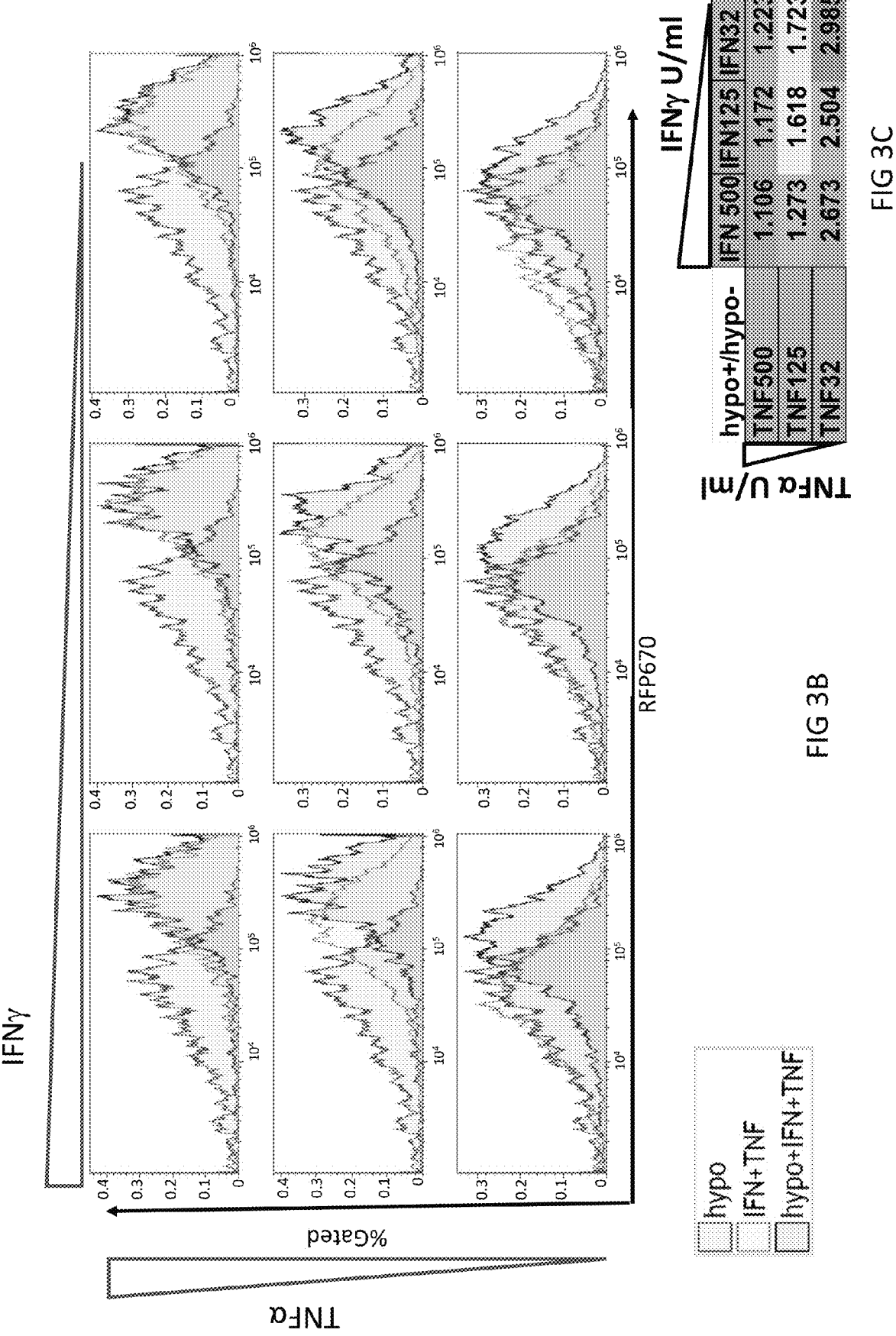
FIG. 3B shows representative FACS plots of HEK293T cells that were infected using lentiviral vectors with RFP670 under the expression of the G1K0.6H1 promoter. 72 hours following infection, cells were placed for 48 hours in titrated cytokine concentrations (32.5 (bottom panels for TNF and right panels for IFN, 125 or 500 U/ml (top panels for TNF and left panels for IFN)) and for 18 hours under hypoxia (hypo—originally pink), or IFN and TNF (IFN+TNF—originally orange) and hypoxiam IFN and TNF (hypo+IFN+TNF—originally purple), harvested and analyzed by flow cytometry.
FIG. 3C shows a quantification table of FIG. 3B.

Example 3: The G1K0.6H1 Promotor Response to Hypoxia and Cytokines in Titrated Cytokine Concentrations Since G1K0.6 showed a synergism in a 2-PRE+2 stimuli model we aimed to further test the addition of hypoxia PRE to G1K0.6 (SEQ ID NO: 21) and downstream to these elements, as per the results of FIG. 2B and FIG. 2C. We then tested the effect of the hypoxia stimulus in addition to IFNγ and TNFα and we investigate it in titrated cytokine amounts more resembling (at the lower range of 32.5 u/ml) the physiological levels of these cytokines. The results described in the histogram data (FIG. 3A) and the normalized data (FIG. 3B) demonstrate that the hypoxia stimulus synergizes with the cytokine stimuli at the lower levels of cytokines stimuli which resemble the physiological concentrations of these cytokines.

Example 4: G1K0.6 Promotor Response in Human Primary T-Cells and NK92 Cells

Figure 4A:
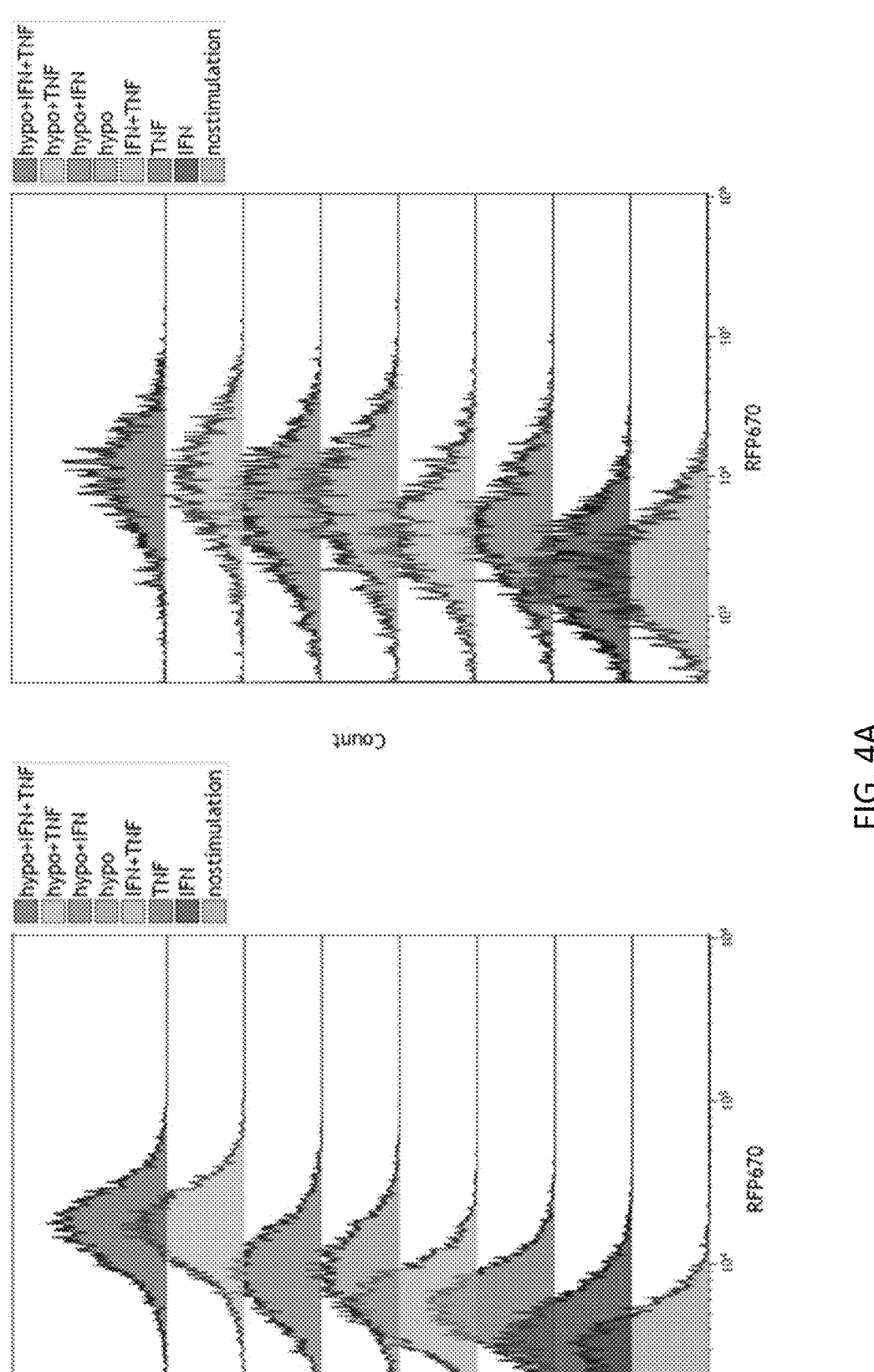
FIG. 4A shows representative FACS plots of human primary NK92 cells (left panel) and T cells (right panel), infected using lentiviral vectors with RFP670 under the expression of the indicated G1K0.6H1 promoter. At least 72 hours following infection cells were incubated for 48 hours in 250 U/mL and for 18 hours under hypoxic or normoxic conditions and under exposure to the indicated cytokines (top down), harvested and analyzed by flow cytometry.
Figure 4B:
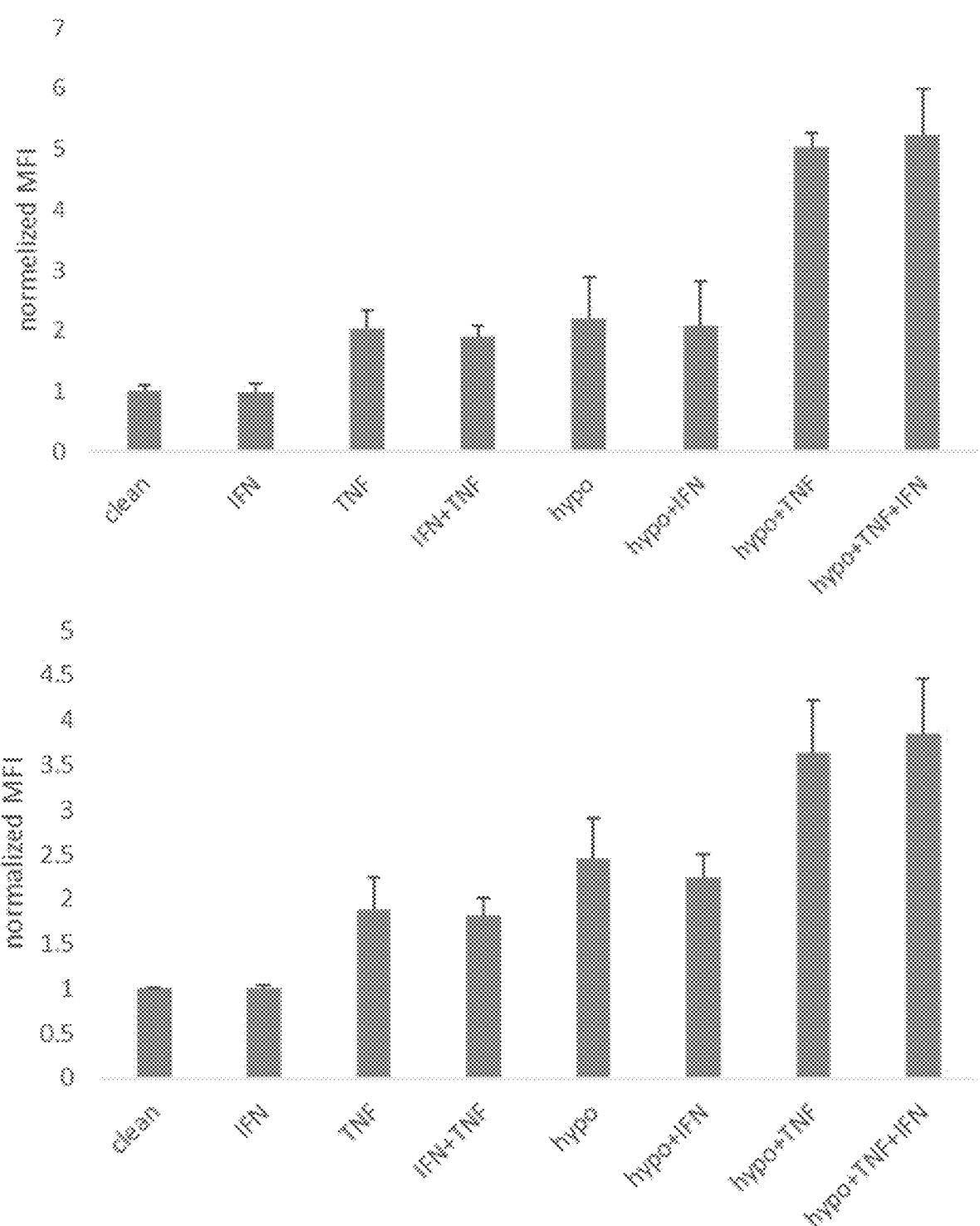
FIG. 4B shows histogram plots of FIG. 4A (top panel NK cells, lower panel T-cells)
Figure 4C:
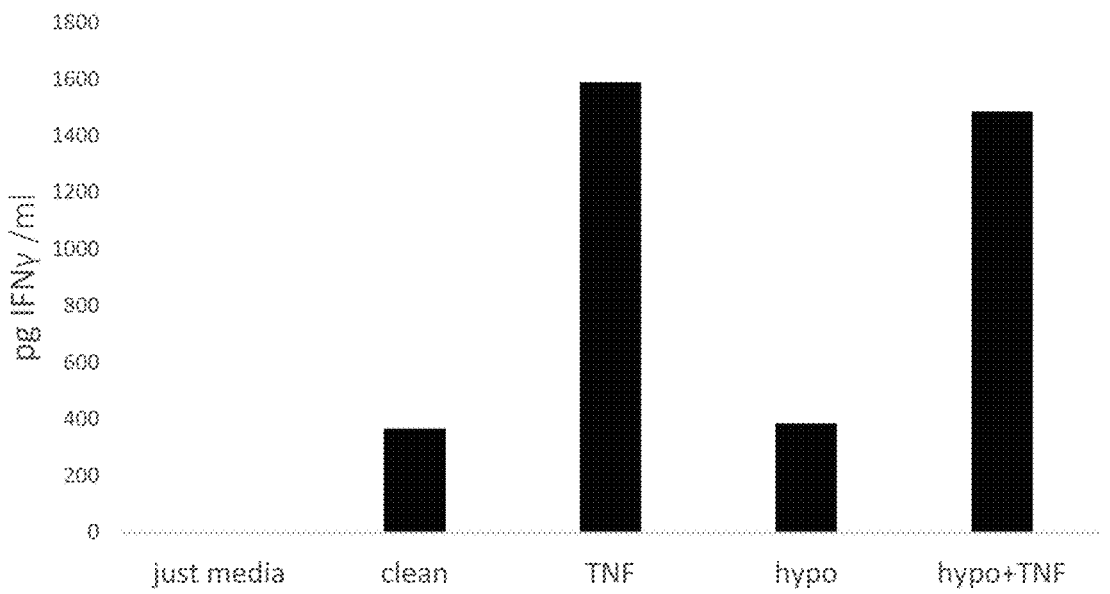
FIG. 4C shows IFNγ ELISA results obtained when testing the supernatant of human primary T cells incubated for 48 hours in 250 U/mL of the indicated cytokines and for 18 hours under hypoxic or normoxic condition.

Following the proof that the 3-PRE G1K0.6H1 synthetic promoter is a synergizing promoter for HEK293T cells, we further investigated this promoter with human effector NK and T cells that are the candidate cells to be transduced by this promoter in the clinic. FIG. 4A shows the FACS histograms of the G1K0.6H1 response to stimuli in human NK (NK92) and primary Human T cells, while FIG. 4B shows the normalized fluorescence intensity. It seems that exogenous IFNγ stimulus does not affect the induction by the promoter, which is in line with the fact that NK and T cells secrete endogenous IFNγ. It is however clear that the combination of TNFα and hypoxia (with or without exogenous IFNγ) synergize the effect of the single stimulus of TNFα or of Hypoxia (FIG. 4A, FIG. 4B).

Figure 5A:
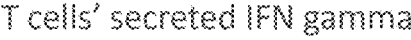
FIG. 5A is a schematic depiction of the herein disclosed Her2-CAR.
Figure 5B:
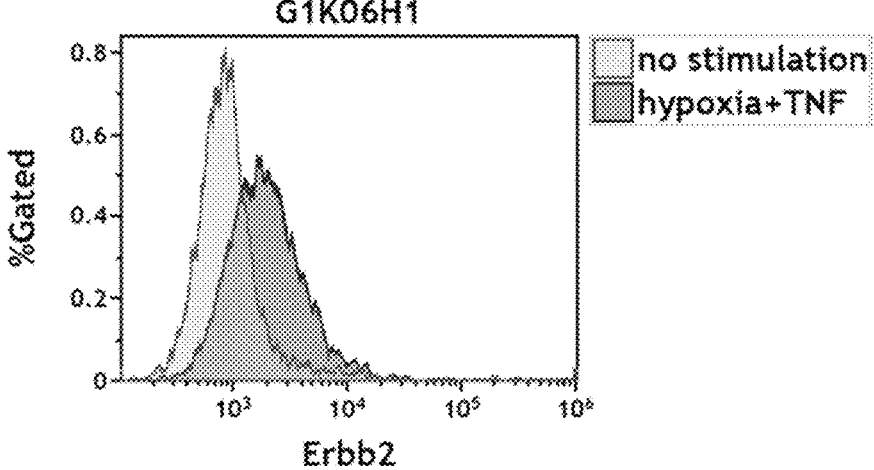
FIG. 5B shows representative FACS plots of human T cells incubated for 48 hours in 250 U/mL of the indicated cytokines and for 18 hours under hypoxic or normoxic conditions and then stained using Erbb2-Fc (Her2) chimeric protein.
Figure 5C:
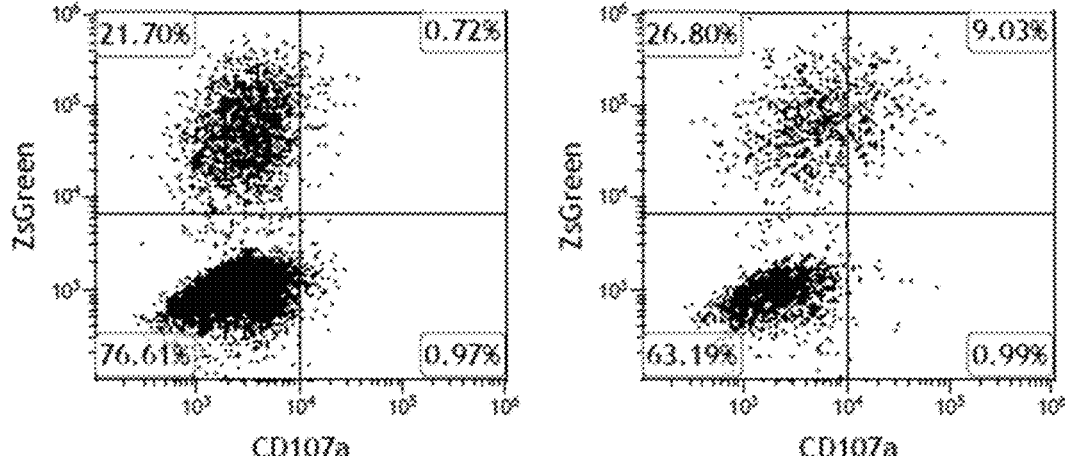
FIG. 5C shows representative FACS plots of human primary T cells (JIMT1 and HEK293T) incubated for 48 hours in 250 U/mL of TNFα and for 18 hours under hypoxic conditions and subsequently incubated for 4 hours with TNFα and hypoxia stimulated T cells or non-stimulated T cells in a 5:1 effector-target ratio in the presence of anti-human CD107a APC.
Figure 5C:
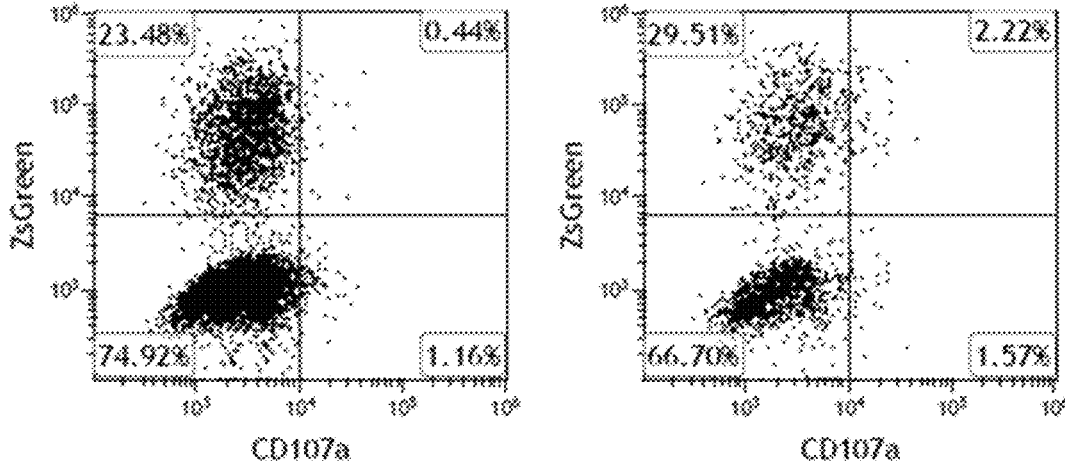

Example 5: T-Cell Activations in Her2 Expressing Cells Following Induced Her2-Car Expression We then aimed to test the 3-PRE G1K0.6H1 synthetic promoter encoding for Her2-CAR. We chose the Herceptin-based CAR (3rd generation, set forth in SEQ ID NO: 42 and outlined in FIG. 5A). Primary human T cells were transduced with the G1K0.6H1-Her2-CAR vector including the nucleotide sequence set forth in SEQ ID NO: 93. Expression of CAR on the T cell membrane following stimuli with TNFα and hypoxia as compared to T cells not exposed to stimuli was then tested. As seen from FIG. 5B expression of Her2-CAR (erbb2) was observed following the stimuli. The functionality was further demonstrated by the fact that the transduced primary T cells, following stimulation with TNFα and hypoxia, were activated in JIMT1 cells (9.03%— see FIG. 5C upper right panel), which express HER2 (the ligand for Her2-CAR, Tanner M1 et al., Mol Cancer Ther. 2004 December; 3(12):1585-92.), while only a dull activation (2.22%, see FIG. 5C lower right panel) was observed in HEK293T target cells, which do not express HER2. Furthermore, essentially no activation was observed in the absence of stimulation in both cell lines (0.72% and 0.44% respectively, see FIG. 5C, left panels).

Example 6: The G1K06H1 Promotor is Selective Induced in Tumor Tissue

Figure 6A:
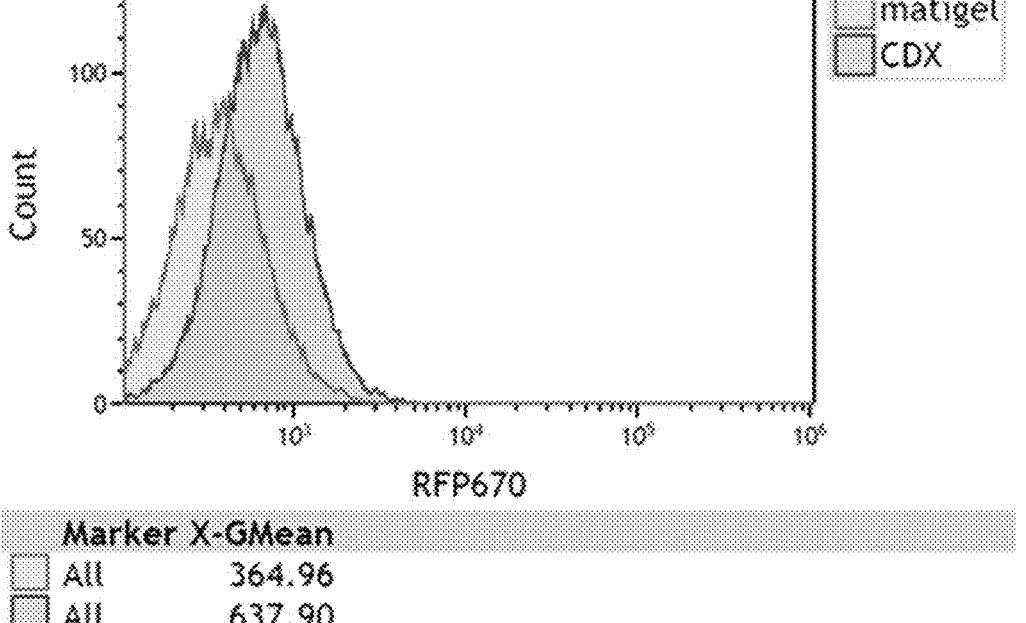
FIG. 6A shows representative FACS plots obtained from the following experiment: NK92 ($5\times10^6$) cells that were infected using lentiviral vectors with RFP670 under the G1K06H1 promotor were intratumorally injected (CDX—originally red) or subcutaneously into the flank in Matrigel (representing non-tumor tissue—originally green). 48 hours post injection mice were sacrificed, tumors mechanically and enzymatically digested to create single cell suspension and analyzed by FACS for reporter gene expression.
Figure 6B:
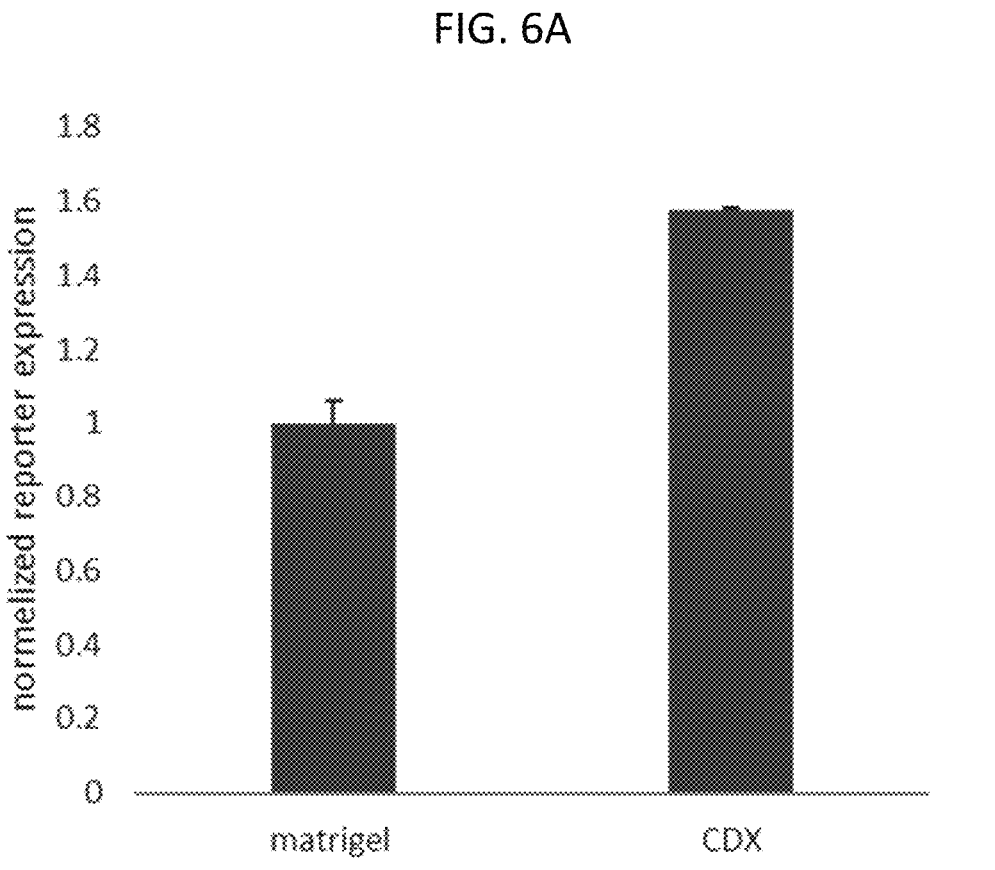
FIG. 6B shows a histogram plot of FIG. 6A.
Figure 6C:
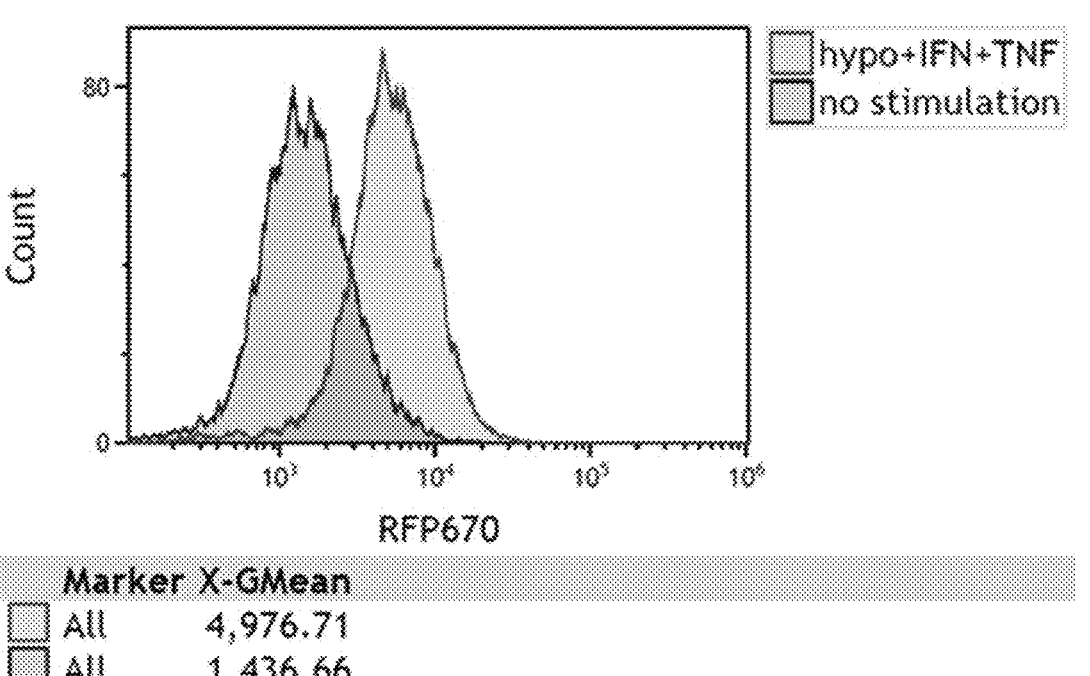
FIG. 6C shows representative FACS plots obtained from the following experiment: NK92 ($5\times10^6$) cells that were infected using lentiviral vectors with RFP670 under the G1K06H1 promotor were either stimulated in vitro by hypoxia IFN and TNF or left untreated and reporter gene expression tested by FACS.
Figure 6D:
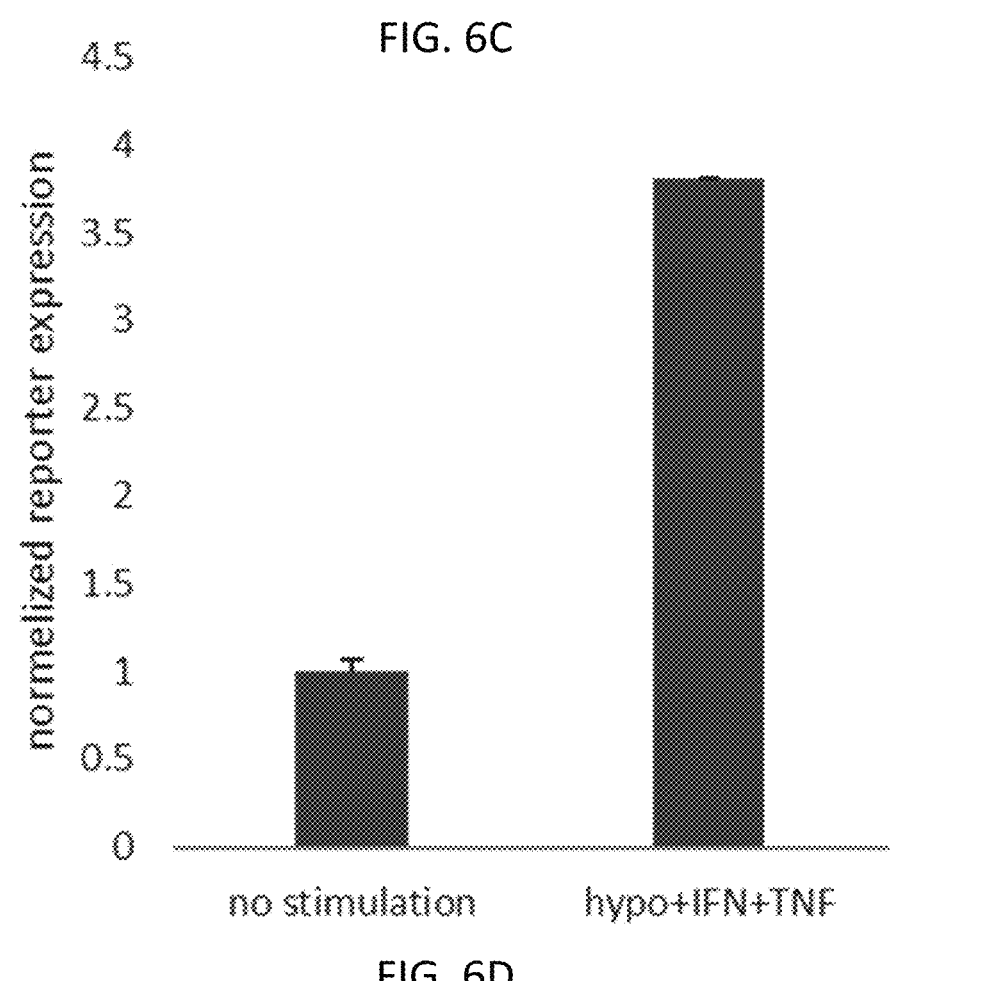
FIG. 6D shows a histogram plot of FIG. 6C.
Figure 7A:
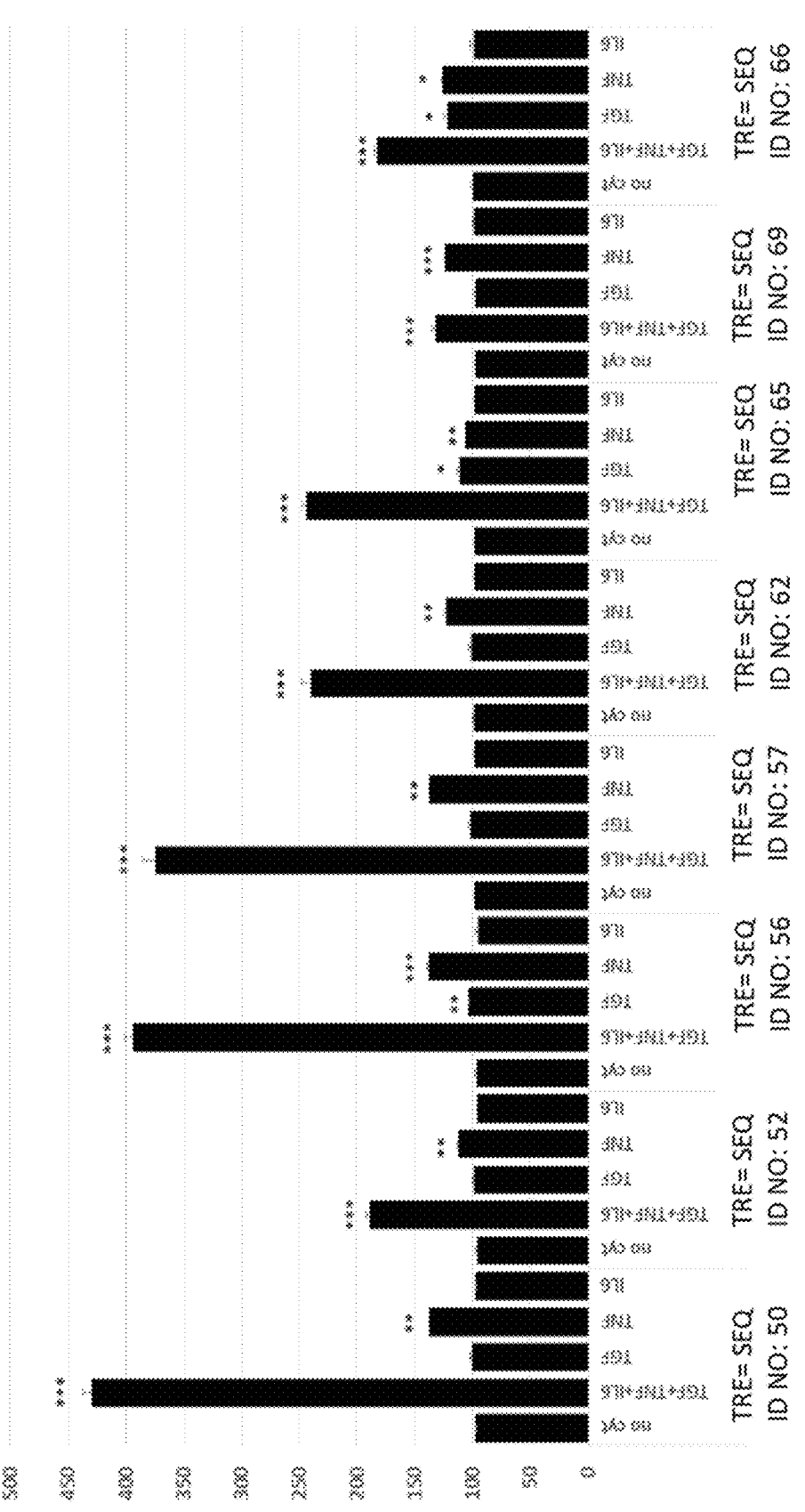
FIG. 7A shows representative histogram of HEK293 cells infected using lenti-viral vectors with RFP670 under the expression of synthetic promoters including the indicated promoter sequence and ZsGreen under an ef1α core promotor. At least 72 hours following infection cells were incubated for 48 hours in 200 U/mL, harvested and analyzed by flow cytometry. Data shown is ZsGreen positive, single discriminated and DAPI negative.
Figure 7B:
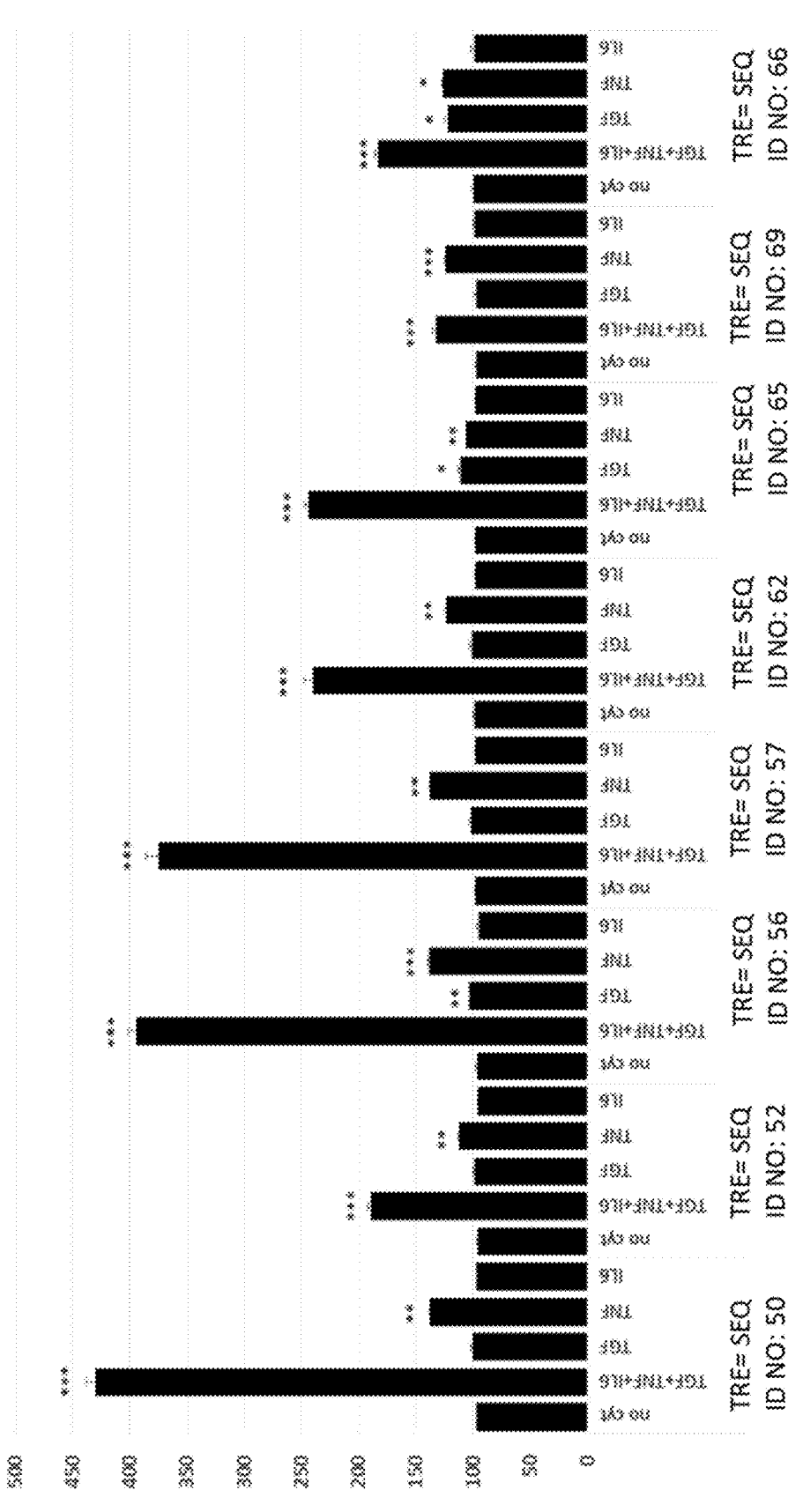
FIG. 7B shows representative histogram of HEK293 cells infected using lenti-viral vectors with RFP670 under the expression of synthetic promoters including the indicated promoter sequence and ZsGreen under an ef1α core promotor. At least 72 hours following infection cells were incubated for 48 hours in 200 U/mL, harvested and analyzed by flow cytometry. Data shown is ZsGreen positive, single discriminated and DAPI negative.

The G1K0.6H1 synthetic promoter was further tested for its ability to be selectively induced in vivo in TME as compared to non-TME environments. NK92 human NK cells were transduced with the G1K0.6H1 synthetic promoter encoding for a fluorescence reporter gene were injected intra-tumorally or intra-matrigel (representing non-tumor TME) in the same mouse. FIG. 6A shows that T cells within the tumor were induced in vivo to express the reporter gene as compared to T cells inoculated in vivo into a Matrigel in a non-tumor tissue of the same mouse. FIG. 7B shows the same results when normalized and done for a group of tumors and matrigel-bearing mice, inoculated with the G1K0.6H1-reporter transduced primary human T cells. Differences were statistically significant.

Example 7: Response Element Synergism

HEK293 cells were infected using lenti-viral vectors with RFP670 under the expression of the indicated CARTIV promotor and ZsGreen under an eflα core promotor. At least 72 hours following infection cells were incubated for 48 hours in 200 U/mL, harvested and analyzed by flow cytometry. Data shown is ZsGreen positive, single discriminated and DAPI negative. As seen from FIG. 7A and FIG. 7B a synergistic induction was observed for ell synthetic promoters, in particular significant synergism was observed for promoters including the sequences set forth in SEQ ID NO: 50, 51, 56, 57, 62, 65 and 66.

Example 8: Synthetic CARTIV-Promoter Libraries for Optimizing Response Element Efficiency Binding cites of defined response elements (TGF-β, TNF-α, IL-6 and hypoxia) were modified by substituting nucleotides in specific points of interest, thereby generating libraries with specified "consensus" sequences, as set forth in SEQ ID NOs: 53-55, 91 and 92. The sequences of three synthetic promoters including TGF-β (originally green), IL-6 (yellow or pink) and/or TNF-α (blue) response elements are illustratively depicted in FIG. 8A. Advantageously, the libraries enable identifying optimized CARTIV promoters with improved/varying induction of gene expression, thereby increasing the dynamic range of effector gene induction.

Example 9: Functional Screen of Synthetic-Promoter Libraries

Figure 8A:
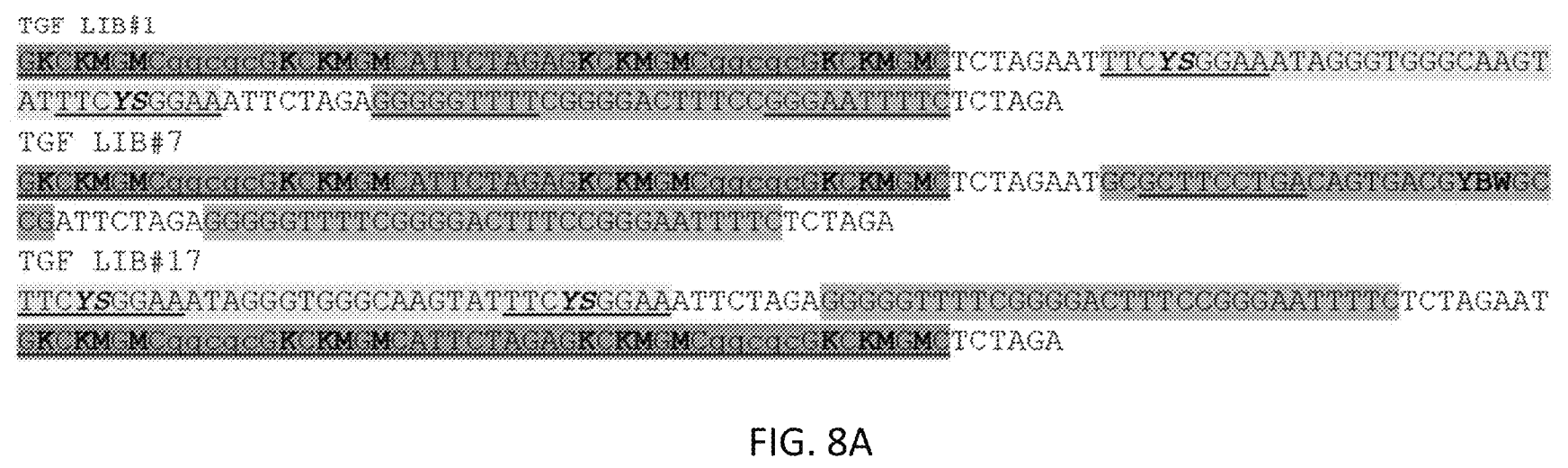
Figure 8B:
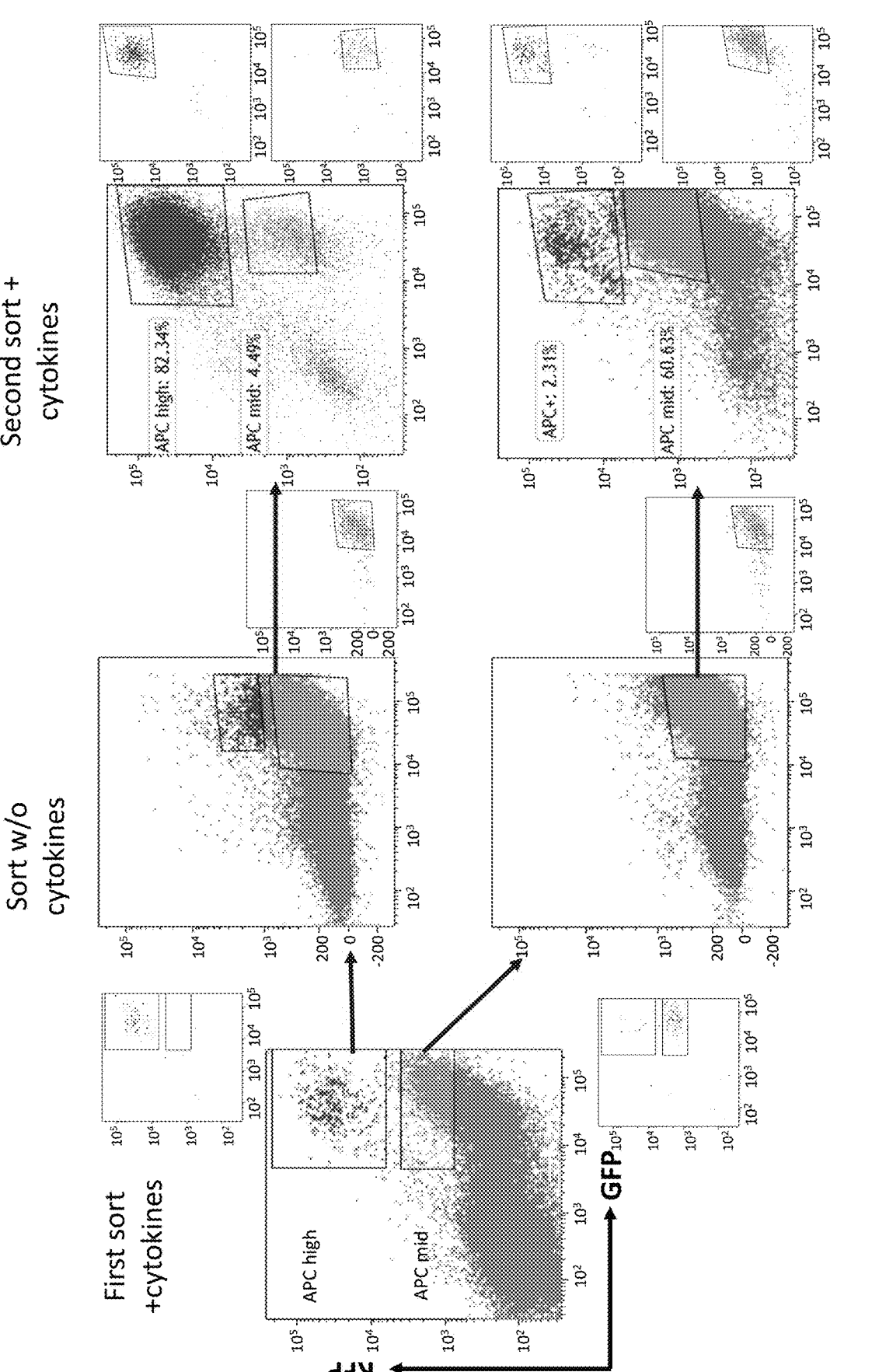
FIG. 8B shows representative FACS sorting of HEK293 cells infected with library-lenti viral vectors having ZsGreen under an Ef1α core promoter (indicate of infection), and RFP670 indicating cytokine induced-expression. Initially cells having either high RFP expression (APC high—originally red dots) or medium RFP expression (APC mid—originally green dots) in response to cytokine exposure (+cytokine) were gated. Next, the sorted cells were grow in absence of cytokines (– cytokines) and once again sorted for low RFP expression (indicative of promoter shut-off in absence of cytokines). Subsequently, the double sorted cells were once again exposed to cytokines and cells capable once again inducing RFP were sorted. The smaller FACS-plots inserts show re-analysis of each sort.

HEK293 cells were infected with the library-lenti viral vectors including the synthetic consensus promoters shown in FIG. 8A. The vectors included ZsGreen under an Ef1α constitutive promotor (serving as a marker of infection), and RFP670 under the modified CARTIV promoter. Importantly, having the constitutive ZsGreen reporter allowed careful titration of the initial transduction rate to be below 30% and limit the likelihood of multiple-LVs in one cell. The cells underwent FACS sorting, the results of which are shown in FIG. 8B: Initially cells were stimulated with cytokines and sorted for their ability to positively-respond, high RFP expression (APC high—originally red dots) or medium RFP expression (APC mid—originally green dots) were gained. The purity of the sorting was verified for each population as shown in the small plots.

Next, the sorted cells were grow in absence of cytokines (– cytokines) and once again sorted—but this time for their ability to shut-off expression. Accordingly, ZsGreen+RFP-low cells were sorted, in order to identify promoters which, in the absence of the cytokines (simulating TME), are turned off (middle panel).

Subsequently, cells were further grown with cytokines and sorted once again, this time selecting for promoters that can turn-on again after having been shut off.

The cells were analyzed, and then expanded once more to gain genomic DNA for sequencing. 34 novel sequences were selected from these libraries (set forth in SEQ ID NO: 56-90).

Example 10: Validation of Novel Synthetic CARTIV Promoters Identified from Libraries Screening The identified sequences were selected by their enrichment following FACS sorting (as described in Example 9). These are re-synthesized and cloned into lenti-viral constructs for independent validation.

---

The invention claimed is:

1. A Tumor Micro-Environment (TME) responsive expression vector comprising:
   a nucleic acid sequence encoding a synthetic promoter, said promoter comprising two or more different TME dependent promoter response elements (PRE)s; and
   a nucleic acid sequence encoding an effector gene,
   wherein said TME responsive expression vector is designed such that binding of two or more TME factors present in the TME to the PREs induces expression of the effector-gene, and in the absence of binding of the two or more TME factors to the PREs essentially no effector gene is expressed; and wherein the two or more different PREs comprise at least one TGF-β derived PRE having the nucleotide sequence set forth in SEQ ID NO: 48 and at least one response element other than a TGF-β derived PRE.

2. The TME responsive expression vector of claim 1, wherein the at least one TME dependent PRE other than a TGF-β derived PRE is selected from the list consisting of: interferon-gamma-(IFN-γ) PRE, TGF-β PRE, Nuclear Factor kappa-B (NF-κB) PRE, hypoxia PRE, Heat shock protein 70 (HSP-70) PRE, IL-6 PRE, IL-1 PRE, IL-8 PRE, IL-11 PRE, IL-12 PRE, IL-15 PRE, IL-18 PRE, IL-17 PRE, IL-21 PRE, IL-35 PRE, GM-CSF PRE, Hepatic Growth Factor (HGF) PRE, Aryl Hydrogen Receptor (AhR) PRE or any combination thereof, activated within an inflammatory TME.

3. The TME responsive expression vector of claim 1, wherein the at least one TME dependent PRE other than a TGF-β derived PRE is selected from an NF-κB PRE, an IL-6 PRE, an IL-6 derived PRE, and an IFN-γ PRE.

4. The TME responsive expression vector of claim 3, wherein the IL-6 derived PRE has a nucleotide sequence set forth in SEQ ID NO: 49 or 52.

5. The TME responsive expression vector of claim 1, wherein the synthetic promoter comprises at least two TGF-β derived response elements.

6. The TME responsive expression vector of claim 1, wherein the synthetic promoter comprises a consensus nucleotide sequence set forth in any one of SEQ ID NO: 53-55.

7. The TME responsive expression vector of claim 1, wherein the two or more different TME dependent PREs comprise a TGF-β derived PRE, a Nuclear Factor kappa-B (NF-κB) PRE, and an hypoxia PRE.

8. The TME responsive expression vector of claim 7, wherein the hypoxia PRE is downstream of the TGF-β derived PRE and the Nuclear Factor kappa-B (NF-κB) PRE.

9. The TME responsive expression vector of claim 7, wherein the synthetic promoter comprises a nucleic acid sequence having at least 80% sequence homology to a nucleic acid selected from the nucleic acid sequences set forth in SEQ ID Nos 1-40 or any combination thereof.

10. The TME responsive expression vector of claim 9, wherein the synthetic promoter comprises a nucleic acid sequence having at least 80% sequence homology to a nucleic acid sequence set forth in SEQ ID NO: 21.

11. The TME responsive expression vector of claim 1, wherein binding of two or more TME factors to the two or more different TME dependent PREs induces a higher expression level of the effector gene than binding to a single TME dependent PRE.

12. The TME responsive expression vector of claim 1, wherein the vector is selected from a DNA vector, a plasmid, a lentivirus vector, an adenoviral vector, or a retrovirus vector.

13. The TME responsive expression vector of claim 1, wherein the effector gene is a chimeric antigen receptor (CAR) capable of specifically binding to Her2 (CAR-Her2).

14. The TME responsive expression vector of claim 13, comprising the nucleotide sequence set forth in SEQ ID NO: 93.

15. An immune effector cell comprising the TME responsive expression vector of claim 1.

16. The immune effector cell of claim 15, wherein the tumor is a solid tumor.

17. The immune effector cell of claim 15, wherein the effector gene is a chimeric antigen receptor (CAR) capable of specifically binding to Her2 (CAR-Her2).

18. The TME responsive expression vector of claim 1, wherein the two or more different PREs comprise a TGF-$\beta$ derived PRE, a Nuclear Factor kappa-B (NF-$\kappa$B) PRE, and an IL-6 PRE.

* * * * *

SEQUENCE LISTING

```
<160> NUMBER OF SEQ ID NOS: 93

<210> SEQ ID NO 1
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)..(10)
<223> OTHER INFORMATION: n = a, t, c or g

<400> SEQUENCE: 1 ttccgggaan                                                         10

<210> SEQ ID NO 2
<211> LENGTH: 10
<212> TYPE: DNA
<213> ORGANISM: Artificial Sequence
<220> FEATURE:
<223> OTHER INFORMATION: Synthetic sequence

<400> SEQUENCE: 2
gggaatttcc                                                         10

<210> SEQ ID NO 3
<211> LENGTH: 31
<212> TYPE: DNA
<213> ORGANISM: Artificial Sequence
<220> FEATURE:
<223> OTHER INFORMATION: Synthetic sequence

<400> SEQUENCE: 3
gaccttgagt acgtgcgtct ctgcacgtat g                                 31

<210> SEQ ID NO 4
<211> LENGTH: 26
<212> TYPE: DNA
<213> ORGANISM: Artificial Sequence
<220> FEATURE:
<223> OTHER INFORMATION: Synthetic sequence

<400> SEQUENCE: 4
gcgcttcctg acagtgacgc gagccg                                       26

<210> SEQ ID NO 5
<211> LENGTH: 126
<212> TYPE: DNA
<213> ORGANISM: Artificial Sequence
<220> FEATURE:
<223> OTHER INFORMATION: Syntetic sequence
```

-continued

```
<400> SEQUENCE: 5
gggaatttcc gggactttc cgggaatttc cgggactttt ccgggaattt ccagagcata      60
ttaaggtgac gcgtgtggcc tcgaacaccg agcgaccctg cagcgacccg cttaaaagcg     120
gccgcc                                                                126

<210> SEQ ID NO 6
<211> LENGTH: 163
<212> TYPE: DNA
<213> ORGANISM: Artificial Sequence
<220> FEATURE:
<223> OTHER INFORMATION: Synthetic sequence

<400> SEQUENCE: 6
ttccgggaaa gggtgggcaa gtttccggga aagcagtagg tacagccttc cgggaaaggg      60
tgggcaagtt tccgggaaag cagtaggttt ttcgcatatt aaggtgacgc gtgtggcctc     120
gaacaccgag cgaccctgca gcgacccgct aaaaggcgc gcc                        163

<210> SEQ ID NO 7
<211> LENGTH: 257
<212> TYPE: DNA
<213> ORGANISM: Artificial Sequence
<220> FEATURE:
<223> OTHER INFORMATION: Synthetic promoter

<400> SEQUENCE: 7
ttccgggaaa gggtgggcaa gtttccggga aagcagtagg tacagccttc cgggaaaggg      60
tgggcaagtt tccgggaaag cagtaggtac agccttccgg gaaagggtgg gcaagtttcc     120
gggaaagcag taggtacagc cttccgggaa agggtgggca gtttccggg aaagcagtag      180 gtttttcgca tattaaggtg acgcgtgtgg cctcgaacac cgagcgaccc tgcagcgacc     240
cgcttaaaag gcgcgcc                                                    257

<210> SEQ ID NO 8
<211> LENGTH: 351
<212> TYPE: DNA
<213> ORGANISM: Artificial Sequence
<220> FEATURE:
<223> OTHER INFORMATION: Synthetic sequence

<400> SEQUENCE: 8
ttccgggaaa gggtgggcaa gtttccggga aagcagtagg tacagccttc cgggaaaggg      60
tgggcaagtt tccgggaaag cagtaggtac agccttccgg gaaagggtgg gcaagtttcc     120
gggaaagcag taggtacagc cttccgggaa agggtgggca gtttccgggg aaagcagtag     180
gtacagcctt ccgggaaagg gtgggcaagt ttccgggaaa gcagtaggta cagccttccg     240
ggaaagggtg ggcaagtttc cgggaaagca gtaggttttt cgcatattaa ggtgacgcgt     300
gtggcctcga acaccgagcg accctgcagc gacccgctta aaggcgcgc c               351

<210> SEQ ID NO 9
<211> LENGTH: 160
<212> TYPE: DNA
<213> ORGANISM: Artificial Sequence
<220> FEATURE:
<223> OTHER INFORMATION: Synthetic sequence

<400> SEQUENCE: 9
ttccgggaaa gggtgggcaa gtttccggga acccgggaat tccggggac tttccgggaa       60 tttccgggga ctttccggga atttccagag catattaagg tgacgcgtgt ggcctcgaac     120
```

```
accgagcgac cctgcagcga cccgcttaaa agcggccgcc                           160

<210> SEQ ID NO 10
<211> LENGTH: 139
<212> TYPE: DNA
<213> ORGANISM: Artificial Sequence
<220> FEATURE:
<223> OTHER INFORMATION: Synthetic sequence

<400> SEQUENCE: 10
ttccgggaaa gggtgggcaa gtttccggga acccgggaat ttccggggac tttccgggaa    60
tttccagagc atattaaggt gacgcgtgtg gcctcgaaca ccgagcgacc ctgcagcgac   120
ccgcttaaaa gcggccgcc                                                 139

<210> SEQ ID NO 11
<211> LENGTH: 267
<212> TYPE: DNA
<213> ORGANISM: Artificial Sequence
<220> FEATURE:
<223> OTHER INFORMATION: Synthetic sequence

<400> SEQUENCE: 11
ttccgggaaa gggtgggcaa gtttccggga aagcagtagg tacagccttc cgggaaaggg    60
tgggcaagtt tccgggaaag agcagggaat ttccggggac tttccgggaa tttccgggga   120
ctttccggga atttccagag cagggaattt ccggggactt tccgggaatt ccgggggact   180
ttccgggaat ttccagagca tattaaggtg acgcgtgtgg cctcgaacac cgagcgaccc   240
tgcagcgacc cgcttaaaag gcgcgcc                                        267

<210> SEQ ID NO 12
<211> LENGTH: 372
<212> TYPE: DNA
<213> ORGANISM: Artificial Sequence
<220> FEATURE:
<223> OTHER INFORMATION: Synthetic sequence

<400> SEQUENCE: 12
ttccgggaaa gggtgggcaa gtttccggga aagcagtagg tacagccttc cgggaaaggg    60
tgggcaagtt tccgggaaag cagtaggtac agccttccgg gaaagggtgg gcaagtttcc   120
gggaaagagc aggggaattc cggggacttt ccgggaattt ccgggggactt tccgggaatt  180 tccagagcag ggaatttccg gggactttcc gggaatttcc ggggactttc cgggaatttc   240
cagagcaggg aatttccggg gactttccgg gaatttccgg ggactttccg ggaatttcca   300
gagcatatta aggtgacgcg tgtggcctcg aacaccgagc gaccctgcag cgacccgctt   360
aaaaggcgcg cc                                                        372

<210> SEQ ID NO 13
<211> LENGTH: 456
<212> TYPE: DNA
<213> ORGANISM: Artificial Sequence
<220> FEATURE:
<223> OTHER INFORMATION: Synthetic sequence

<400> SEQUENCE: 13
ttccgggaaa gggtgggcaa gtttccggga aagcagtagg tacagccttc cgggaaaggg    60
tgggcaagtt tccgggaaag cagtaggtac agccttccgg gaaagggtgg gcaagtttcc   120
gggaaagcag taggtacagc cgaccttgag tacgtgcgtc tctgcacgta tgagagcaga   180
```
ccttgagtac gtgcgtctct gcacgtatga gagcagggaa tttccgggga ctttccggga          240
atttccgggg actttccggg aatttccaga gcagggaatt tccggggact ttccgggaat          300
ttccggggac tttccgggaa tttccagagc agggaatttc cggggacttt ccgggaattt          360
ccggggactt ccgggaatt tccagagcat attaaggtga cgcgtgtggc ctcgaacacc          420
gagcgaccct gcagcgaccc gcttaaaagg cgcgcc                                     456

<210> SEQ ID NO 14
<211> LENGTH: 446
<212> TYPE: DNA
<213> ORGANISM: Artificial Sequence
<220> FEATURE:
<223> OTHER INFORMATION: Synthetic sequence

<400> SEQUENCE: 14
ttccgggaaa gggtgggcaa gtttccggga aagcagtagg tacagccttc cgggaaaggg           60
tgggcaagtt tccgggaaag cagtaggtac agccttccgg gaaagggtgg gcaagtttcc          120
gggaaagagc agggaatttc cggggacttt ccgggaattt ccggggactt ccgggaatt          180 tccagagcag gaatttccg gggactttcc gggaatttcc ggggactttc cgggaatttc          240
cagagcaggg aatttccggg actttccgg gaatttccgg ggactttccg ggaatttcca          300
gagcagacct tgagtacgtg cgtctctgca cgtatgagag cagaccttga gtacgtgcgt          360
ctctgcacgt atgagagcat attaaggtga cgcgtgtggc ctcgaacacc gagcgaccct          420
gcagcgaccc gcttaaaagg cgcgcc                                                446

<210> SEQ ID NO 15
<211> LENGTH: 351
<212> TYPE: DNA
<213> ORGANISM: Artificial Sequence
<220> FEATURE:
<223> OTHER INFORMATION: Synthetic sequence

<400> SEQUENCE: 15
ttccgggaaa gggtgggcaa gtttccggga aagcagtagg tacagccttc cgggaaaggg           60
tgggcaagtt tccgggaaag cagtaggtac agccgacctt gagtacgtgc gtctctgcac          120
gtatgagagc agaccttgag tacgtgcgtc tctgcacgta tgagagcagg gaatttccgg          180
ggactttccg ggaatttccg gggactttcc gggaatttcc agagcaggga atttccgggg          240
actttccggg aatttccggg gactttccgg gaatttccag agcatattaa ggtgacgcgt          300
gtggcctcga acaccgagcg accctgcagc gacccgctta aaggcgcgc c                    351

<210> SEQ ID NO 16
<211> LENGTH: 341
<212> TYPE: DNA
<213> ORGANISM: Artificial Sequence
<220> FEATURE:
<223> OTHER INFORMATION: Synthetic sequence

<400> SEQUENCE: 16
ttccgggaaa gggtgggcaa gtttccggga aagcagtagg tacagccttc cgggaaaggg           60
tgggcaagtt tccgggaaag agcagggaat tccggggac tttccgggaa tttccgggga          120
ctttccggga atttccagag cagggaatt ccggggactt tccgggaatt tccggggact          180
ttccgggaat ttccagagca gaccttgagt acgtgcgtct ctgcacgtat gagagcagac          240
cttgagtacg tgcgtctctg cacgtatgag agcatattaa ggtgacgcgt gtggcctcga          300
acaccgagcg accctgcagc gacccgctta aaggcgcgc c                                341

-continued

```
<210> SEQ ID NO 17
<211> LENGTH: 341
<212> TYPE: DNA
<213> ORGANISM: Artificial Sequence
<220> FEATURE:
<223> OTHER INFORMATION: Synthetic promoter

<400> SEQUENCE: 17
gaccttgagt acgtgcgtct ctgcacgtat gagagcagac cttgagtacg tgcgtctctg      60
cacgtatgag agcattccgg gaaagggtgg gcaagtttcc gggaaagcag taggtacagc     120
cttccgggaa agggtgggca agtttccggg aaagagcagg gaatttccgg ggactttccg     180
ggaatttccg gggactttcc gggaatttcc agagcaggga atttccgggg actttccggg     240
aatttccggg gactttccgg gaatttccag agcatattaa ggtgacgcgt gtggcctcga     300
acaccgagcg accctgcagc gacccgctta aaaggcgcgc c                          341

<210> SEQ ID NO 18
<211> LENGTH: 246
<212> TYPE: DNA
<213> ORGANISM: Artificial Sequence
<220> FEATURE:
<223> OTHER INFORMATION: Synthetic promoter

<400> SEQUENCE: 18
ttccgggaaa gggtgggcaa gtttccggga aagcagtagg tacagccgac cttgagtacg      60
tgcgtctctg cacgtatgag agcagacctt gagtacgtgc gtctctgcac gtatgagagc     120
agggaatttc cggggacttt ccgggaattt ccggggactt ccgggaatt tccagagcat      180 attaaggtga cgcgtgtggc ctcgaacacc gagcgaccct gcagcgaccc gcttaaaagg     240
cgcgcc                                                                 246

<210> SEQ ID NO 19
<211> LENGTH: 169
<212> TYPE: DNA
<213> ORGANISM: Artificial Sequence
<220> FEATURE:
<223> OTHER INFORMATION: Synthetic sequence

<400> SEQUENCE: 19
ttccgggaaa gggtgggcaa gtttccggga acccgacctt gagtacgtgc gtctctgcac      60
gtatgtacag cgcttcctga cagtgacgcg agccgagagc atattaaggt gacgcgtgtg     120
gcctcgaaca ccgagcgacc ctgcagcgac ccgcttaaaa gcggccgcc                 169

<210> SEQ ID NO 20
<211> LENGTH: 169
<212> TYPE: DNA
<213> ORGANISM: Artificial Sequence
<220> FEATURE:
<223> OTHER INFORMATION: Synthetic sequence

<400> SEQUENCE: 20
ttccgggaaa gggtgggcaa gtttccggga acccgggaat tccggggac tttccgggaa      60 tttcctacag cgcttcctga cagtgacgcg agccgagagc atattaaggt gacgcgtgtg     120
gcctcgaaca ccgagcgacc ctgcagcgac ccgcttaaaa gcggccgcc                 169

<210> SEQ ID NO 21
<211> LENGTH: 174
<212> TYPE: DNA
```

-continued

```
<213> ORGANISM: Artificial Sequence
<220> FEATURE:
<223> OTHER INFORMATION: Synthetic promoter

<400> SEQUENCE: 21
ttccgggaaa gggtgggcaa gtttccggga acccgggaat ttccggggac tttccgggaa      60
tttcctacag accttgagta cgtgcgtctc tgcacgtatg agagcatatt aaggtgacgc     120
gtgtggcctc gaacaccgag cgaccctgca gcgacccgct taaaagcggc cgcc           174

<210> SEQ ID NO 22
<211> LENGTH: 250
<212> TYPE: DNA
<213> ORGANISM: Artificial Sequence
<220> FEATURE:
<223> OTHER INFORMATION: Synthetic sequence

<400> SEQUENCE: 22
tacagggaca gcagagatcc agtttggact agcccggtcg cactagttct agaacttccc      60
ggaaataggg tgggcaagta tttccgggaa attctagagg gagttcccgg ggactttccg     120
gggattttct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 23
<211> LENGTH: 250
<212> TYPE: DNA
<213> ORGANISM: Artificial Sequence
<220> FEATURE:
<223> OTHER INFORMATION: Synthetic sequence

<400> SEQUENCE: 23
tacagggaca gcagagatcc agtttggact agcccggtcg cactagttct agaacttccc      60
ggaagtaggg tgggcaagta cttcccggaa gttctagagg aaattttcgg ggactttccg     120
ggggttctct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 24
<211> LENGTH: 250
<212> TYPE: DNA
<213> ORGANISM: Artificial Sequence
<220> FEATURE:
<223> OTHER INFORMATION: Synthetic sequence

<400> SEQUENCE: 24
tacagggaca gcagagatcc agtttggact agcccggtcg cactagttct agaacttccc      60
ggaagtaggg tgggcaagta cttccgggaa attctagagg gagttctcgg ggactttccg     120
ggaattttct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 25
<211> LENGTH: 250
<212> TYPE: DNA
<213> ORGANISM: Artificial Sequence
<220> FEATURE:
<223> OTHER INFORMATION: Synthetic sequence
```

-continued

```
<400> SEQUENCE: 25
tacagggaca gcagagatcc agtttggact agcccggtcg cactagttct agaacttccc        60
ggaagtaggg tgggcaagta tttcccggaa gttctagagg aagttctcgg ggactttccg       120
gagattctct ctagatatta aggtgacgcg tgtggcctcg aacaccgagc gaccctgcag       180
cgacccgctt aaaagcggcc gccatgggcc gccatggcct cctccgagga cgtcatcaag       240
gagttcatgc                                                              250

<210> SEQ ID NO 26
<211> LENGTH: 250
<212> TYPE: DNA
<213> ORGANISM: Artificial Sequence
<220> FEATURE:
<223> OTHER INFORMATION: Synthetic promoter

<400> SEQUENCE: 26
tacagggaca gcagagatcc agtttggact agcccggtcg cactagttct agaacttccg        60
ggaaataggg tgggcaagta cttccgggaa attctagagg ggatttccgg ggactttccg       120
gaggttctct ctagatatta aggtgacgcg tgtggcctcg aacaccgagc gaccctgcag       180
cgacccgctt aaaagcggcc gccatgggcc gccatggcct cctccgagga cgtcatcaag       240
gagttcatgc                                                              250

<210> SEQ ID NO 27
<211> LENGTH: 250
<212> TYPE: DNA
<213> ORGANISM: Artificial Sequence
<220> FEATURE:
<223> OTHER INFORMATION: Synthetic promoter

<400> SEQUENCE: 27
tacagggaca gcagagatcc agtttggact agcccggtcg cactagttct agaacttccg        60
ggaaataggg tgggcaagta cttccgggaa gttctagagg aggttttcgg ggactttccg       120
gaggtttcct ctagatatta aggtgacgcg tgtggcctcg aacaccgagc gaccctgcag       180
cgacccgctt aaaagcggcc gccatgggcc gccatggcct cctccgagga cgtcatcaag       240
gagttcatgc                                                              250

<210> SEQ ID NO 28
<211> LENGTH: 250
<212> TYPE: DNA
<213> ORGANISM: Artificial Sequence
<220> FEATURE:
<223> OTHER INFORMATION: Synthetic sequence

<400> SEQUENCE: 28
tacagggaca gcagagatcc agtttggact agcccggtcg cactagttct agaacttccg        60
ggaagtaggg tgggcaagta tttcccggaa gttctagagg gggttttcgg ggactttccg       120
gaggtttcct ctagatatta aggtgacgcg tgtggcctcg aacaccgagc gaccctgcag       180
cgacccgctt aaaagcggcc gccatgggcc gccatggcct cctccgagga cgtcatcaag       240
gagttcatgc                                                              250

<210> SEQ ID NO 29
<211> LENGTH: 250
<212> TYPE: DNA
<213> ORGANISM: Artificial Sequence
<220> FEATURE:
```

<223> OTHER INFORMATION: Synthetic sequence

<400> SEQUENCE: 29
tacagggaca gcagagatcc agtttggact agcccggtcg cactagttct agaacttccg      60
ggaagtaggg tgggcaagta tttccgggaa attctagagg gagttctcgg ggactttccg     120
gggattttct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                           250

<210> SEQ ID NO 30
<211> LENGTH: 250
<212> TYPE: DNA
<213> ORGANISM: Artificial Sequence
<220> FEATURE:
<223> OTHER INFORMATION: Synthetic sequence

<400> SEQUENCE: 30
tacagggaca gcagagatcc agtttggact agcccggtcg cactagttct agaatttccc      60
ggaaataggg tgggcaagta cttccgggaa attctagagg gggtttccgg ggactttccg     120 ggggtttttct ctagatatta aggtgacgcg tgtggcctcg aacaccgagc gaccctgcag    180
cgacccgctt aaaagcggcc gccatgggcc gccatggcct cctccgagga cgtcatcaag     240
gagttcatgc                                                           250

<210> SEQ ID NO 31
<211> LENGTH: 250
<212> TYPE: DNA
<213> ORGANISM: Artificial Sequence
<220> FEATURE:
<223> OTHER INFORMATION: Synthetic sequence

<400> SEQUENCE: 31
tacagggaca gcagagatcc agtttggact agcccggtcg cactagttct agaatttccc      60
ggaaataggg tgggcaagta cttccgggaa attctagagg gggtttccgg ggactttccg     120 ggggtttttct ctagatatta aggtgacgcg tgtggcctcg aacaccgagc gaccctgcag    180
cgacccgctt aaaagcggcc gccatgggcc gccatggcct cctccgagga cgtcatcaag     240
gagttcatgc                                                           250

<210> SEQ ID NO 32
<211> LENGTH: 250
<212> TYPE: DNA
<213> ORGANISM: Artificial Sequence
<220> FEATURE:
<223> OTHER INFORMATION: Synthetic sequence

<400> SEQUENCE: 32
tacagggaca gcagagatcc agtttggact agcccggtcg cactagttct agaatttccc      60
ggaaataggg tgggcaagta tttccgggaa attctagagg aggttctcgg ggactttccg     120
ggagttttct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                           250

<210> SEQ ID NO 33
<211> LENGTH: 250
<212> TYPE: DNA
<213> ORGANISM: Artificial Sequence

```
<220> FEATURE:
<223> OTHER INFORMATION: Synthetic sequence

<400> SEQUENCE: 33
tacagggaca gcagagatcc agtttggact agcccggtcg cactagttct agaatttccc      60
ggaaataggg tgggcaagta tttccgggaa attctagagg aggtttttcgg ggactttccg     120 ggagtttcct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 34
<211> LENGTH: 250
<212> TYPE: DNA
<213> ORGANISM: Artificial Sequence
<220> FEATURE:
<223> OTHER INFORMATION: Synthetic sequence

<400> SEQUENCE: 34
tacagggaca gcagagatcc agtttggact agcccggtcg cactagttct agaatttccc      60
ggaaataggg tgggcaagta tttccgggaa gttctagagg aagtttttcgg ggactttccg     120 ggaattttct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 35
<211> LENGTH: 250
<212> TYPE: DNA
<213> ORGANISM: Artificial Sequence
<220> FEATURE:
<223> OTHER INFORMATION: Synthetic sequence

<400> SEQUENCE: 35
tacagggaca gcagagatcc agtttggact agcccggtcg cactagttct agaatttccg      60
ggaaataggg tgggcaagta tttcccggaa gttctagagg agattctcgg ggactttccg     120
ggggttctct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 36
<211> LENGTH: 250
<212> TYPE: DNA
<213> ORGANISM: Artificial Sequence
<220> FEATURE:
<223> OTHER INFORMATION: Synthetic sequence

<400> SEQUENCE: 36
tacagggaca gcagagatcc agtttggact agcccggtcg cactagttct agaatttccg      60
ggaagtaggg tgggcaagta cttccgggaa attctagagg gggtttccgg ggactttccg     120
gagattctct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 37
<211> LENGTH: 250
<212> TYPE: DNA
```

-continued

```
<213> ORGANISM: Artificial Sequence
<220> FEATURE:
<223> OTHER INFORMATION: Synthetic sequence

<400> SEQUENCE: 37
tacagggaca gcagagatcc agtttggact agcccggtcg cactagttct agaatttccg      60
ggaagtaggg tgggcaagta cttccgggaa attctagagg gggtttccgg ggactttccg     120
gagattctct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                            250

<210> SEQ ID NO 38
<211> LENGTH: 249
<212> TYPE: DNA
<213> ORGANISM: Artificial Sequence
<220> FEATURE:
<223> OTHER INFORMATION: Synthetic sequence

<400> SEQUENCE: 38
tacagggaca gcagagatcc agtttggact agcccggtcg cactagttct agaacttccc      60
ggaaataggg tgggcaagta tttcccggaa gttctagagg aggttttcgg ggactttccg     120
ggattccctc tagatattaa ggtgacgcgt gtggcctcga acaccgagcg accctgcagc     180
gacccgctta aaagcggccg ccatgggccg ccatggcctc ctccgaggac gtcatcaagg     240
agttcatgc                                                             249

<210> SEQ ID NO 39
<211> LENGTH: 243
<212> TYPE: DNA
<213> ORGANISM: Artificial Sequence
<220> FEATURE:
<223> OTHER INFORMATION: Synthetic sequence

<400> SEQUENCE: 39
tacagggaca gcagagatcc agtttggact agcccggtcg cactagttct agttccggga      60
agtgggtggg caatatttcc cggaagttta gaggaagttt tcggggactt ccggaaattc     120
cctctagata ttaaggtgac gcgtgtggcc tcgaacaccg agcgaccctg cagcgacccg     180
cttaaaagcg gccgccatgg gccgccatgg cctcctccga ggacgtcatc aaggagttca     240
tgc                                                                   243

<210> SEQ ID NO 40
<211> LENGTH: 200
<212> TYPE: DNA
<213> ORGANISM: Artificial Sequence
<220> FEATURE:
<223> OTHER INFORMATION: Synthetic sequence

<400> SEQUENCE: 40
tacagggaca gcagagatcc agtttggact agcccggtcg cactagttct agaacttctc      60
ggaaataggg tgggcaagta ctgtggcctc gaacaccgag cgaccctgca gcgacccgct     120
taaaagcggc cgccatgggc cgccatggcc tcctccgagg acgtcatcaa ggagttcatg     180
cagaccaagt ctctgctacc                                                 200

<210> SEQ ID NO 41
<211> LENGTH: 250
<212> TYPE: DNA
<213> ORGANISM: Artificial Sequence
```

-continued

```
<220> FEATURE:
<223> OTHER INFORMATION: Synthetic sequence
<220> FEATURE:
<221> NAME/KEY: misc_feature
<222> LOCATION: (55)..(55)
<223> OTHER INFORMATION: y= C or T
<220> FEATURE:
<221> NAME/KEY: misc_feature
<222> LOCATION: (60)..(60)
<223> OTHER INFORMATION: S = C or G
<220> FEATURE:
<221> NAME/KEY: misc_feature
<222> LOCATION: (65)..(65)
<223> OTHER INFORMATION: R = A or G
<220> FEATURE:
<221> NAME/KEY: misc_feature
<222> LOCATION: (81)..(81)
<223> OTHER INFORMATION: Y = C or T
<220> FEATURE:
<221> NAME/KEY: misc_feature
<222> LOCATION: (86)..(86)
<223> OTHER INFORMATION: S = C or G
<220> FEATURE:
<221> NAME/KEY: misc_feature
<222> LOCATION: (91)..(91)
<223> OTHER INFORMATION: R = A or G
<220> FEATURE:
<221> NAME/KEY: misc_feature
<222> LOCATION: (101)..(103)
<223> OTHER INFORMATION: R = A or G
<220> FEATURE:
<221> NAME/KEY: misc_feature
<222> LOCATION: (106)..(107)
<223> OTHER INFORMATION: Y = C or T
<220> FEATURE:
<221> NAME/KEY: misc_feature
<222> LOCATION: (122)..(124)
<223> OTHER INFORMATION: R = A or G
<220> FEATURE:
<221> NAME/KEY: misc_feature
<222> LOCATION: (127)..(128)
<223> OTHER INFORMATION: Y = C or T

<400> SEQUENCE: 41
tacagggaca gcagagatcc agtttggact agcccggtcg cactagttct agaayttccs      60
ggaartaggg tgggcaagta yttccsggaa rttctagagg rrrttyycgg ggactttccg     120
grrrttyyct ctagatatta aggtgacgcg tgtggcctcg aacaccgagc gaccctgcag     180
cgacccgctt aaaagcggcc gccatgggcc gccatggcct cctccgagga cgtcatcaag     240
gagttcatgc                                                          250

<210> SEQ ID NO 42
<211> LENGTH: 50
<212> TYPE: DNA
<213> ORGANISM: Artificial Sequence
<220> FEATURE:
<223> OTHER INFORMATION: Synthetic sequence

<400> SEQUENCE: 42
acgtggctgg agtcacagtc ctcttacgtg gctggagtca cagtcctctt               50

<210> SEQ ID NO 43
<211> LENGTH: 50
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: R = A/G
<220> FEATURE:
```

```
<221> NAME/KEY: misc_feature
<222> LOCATION: (6)..(6)
<223> OTHER INFORMATION: S = C/G
<220> FEATURE:
<221> NAME/KEY: misc_feature
<222> LOCATION: (14)..(14)
<223> OTHER INFORMATION: M = A/C
<220> FEATURE:
<221> NAME/KEY: misc_feature
<222> LOCATION: (26)..(26)
<223> OTHER INFORMATION: R = A/G
<220> FEATURE:
<221> NAME/KEY: misc_feature
<222> LOCATION: (31)..(31)
<223> OTHER INFORMATION: S = C/G
<220> FEATURE:
<221> NAME/KEY: misc_feature
<222> LOCATION: (39)..(39)
<223> OTHER INFORMATION: M = A/C

<400> SEQUENCE: 43
rcgtgsctgg agtmacagtc ctcttrcgtg sctggagtma cagtcctctt                  50

<210> SEQ ID NO 44
<211> LENGTH: 39
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: S = C/G
<220> FEATURE:
<221> NAME/KEY: misc_feature
<222> LOCATION: (12)..(12)
<223> OTHER INFORMATION: R = A/G
<220> FEATURE:
<221> NAME/KEY: misc_feature
<222> LOCATION: (33)..(33)
<223> OTHER INFORMATION: S = C/G
<220> FEATURE:
<221> NAME/KEY: misc_feature
<222> LOCATION: (38)..(38)
<223> OTHER INFORMATION: S = A/G

<400> SEQUENCE: 44
acttccsgga artagggtgg gcaagtactt ccsggaart                              39

<210> SEQ ID NO 45
<211> LENGTH: 30
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (9)..(9)
<223> OTHER INFORMATION: Y = C or T
<220> FEATURE:
<221> NAME/KEY: misc_feature
<222> LOCATION: (9)..(9)
<223> OTHER INFORMATION: Y = C/T
<220> FEATURE:
<221> NAME/KEY: misc_feature
<222> LOCATION: (24)..(26)
<223> OTHER INFORMATION: R = A/G

<400> SEQUENCE: 45
gggggtttyc ggggactttc cggrrrtttt                                        30

<210> SEQ ID NO 46
<211> LENGTH: 10
```

```
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: K = G/T
<220> FEATURE:
<221> NAME/KEY: misc_feature
<222> LOCATION: (4)..(4)
<223> OTHER INFORMATION: K = G/T
<220> FEATURE:
<221> NAME/KEY: misc_feature
<222> LOCATION: (5)..(5)
<223> OTHER INFORMATION: K = A/C
<220> FEATURE:
<221> NAME/KEY: misc_feature
<222> LOCATION: (5)..(5)
<223> OTHER INFORMATION: M = A/C
<220> FEATURE:
<221> NAME/KEY: misc_feature
<222> LOCATION: (7)..(7)
<223> OTHER INFORMATION: M = A/C
<220> FEATURE:
<221> NAME/KEY: misc_feature
<222> LOCATION: (7)..(7)
<223> OTHER INFORMATION: M = A/C
<220> FEATURE:
<221> NAME/KEY: misc_feature
<222> LOCATION: (9)..(10)
<223> OTHER INFORMATION: n = A/C/G/T

<400> SEQUENCE: 46 gkckmgmcnn                                                                                    10

<210> SEQ ID NO 47
<211> LENGTH: 20
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: K = G/T
<220> FEATURE:
<221> NAME/KEY: misc_feature
<222> LOCATION: (4)..(4)
<223> OTHER INFORMATION: K = G/T
<220> FEATURE:
<221> NAME/KEY: misc_feature
<222> LOCATION: (5)..(5)
<223> OTHER INFORMATION: M = A/C
<220> FEATURE:
<221> NAME/KEY: misc_feature
<222> LOCATION: (7)..(7)
<223> OTHER INFORMATION: M = A/C
<220> FEATURE:
<221> NAME/KEY: misc_feature
<222> LOCATION: (15)..(15)
<223> OTHER INFORMATION: K = G/T
<220> FEATURE:
<221> NAME/KEY: misc_feature
<222> LOCATION: (17)..(17)
<223> OTHER INFORMATION: K = G/T
<220> FEATURE:
<221> NAME/KEY: misc_feature
<222> LOCATION: (18)..(18)
<223> OTHER INFORMATION: M = A/C
<220> FEATURE:
<221> NAME/KEY: misc_feature
<222> LOCATION: (20)..(20)
<223> OTHER INFORMATION: M = A/C

<400> SEQUENCE: 47
```

-continued gkckmgmcgg cgcgkckmgm                                                    20

<210> SEQ ID NO 48
<211> LENGTH: 50
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: K = G/T
<220> FEATURE:
<221> NAME/KEY: misc_feature
<222> LOCATION: (4)..(4)
<223> OTHER INFORMATION: K = G/T
<220> FEATURE:
<221> NAME/KEY: misc_feature
<222> LOCATION: (5)..(5)
<223> OTHER INFORMATION: M = A/C
<220> FEATURE:
<221> NAME/KEY: misc_feature
<222> LOCATION: (7)..(7)
<223> OTHER INFORMATION: M = A/C
<220> FEATURE:
<221> NAME/KEY: misc_feature
<222> LOCATION: (15)..(15)
<223> OTHER INFORMATION: K = G/T
<220> FEATURE:
<221> NAME/KEY: misc_feature
<222> LOCATION: (17)..(17)
<223> OTHER INFORMATION: K = G/T
<220> FEATURE:
<221> NAME/KEY: misc_feature
<222> LOCATION: (18)..(18)
<223> OTHER INFORMATION: M = A/C
<220> FEATURE:
<221> NAME/KEY: misc_feature
<222> LOCATION: (20)..(20)
<223> OTHER INFORMATION: M = A/C
<220> FEATURE:
<221> NAME/KEY: misc_feature
<222> LOCATION: (31)..(31)
<223> OTHER INFORMATION: K = G/T
<220> FEATURE:
<221> NAME/KEY: misc_feature
<222> LOCATION: (33)..(33)
<223> OTHER INFORMATION: K = G/T
<220> FEATURE:
<221> NAME/KEY: misc_feature
<222> LOCATION: (34)..(34)
<223> OTHER INFORMATION: M = A/C
<220> FEATURE:
<221> NAME/KEY: misc_feature
<222> LOCATION: (36)..(36)
<223> OTHER INFORMATION: M = A/C
<220> FEATURE:
<221> NAME/KEY: misc_feature
<222> LOCATION: (44)..(44)
<223> OTHER INFORMATION: K = G/T
<220> FEATURE:
<221> NAME/KEY: misc_feature
<222> LOCATION: (46)..(46)
<223> OTHER INFORMATION: K = G/T
<220> FEATURE:
<221> NAME/KEY: misc_feature
<222> LOCATION: (47)..(47)
<223> OTHER INFORMATION: M = A/C
<220> FEATURE:
<221> NAME/KEY: misc_feature
<222> LOCATION: (49)..(49)
<223> OTHER INFORMATION: M = A/C

<400> SEQUENCE: 48
gkckmgmcgg cgcgkckmgm cattctagag kckmgmcggc gcgkckmgmc                    50

```
<210> SEQ ID NO 49
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Y = C/T
<220> FEATURE:
<221> NAME/KEY: misc_feature
<222> LOCATION: (5)..(5)
<223> OTHER INFORMATION: S = C/G
<220> FEATURE:
<221> NAME/KEY: misc_feature
<222> LOCATION: (10)..(10)
<223> OTHER INFORMATION: n = C/G/A/T

<400> SEQUENCE: 49 ttcysggaan                                                              10

<210> SEQ ID NO 50
<211> LENGTH: 35
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Y = C/T
<220> FEATURE:
<221> NAME/KEY: misc_feature
<222> LOCATION: (5)..(5)
<223> OTHER INFORMATION: S = C/G
<220> FEATURE:
<221> NAME/KEY: misc_feature
<222> LOCATION: (30)..(30)
<223> OTHER INFORMATION: Y = C/T
<220> FEATURE:
<221> NAME/KEY: misc_feature
<222> LOCATION: (31)..(31)
<223> OTHER INFORMATION: S = C/G

<400> SEQUENCE: 50
ttcysggaaa tagggtgggc aagtatttcy sggaa                                   35

<210> SEQ ID NO 51
<211> LENGTH: 93
<212> TYPE: DNA
<213> ORGANISM: Artificial Sequence
<220> FEATURE:
<223> OTHER INFORMATION: Synthetic promoter
<220> FEATURE:
<221> NAME/KEY: misc_feature
<222> LOCATION: (2)..(2)
<223> OTHER INFORMATION: K = G/T
<220> FEATURE:
<221> NAME/KEY: misc_feature
<222> LOCATION: (4)..(4)
<223> OTHER INFORMATION: K = G/T
<220> FEATURE:
<221> NAME/KEY: misc_feature
<222> LOCATION: (5)..(5)
<223> OTHER INFORMATION: M = A/C
<220> FEATURE:
<221> NAME/KEY: misc_feature
<222> LOCATION: (7)..(7)
<223> OTHER INFORMATION: M = A/C
<220> FEATURE:
<221> NAME/KEY: misc_feature
<222> LOCATION: (15)..(15)
<223> OTHER INFORMATION: K = G/T
<220> FEATURE:
```

-continued

```
<221> NAME/KEY: misc_feature
<222> LOCATION: (17)..(17)
<223> OTHER INFORMATION: K = G/T
<220> FEATURE:
<221> NAME/KEY: misc_feature
<222> LOCATION: (18)..(18)
<223> OTHER INFORMATION: M = A/C
<220> FEATURE:
<221> NAME/KEY: misc_feature
<222> LOCATION: (20)..(20)
<223> OTHER INFORMATION: M = A/C
<220> FEATURE:
<221> NAME/KEY: misc_feature
<222> LOCATION: (31)..(31)
<223> OTHER INFORMATION: K = G/T
<220> FEATURE:
<221> NAME/KEY: misc_feature
<222> LOCATION: (33)..(33)
<223> OTHER INFORMATION: K = G/T
<220> FEATURE:
<221> NAME/KEY: misc_feature
<222> LOCATION: (34)..(34)
<223> OTHER INFORMATION: M = A/C
<220> FEATURE:
<221> NAME/KEY: misc_feature
<222> LOCATION: (36)..(36)
<223> OTHER INFORMATION: M = A/C
<220> FEATURE:
<221> NAME/KEY: misc_feature
<222> LOCATION: (44)..(44)
<223> OTHER INFORMATION: K = G/T
<220> FEATURE:
<221> NAME/KEY: misc_feature
<222> LOCATION: (46)..(46)
<223> OTHER INFORMATION: K = G/T
<220> FEATURE:
<221> NAME/KEY: misc_feature
<222> LOCATION: (47)..(47)
<223> OTHER INFORMATION: M = A/C
<220> FEATURE:
<221> NAME/KEY: misc_feature
<222> LOCATION: (49)..(49)
<223> OTHER INFORMATION: M = A/C
<220> FEATURE:
<221> NAME/KEY: misc_feature
<222> LOCATION: (62)..(62)
<223> OTHER INFORMATION: Y = C/T
<220> FEATURE:
<221> NAME/KEY: misc_feature
<222> LOCATION: (63)..(63)
<223> OTHER INFORMATION: S = C/G
<220> FEATURE:
<221> NAME/KEY: misc_feature
<222> LOCATION: (88)..(88)
<223> OTHER INFORMATION: Y = C/T
<220> FEATURE:
<221> NAME/KEY: misc_feature
<222> LOCATION: (89)..(89)
<223> OTHER INFORMATION: S = C/G

<400> SEQUENCE: 51
gkckmgmcgg cgcgkckmgm cattctagag kckmgmcggc gcgkckmgmc tctagaattt      60
cysggaaata gggtgggcaa gtatttcysg gaa                                  93

<210> SEQ ID NO 52
<211> LENGTH: 26
<212> TYPE: DNA
<213> ORGANISM: Artificial Sequence
<220> FEATURE:
<223> OTHER INFORMATION: Synthetic promoter
<220> FEATURE:
<221> NAME/KEY: misc_feature
<222> LOCATION: (20)..(20)
<223> OTHER INFORMATION: Y = C/T
<220> FEATURE:
<221> NAME/KEY: misc_feature
```

-continued

```
<222> LOCATION: (21)..(21)
<223> OTHER INFORMATION: B = C/G/T
<220> FEATURE:
<221> NAME/KEY: misc_feature
<222> LOCATION: (22)..(22)
<223> OTHER INFORMATION: W = A/T

<400> SEQUENCE: 52
gcgcttcctg acagtgacgy bwgccg                                            26

<210> SEQ ID NO 53
<211> LENGTH: 129
<212> TYPE: DNA
<213> ORGANISM: Artificial Sequence
<220> FEATURE:
<223> OTHER INFORMATION: Artificial sequence
<220> FEATURE:
<221> NAME/KEY: misc_feature
<222> LOCATION: (2)..(2)
<223> OTHER INFORMATION: K = G/T
<220> FEATURE:
<221> NAME/KEY: misc_feature
<222> LOCATION: (4)..(4)
<223> OTHER INFORMATION: K = G/T
<220> FEATURE:
<221> NAME/KEY: misc_feature
<222> LOCATION: (5)..(5)
<223> OTHER INFORMATION: M = A/C
<220> FEATURE:
<221> NAME/KEY: misc_feature
<222> LOCATION: (7)..(7)
<223> OTHER INFORMATION: M = A/C
<220> FEATURE:
<221> NAME/KEY: misc_feature
<222> LOCATION: (15)..(15)
<223> OTHER INFORMATION: K = G/T
<220> FEATURE:
<221> NAME/KEY: misc_feature
<222> LOCATION: (17)..(17)
<223> OTHER INFORMATION: K = G/T
<220> FEATURE:
<221> NAME/KEY: misc_feature
<222> LOCATION: (18)..(18)
<223> OTHER INFORMATION: M = A/C
<220> FEATURE:
<221> NAME/KEY: misc_feature
<222> LOCATION: (20)..(20)
<223> OTHER INFORMATION: M = A/C
<220> FEATURE:
<221> NAME/KEY: misc_feature
<222> LOCATION: (31)..(31)
<223> OTHER INFORMATION: K = G/T
<220> FEATURE:
<221> NAME/KEY: misc_feature
<222> LOCATION: (33)..(33)
<223> OTHER INFORMATION: K = G/T
<220> FEATURE:
<221> NAME/KEY: misc_feature
<222> LOCATION: (34)..(34)
<223> OTHER INFORMATION: M = A/C
<220> FEATURE:
<221> NAME/KEY: misc_feature
<222> LOCATION: (36)..(36)
<223> OTHER INFORMATION: M = A/C
<220> FEATURE:
<221> NAME/KEY: misc_feature
<222> LOCATION: (44)..(44)
<223> OTHER INFORMATION: K = G/T
<220> FEATURE:
<221> NAME/KEY: misc_feature
<222> LOCATION: (46)..(46)
<223> OTHER INFORMATION: K = G/T
<220> FEATURE:
<221> NAME/KEY: misc_feature
<222> LOCATION: (47)..(47)
<223> OTHER INFORMATION: M = A/C
<220> FEATURE:
```

```
<221> NAME/KEY: misc_feature
<222> LOCATION: (49)..(49)
<223> OTHER INFORMATION: M = A/C
<220> FEATURE:
<221> NAME/KEY: misc_feature
<222> LOCATION: (78)..(78)
<223> OTHER INFORMATION: Y = C/T
<220> FEATURE:
<221> NAME/KEY: misc_feature
<222> LOCATION: (79)..(79)
<223> OTHER INFORMATION: B = C/G/T
<220> FEATURE:
<221> NAME/KEY: misc_feature
<222> LOCATION: (80)..(80)
<223> OTHER INFORMATION: W = A/T

<400> SEQUENCE: 53
gkckmgmcgg cgcgkckmgm cattctagag kckmgmcggc gcgkckmgmc tctagaatgc        60
gcttcctgac agtgacgybw gccgattcta gagggggttt tcggggactt tccgggaatt       120
ttctctaga                                                              129

<210> SEQ ID NO 54
<211> LENGTH: 138
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Y = C/T
<220> FEATURE:
<221> NAME/KEY: misc_feature
<222> LOCATION: (5)..(5)
<223> OTHER INFORMATION: S = C/G
<220> FEATURE:
<221> NAME/KEY: misc_feature
<222> LOCATION: (30)..(30)
<223> OTHER INFORMATION: Y = C/T
<220> FEATURE:
<221> NAME/KEY: misc_feature
<222> LOCATION: (31)..(31)
<223> OTHER INFORMATION: S = C/G
<220> FEATURE:
<221> NAME/KEY: misc_feature
<222> LOCATION: (84)..(84)
<223> OTHER INFORMATION: K = G/T
<220> FEATURE:
<221> NAME/KEY: misc_feature
<222> LOCATION: (86)..(86)
<223> OTHER INFORMATION: K = G/T
<220> FEATURE:
<221> NAME/KEY: misc_feature
<222> LOCATION: (87)..(87)
<223> OTHER INFORMATION: M = A/C
<220> FEATURE:
<221> NAME/KEY: misc_feature
<222> LOCATION: (89)..(89)
<223> OTHER INFORMATION: M = A/C
<220> FEATURE:
<221> NAME/KEY: misc_feature
<222> LOCATION: (97)..(97)
<223> OTHER INFORMATION: K = G/T
<220> FEATURE:
<221> NAME/KEY: misc_feature
<222> LOCATION: (99)..(99)
<223> OTHER INFORMATION: K = G/T
<220> FEATURE:
<221> NAME/KEY: misc_feature
<222> LOCATION: (100)..(100)
<223> OTHER INFORMATION: M = A/C
<220> FEATURE:
<221> NAME/KEY: misc_feature
<222> LOCATION: (102)..(102)
<223> OTHER INFORMATION: M = A/C
```

```
<220> FEATURE:
<221> NAME/KEY: misc_feature
<222> LOCATION: (113)..(113)
<223> OTHER INFORMATION: K = G/T
<220> FEATURE:
<221> NAME/KEY: misc_feature
<222> LOCATION: (115)..(115)
<223> OTHER INFORMATION: K = G/T
<220> FEATURE:
<221> NAME/KEY: misc_feature
<222> LOCATION: (116)..(116)
<223> OTHER INFORMATION: M = A/C
<220> FEATURE:
<221> NAME/KEY: misc_feature
<222> LOCATION: (118)..(118)
<223> OTHER INFORMATION: M = A/C
<220> FEATURE:
<221> NAME/KEY: misc_feature
<222> LOCATION: (126)..(126)
<223> OTHER INFORMATION: K = G/T
<220> FEATURE:
<221> NAME/KEY: misc_feature
<222> LOCATION: (128)..(128)
<223> OTHER INFORMATION: K = G/T
<220> FEATURE:
<221> NAME/KEY: misc_feature
<222> LOCATION: (129)..(129)
<223> OTHER INFORMATION: M = A/C

<400> SEQUENCE: 54
ttcysggaaa tagggtgggc aagtatttcy sggaaattct agaggggggtt ttcggggact        60 ttccgggaat tttctctaga atgkckmgmc ggcgcgkckm gmcattctag agkckmgmcg       120
gcgcgkckmg mctctaga                                                      138

<210> SEQ ID NO 55
<211> LENGTH: 129
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: K = G/T
<220> FEATURE:
<221> NAME/KEY: misc_feature
<222> LOCATION: (4)..(4)
<223> OTHER INFORMATION: K = G/T
<220> FEATURE:
<221> NAME/KEY: misc_feature
<222> LOCATION: (5)..(5)
<223> OTHER INFORMATION: M = A/C
<220> FEATURE:
<221> NAME/KEY: misc_feature
<222> LOCATION: (7)..(7)
<223> OTHER INFORMATION: M = A/C
<220> FEATURE:
<221> NAME/KEY: misc_feature
<222> LOCATION: (15)..(15)
<223> OTHER INFORMATION: K = G/T
<220> FEATURE:
<221> NAME/KEY: misc_feature
<222> LOCATION: (17)..(17)
<223> OTHER INFORMATION: K = G/T
<220> FEATURE:
<221> NAME/KEY: misc_feature
<222> LOCATION: (18)..(18)
<223> OTHER INFORMATION: M = A/C
<220> FEATURE:
<221> NAME/KEY: misc_feature
<222> LOCATION: (20)..(20)
<223> OTHER INFORMATION: M = A/C
<220> FEATURE:
<221> NAME/KEY: misc_feature
<222> LOCATION: (31)..(31)
```

-continued

<223> OTHER INFORMATION: K = G/T
<220> FEATURE:
<221> NAME/KEY: misc_feature
<222> LOCATION: (33)..(33)
<223> OTHER INFORMATION: K = G/T
<220> FEATURE:
<221> NAME/KEY: misc_feature
<222> LOCATION: (34)..(34)
<223> OTHER INFORMATION: M = A/C
<220> FEATURE:
<221> NAME/KEY: misc_feature
<222> LOCATION: (36)..(36)
<223> OTHER INFORMATION: M = A/C
<220> FEATURE:
<221> NAME/KEY: misc_feature
<222> LOCATION: (44)..(44)
<223> OTHER INFORMATION: K = G/T
<220> FEATURE:
<221> NAME/KEY: misc_feature
<222> LOCATION: (46)..(46)
<223> OTHER INFORMATION: K = G/T
<220> FEATURE:
<221> NAME/KEY: misc_feature
<222> LOCATION: (46)..(46)
<223> OTHER INFORMATION: K = G/T
<220> FEATURE:
<221> NAME/KEY: misc_feature
<222> LOCATION: (47)..(47)
<223> OTHER INFORMATION: M = A/C
<220> FEATURE:
<221> NAME/KEY: misc_feature
<222> LOCATION: (49)..(49)
<223> OTHER INFORMATION: M = A/C
<220> FEATURE:
<221> NAME/KEY: misc_feature
<222> LOCATION: (78)..(78)
<223> OTHER INFORMATION: Y = C/T
<220> FEATURE:
<221> NAME/KEY: misc_feature
<222> LOCATION: (79)..(79)
<223> OTHER INFORMATION: B = C/G/T
<220> FEATURE:
<221> NAME/KEY: misc_feature
<222> LOCATION: (80)..(80)
<223> OTHER INFORMATION: W = A/T

<400> SEQUENCE: 55
gkckmgmcgg cgcgkckmgm cattctagag kckmgmcggc gcgkckmgmc tctagaatgc      60
gcttcctgac agtgacgybw gccgattcta gaggggtttt cggggactt tccgggaatt     120 ttctctaga                                                            129

<210> SEQ ID NO 56
<211> LENGTH: 140
<212> TYPE: DNA
<213> ORGANISM: Artificial Sequence
<220> FEATURE:
<223> OTHER INFORMATION: Synthetic sequence

<400> SEQUENCE: 56
gactagacta gttctagagt cgagacggcg cgtctagaca ttctagagtc tagccggcgc      60
gcctctagaa tttctgggaa atagggtggg caagtatttc tcggaaattc tagaggggt     120 tttcggggac tttccgggaa                                                140

<210> SEQ ID NO 57
<211> LENGTH: 136
<212> TYPE: DNA
<213> ORGANISM: Artificial Sequence
<220> FEATURE:
<223> OTHER INFORMATION: Synthetic sequence

<400> SEQUENCE: 57
gactagacta gttctagagt cgagccggcg cgtctcgaca ttctagagtc tagacggcgc      60
gtctagactc tagaatgcgc ttcctgacag tgacgcgtgc cgattctaga gggggttttc     120
ggggactttc cgggaa                                                      136

<210> SEQ ID NO 58
<211> LENGTH: 136
<212> TYPE: DNA
<213> ORGANISM: Artificial Sequence
<220> FEATURE:
<223> OTHER INFORMATION: Synthetic sequence

<400> SEQUENCE: 58
gactagacta gttctagagt ctagacggcg cgtcgagcca ttctagagtc tagacggcgc      60
ggctcgactc tagaatgcgc ttcctgacag tgacgcttgc cgattctaga gggggttttc     120
ggggactttc cgggaa                                                      136

<210> SEQ ID NO 59
<211> LENGTH: 136
<212> TYPE: DNA
<213> ORGANISM: Artificial Sequence
<220> FEATURE:
<223> OTHER INFORMATION: Synthetic sequence

<400> SEQUENCE: 59
gactagacta gttctagagt cgagacggcg cgtcgagaca ttctagagtc gagacggcgc      60
gtctagactc tagaatgcgc ttcctgacag tgacgttagc cgattctaga gggggttttc     120
ggggactttc cgggaa                                                      136

<210> SEQ ID NO 60
<211> LENGTH: 136
<212> TYPE: DNA
<213> ORGANISM: Artificial Sequence
<220> FEATURE:
<223> OTHER INFORMATION: Synthetic sequence

<400> SEQUENCE: 60
gactagacta gttctagagt ctagacggcg cgtcgcgaca ttctagagtc tagccggcgc      60
gtcgcgcctc tagaatgcgc ttcctgacag tgacgctagc cgattctaga gggggttttc     120
ggggactttc cgggaa                                                      136

<210> SEQ ID NO 61
<211> LENGTH: 136
<212> TYPE: DNA
<213> ORGANISM: Artificial Sequence
<220> FEATURE:
<223> OTHER INFORMATION: Synthetic sequence

<400> SEQUENCE: 61
gactagacta gttctagagg ctagccggcg cggctagaca ttctagaggc tagccggcgc      60
gtcgcgactc tagaatgcgc ttcctgacag tgacgttagc cgattctaga gggggttttc     120
ggggactttc cgggaa                                                      136

<210> SEQ ID NO 62
<211> LENGTH: 84
<212> TYPE: DNA
<213> ORGANISM: Artificial Sequence
<220> FEATURE:
<223> OTHER INFORMATION: Synthetic sequence -continued

```
<400> SEQUENCE: 62
agtctagacg gcgcggtctg ggaaataggg tgggcaagta tttctgggaa attctagagg    60
gggttttcgg ggactttccg ggaa                                          84

<210> SEQ ID NO 63
<211> LENGTH: 122
<212> TYPE: DNA
<213> ORGANISM: Artificial Sequence
<220> FEATURE:
<223> OTHER INFORMATION: Synthetic sequence

<400> SEQUENCE: 63
gactagacta gttctagagg ctagccggcg cgtctagcca ttctagagtc tagacggcgc    60
gtctcgcctc tagaatgcgc ttcctgacag tgacgtcagc cgattctaga gggggttttc   120
gg                                                                  122

<210> SEQ ID NO 64
<211> LENGTH: 136
<212> TYPE: DNA
<213> ORGANISM: Artificial Sequence
<220> FEATURE:
<223> OTHER INFORMATION: Synthetic sequence

<400> SEQUENCE: 64
gactagacta gttctagagt cgcgccggcg cgtcgcgaca ttctagagtc tagacggcgc    60
gtctagactc tagaatgcgc ttcctgacag tgacgcgtgc cgattctaga gggggttttc   120
ggggactttc cgggaa                                                   136

<210> SEQ ID NO 65
<211> LENGTH: 136
<212> TYPE: DNA
<213> ORGANISM: Artificial Sequence
<220> FEATURE:
<223> OTHER INFORMATION: Synthetic sequence

<400> SEQUENCE: 65
gactagacta gttctagagt ctagacggcg cggctagcca ttctagagtc gcgccggcgc    60
gtctagcctc tagaatgcgc ttcctgacag tgacgcttgc cgattctaga gggggttttc   120
ggggactttc cgggaa                                                   136

<210> SEQ ID NO 66
<211> LENGTH: 136
<212> TYPE: DNA
<213> ORGANISM: Artificial Sequence
<220> FEATURE:
<223> OTHER INFORMATION: Synthetic sequence

<400> SEQUENCE: 66
gactagacta gttctagagg ctcgacggcg cgtcgcgaca ttctagagtc gcgacggcgc    60
ggctagactc tagaatgcgc ttcctgacag tgacgtcagc cgattctaga gggggttttc   120
ggggactttc cgggaa                                                   136

<210> SEQ ID NO 67
<211> LENGTH: 145
<212> TYPE: DNA
<213> ORGANISM: Artificial Sequence
<220> FEATURE:
<223> OTHER INFORMATION: Synthetic sequence

<400> SEQUENCE: 67
```

```
gactagacta gttctagagt ctagacggcg cggctagcca ttctagagtc tagccggcgc    60
ggcgagcctc tagaatttcc cggaaatagg gtgggcaagt atttccagga aattctagag   120
ggggttttcg gggactttcc gggaa                                         145

<210> SEQ ID NO 68
<211> LENGTH: 107
<212> TYPE: DNA
<213> ORGANISM: Artificial Sequence
<220> FEATURE:
<223> OTHER INFORMATION: Synthetic sequence

<400> SEQUENCE: 68
gactagacta gttctagagg ctagccggcg cgtctagact ctagaatgcg cttcctgaca    60
gtgacgttag ccgattctag agggggtttt cggggacttt ccgggaa                 107

<210> SEQ ID NO 69
<211> LENGTH: 145
<212> TYPE: DNA
<213> ORGANISM: Artificial Sequence
<220> FEATURE:
<223> OTHER INFORMATION: Synthetic sequence

<400> SEQUENCE: 69
gactagacta gttctagagg ctagacggcg cggctagcca ttctagagtc gcgacggcgc    60
gtctagactc tagaatttct cggaaatagg gtgggcaagt atttctcgga aattctagag   120
ggggttttcg gggactttcc gggaa                                         145

<210> SEQ ID NO 70
<211> LENGTH: 145
<212> TYPE: DNA
<213> ORGANISM: Artificial Sequence
<220> FEATURE:
<223> OTHER INFORMATION: Synthetic sequence

<400> SEQUENCE: 70
gactagacta gttctagagt ctcgacggcg cggctagcca ttctagaggc tagacggcgc    60
ggctagcctc tagaatttct cggaaatagg gtgggcaagt atttcccgga aattctagag   120
ggggttttcg gggactttcc gggaa                                         145

<210> SEQ ID NO 71
<211> LENGTH: 96
<212> TYPE: DNA
<213> ORGANISM: Artificial Sequence
<220> FEATURE:
<223> OTHER INFORMATION: Synthetic sequence

<400> SEQUENCE: 71
gactagacta gttctagagg cgagacggcg cgtctagaca ttctggcaag tatttctggg    60
aaattctaga ggggtttttc ggggactttc cgggaa                              96

<210> SEQ ID NO 72
<211> LENGTH: 145
<212> TYPE: DNA
<213> ORGANISM: Artificial Sequence
<220> FEATURE:
<223> OTHER INFORMATION: Synthetic sequence

<400> SEQUENCE: 72
gactagacta gttctagagt ctcgacggcg cgtcgagcca ttctagagtc tagccggcgc    60
```

-continued

```
gtctagcctc tagaatttct cggaaatagg gtgggcaagt atttctcgga aattctagag    120 ggggtttttcg gggactttcc gggaa                                          145

<210> SEQ ID NO 73
<211> LENGTH: 107
<212> TYPE: DNA
<213> ORGANISM: Artificial Sequence
<220> FEATURE:
<223> OTHER INFORMATION: Synthetic sequence

<400> SEQUENCE: 73
gactagacta gttctagagt ctagacggcg cggcgcgcct ctagaatgcg cttcctgaca     60
gtgacgcgag ccgattctag aggggtttt cggggacttt ccgggaa                   107

<210> SEQ ID NO 74
<211> LENGTH: 145
<212> TYPE: DNA
<213> ORGANISM: Artificial Sequence
<220> FEATURE:
<223> OTHER INFORMATION: Synthetic sequence

<400> SEQUENCE: 74
gactagacta gttctagagg cgagccggcg cggcgagcca ttctagagtc gcgacggcgc     60
gtctagcctc tagaatttcc cggaaatagg gtgggcaagt atttccggga aattctagag    120 ggggtttttcg gggactttcc gggaa                                          145

<210> SEQ ID NO 75
<211> LENGTH: 145
<212> TYPE: DNA
<213> ORGANISM: Artificial Sequence
<220> FEATURE:
<223> OTHER INFORMATION: Synthetic sequence

<400> SEQUENCE: 75
gactagacta gttctagagt ctagacggcg cgtctagaca ttctagagtc tcgacggcgc     60
gtctagactc tagaatttcc gggaaatagg gtgggcaagt atttcccgga aattctagag    120 ggggtttttcg gggactttcc gggaa                                          145

<210> SEQ ID NO 76
<211> LENGTH: 145
<212> TYPE: DNA
<213> ORGANISM: Artificial Sequence
<220> FEATURE:
<223> OTHER INFORMATION: Synthetic sequence

<400> SEQUENCE: 76
gactagacta gttctagagt ctagacggcg cgtctcgaca ttctagaggc gagccggcgc     60
gtcgagactc tagaatttct cggaaatagg gtgggcaagt atttctggga aattctagag    120 ggggtttttcg gggactttcc gggaa                                          145

<210> SEQ ID NO 77
<211> LENGTH: 116
<212> TYPE: DNA
<213> ORGANISM: Artificial Sequence
<220> FEATURE:
<223> OTHER INFORMATION: Synthetic sequence

<400> SEQUENCE: 77
gactagacta gttctagagt ctagccggcg cgtcgagact ctagaatttc ccggaaatag     60
ggtgggcaag tatttctggg aaattctaga ggggtttttc gggactttc cgggaa         116
```

-continued

```
<210> SEQ ID NO 78
<211> LENGTH: 145
<212> TYPE: DNA
<213> ORGANISM: Artificial Sequence
<220> FEATURE:
<223> OTHER INFORMATION: Synthetic sequence

<400> SEQUENCE: 78
gactagacta gttctagagt ctagacggcg cggcgagaca ttctagagtc gcgccggcgc       60
gtctagactc tagaatttct gggaaatagg gtgggcaagt atttctggga aattctagag      120
ggggttttcg gggactttcc gggaa                                            145

<210> SEQ ID NO 79
<211> LENGTH: 145
<212> TYPE: DNA
<213> ORGANISM: Artificial Sequence
<220> FEATURE:
<223> OTHER INFORMATION: Synthetic sequence

<400> SEQUENCE: 79
gactagacta gttctagagt ctcgacggcg cgtctagaca ttctagagtc tcgccggcgc       60
gtcgcgactc tagaatttcc cggaaatagg gtgggcaagt atttctggga aattctagag      120
ggggttttcg gggactttcc gggaa                                            145

<210> SEQ ID NO 80
<211> LENGTH: 145
<212> TYPE: DNA
<213> ORGANISM: Artificial Sequence
<220> FEATURE:
<223> OTHER INFORMATION: Synthetic sequence

<400> SEQUENCE: 80
gactagacta gttctagagt ctcgacggcg cgtctagcca ttctagaggc tagccggcgc       60
gtctcgcctc tagaatttcc cggaaatagg gtgggcaagt atttctcgga aattctagag      120 ggggtttttcg gggactttcc gggaa                                           145

<210> SEQ ID NO 81
<211> LENGTH: 145
<212> TYPE: DNA
<213> ORGANISM: Artificial Sequence
<220> FEATURE:
<223> OTHER INFORMATION: Synthetic sequence

<400> SEQUENCE: 81
gactagacta gttctagagt cgagccggcg cggcgagaca ttctagaggc gagacggcgc       60
ggctagactc tagaatttcc gggaaatagg gtgggcaagt atttctcgga aattctagag      120 ggggtttttcg gggactttcc gggaa                                           145

<210> SEQ ID NO 82
<211> LENGTH: 116
<212> TYPE: DNA
<213> ORGANISM: Artificial Sequence
<220> FEATURE:
<223> OTHER INFORMATION: Synthetic sequence

<400> SEQUENCE: 82
gactagacta gttctagagg ctagacggcg cgtcgagact ctagaatttc tgggaaatag       60
ggtgggcaag tatttcccgg aaattctaga ggggtttttc gggactttc cgggaa          116
```

```
<210> SEQ ID NO 83
<211> LENGTH: 145
<212> TYPE: DNA
<213> ORGANISM: Artificial Sequence
<220> FEATURE:
<223> OTHER INFORMATION: Synthetic sequence

<400> SEQUENCE: 83
gactagacta gttctagagt ctcgccggcg cgtcgcgcca ttctagagtc tagacggcgc      60
gtctcgcctc tagaatttct gggaaatagg gtgggcaagt atttctcgga aattctagag     120 ggggtttttcg gggactttcc gggaa                                          145

<210> SEQ ID NO 84
<211> LENGTH: 145
<212> TYPE: DNA
<213> ORGANISM: Artificial Sequence
<220> FEATURE:
<223> OTHER INFORMATION: Synthetic sequence

<400> SEQUENCE: 84
gactagacta gttctagagt cgcgacggcg cgtctagcca ttctagagtc tagacggcgc      60
ggctcgactc tagaatttcc gggaaatagg gtgggcaagt atttccggga aattctagag     120 ggggtttttcg gggactttcc gggaa                                          145

<210> SEQ ID NO 85
<211> LENGTH: 149
<212> TYPE: DNA
<213> ORGANISM: Artificial Sequence
<220> FEATURE:
<223> OTHER INFORMATION: Synthetic sequence

<400> SEQUENCE: 85
tacagggaca gcagagatcc agtttggact agtgtttccg ggaaagggtg ggcaagtttc      60
cgggaaagca gtaggtacag ccttccggga aagggtgggc aagtatttcc gggaaattct     120 agaggggggtt ttcggggact ttccgggaa                                      149

<210> SEQ ID NO 86
<211> LENGTH: 145
<212> TYPE: DNA
<213> ORGANISM: Artificial Sequence
<220> FEATURE:
<223> OTHER INFORMATION: Synthetic sequence

<400> SEQUENCE: 86
gactagacta gttctagagt cgagacggcg cgtcgagcca ttctagaggc gcgccggcgc      60
gtctagactc tagaatttcc gggaaatagg gtgggcaagt atttctggga aattctagag     120 ggggtttttcg gggactttcc gggaa                                          145

<210> SEQ ID NO 87
<211> LENGTH: 145
<212> TYPE: DNA
<213> ORGANISM: Artificial Sequence
<220> FEATURE:
<223> OTHER INFORMATION: Synthetic sequence

<400> SEQUENCE: 87
gactagacta gttctagagt cgagacggcg cgtctagaca ttctagaggc tagacggcgc      60
gtctagcctc tagaatttct gggaaatagg gtgggcaagt atttctcgga aattctagag     120 ggggtttttcg gggactttcc gggaa                                          145
```

```
<210> SEQ ID NO 88
<211> LENGTH: 102
<212> TYPE: DNA
<213> ORGANISM: Artificial Sequence
<220> FEATURE:
<223> OTHER INFORMATION: Synthetic sequence

<400> SEQUENCE: 88
tacagggaca gcagagatcc agtttggact agtgtttccg ggaaagggtg ggcaagtatt        60
tccgggaaat tctagagggg gttttcgggg actttccggg aa                          102

<210> SEQ ID NO 89
<211> LENGTH: 145
<212> TYPE: DNA
<213> ORGANISM: Artificial Sequence
<220> FEATURE:
<223> OTHER INFORMATION: Synthetic sequence

<400> SEQUENCE: 89
gactagacta gttctagagt cgcgacggcg cgtcgagcca ttctagaggc tcgacggcgc        60
ggcgagactc tagaatttct cggaaatagg gtgggcaagt atttccggga aattctagag       120 ggggtttttcg gggactttcc gggaa                                            145

<210> SEQ ID NO 90
<211> LENGTH: 145
<212> TYPE: DNA
<213> ORGANISM: Artificial Sequence
<220> FEATURE:
<223> OTHER INFORMATION: Synthetic sequence

<400> SEQUENCE: 90
gactagacta gttctagagt ctcgacggcg cgtctagaca ttctagagtc gagacggcgc        60
ggctagcctc tagaatttct gggaaatagg gtgggcaagt atttctcgga aattctagag       120
ggggttttcg gggactttcc gggaa                                             145

<210> SEQ ID NO 91
<211> LENGTH: 54
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (28)..(28)
<223> OTHER INFORMATION: R = A/G
<220> FEATURE:
<221> NAME/KEY: misc_feature
<222> LOCATION: (32)..(33)
<223> OTHER INFORMATION: S = C/G
<220> FEATURE:
<221> NAME/KEY: misc_feature
<222> LOCATION: (40)..(41)
<223> OTHER INFORMATION: S = C/G
<220> FEATURE:
<221> NAME/KEY: misc_feature
<222> LOCATION: (45)..(45)
<223> OTHER INFORMATION: Y = C/T

<400> SEQUENCE: 91
gtcgcactag ttctagagac cttgagtrcg tssgtctcts sacgyatgtc taga             54

<210> SEQ ID NO 92
<211> LENGTH: 72
<212> TYPE: DNA
```

```
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: R = A/G
<220> FEATURE:
<221> NAME/KEY: misc_feature
<222> LOCATION: (23)..(23)
<223> OTHER INFORMATION: S = C/G
<220> FEATURE:
<221> NAME/KEY: misc_feature
<222> LOCATION: (31)..(31)
<223> OTHER INFORMATION: M = A/C
<220> FEATURE:
<221> NAME/KEY: misc_feature
<222> LOCATION: (43)..(43)
<223> OTHER INFORMATION: R = A/G
<220> FEATURE:
<221> NAME/KEY: misc_feature
<222> LOCATION: (48)..(48)
<223> OTHER INFORMATION: S = C/G
<220> FEATURE:
<221> NAME/KEY: misc_feature
<222> LOCATION: (56)..(56)
<223> OTHER INFORMATION: M = A/C

<400> SEQUENCE: 92
tcgcactagt tctagarcgt gsctggagtm acagtcctct trcgtgsctg gagtmacagt      60
cctctttcta ga                                                         72

<210> SEQ ID NO 93
<211> LENGTH: 2041
<212> TYPE: DNA
<213> ORGANISM: Artificial Sequence
<220> FEATURE:
<223> OTHER INFORMATION: Synthetic sequence

<400> SEQUENCE: 93
ttccgggaaa gggtgggcaa gtttccggga aagcagtagg tacagccttc cgggaaaggg      60
tgggcaagtt ccgggaaag cagtaggtac agccgggaat ttccggggac tttccgggaa     120
tttccgggga ctttccggga atttccagag cagggaattt ccggggactt ccgggaatt     180 tccgggact ttccgggaat ttccagagca gaccttgagt acgtgcgtct ctgcacgtat     240
gagagcagac cttgagtacg tgcgtctctg cacgtatgag agcatattaa ggtgacgcgt     300
gtggcctcga acaccgagcg accctgcagc gacccgctta aaagcggccg ccatgatgga     360
ttttcaggtg cagattttca gcttcctgct aatcagtgcc tcagtcataa tgtccagagg     420
agatatccag atgacccagt ccccgagctc cctgtccgcc tctgtgggcg atagggtcac     480
catcacctgc cgtgccagtc aggatgtgaa tactgctgta gcctggtatc aacagaaacc     540
aggaaaagct ccgaaactac tgatttactc ggcatccttc ctttattctg gagtcccttc     600
tcgcttctct ggatctagat ctgggacgga tttcactctg accatcagca gtctgcagcc     660
ggaagacttc gcaacttatt actgtcagca acattatact actcctccca cgttcggaca     720
gggtaccaag gtggagatca aacgcactgg gtctacatct ggatctggga agccgggttc     780
tggtgagggt tctgaggttc agctggtgga gtctggcggt ggcctggtgc agccagggg     840 ctcactccgt ttgtcctgtg cagcttctgg cttcaacatt aaagacacct atatacactg     900
ggtgcgtcag gccccgggta agggcctgga atgggttgca aggatttatc ctacgaatgg     960
ttatactaga tatgccgata gcgtcaaggg ccgtttcact ataagcgcag acacatccaa    1020
aaacacagcc tacctgcaga tgaacagcct gcgtgctgag gacactgccg tctattattg    1080
```

-continued

```
ttctagatgg ggaggggacg gcttctatgc tatggacgtg tggggtcaag gaaccctggt   1140
caccgtctcc tcgctcgagg aacaaaaact catctcagaa gaggatctgt tcgtgccggt   1200
cttcctgcca gcgaagccca ccacgacgcc agcgccgcga ccaccaacac cggcgcccac   1260
catcgcgtcg cagcccctgt ccctgcgccc agaggcgtgc cggccagcgg cggggggcgc   1320
agtgcacacg agggggctgg acttcgcctg tgatatctac atctgggcgc ccttggccgg   1380
gacttgtggg gtccttctcc tgtcactggt tatcaccctt tactgcaacc acaggaacag   1440
gagtaagagg agcaggctcc tgcacagtga ctacatgaac atgactcccc gccgccccgg   1500
gcccacccgc aagcattacc agccctatgc cccaccacgc gacttcgcag cctatcgctc   1560
ccgtttctct gttgttaaac ggggcagaaa gaagctcctg tatatattca aacaaccatt   1620
tatgagacca gtacaaacta ctcaagagga agatggctgt agctgccgat ttccagaaga   1680
agaagaagga ggatgtgaac tgagagtgaa gttcagcagg agcgcagacg cccccgcgta   1740
ccagcagggc cagaaccagc tctataacga gctcaatcta ggacgaagag aggagtacga   1800
tgttttggac aagagacgtg gccgggaccc tgagatgggg ggaaagccga gaaggaagaa   1860
ccctcaggaa ggcctgtaca atgaactgca gaaagataag atggcggagg cctacagtga   1920
gattgggatg aaaggcgagc gccggagggg caagggcac gatggccttt accagggtct   1980
cagtacagcc accaaggaca cctacgacgc ccttcacatg caggccctgc cccctcgcta   2040
a                                                                    2041
```